United States Patent
Boussie et al.

(10) Patent No.: US 7,241,715 B2
(45) Date of Patent: *Jul. 10, 2007

(54) BRIDGED BI-AROMATIC LIGANDS, CATALYSTS, PROCESSES FOR POLYMERIZING AND POLYMERS THEREFROM

(75) Inventors: Thomas R. Boussie, Santa Clara, CA (US); Oliver Brümmer, Berlin (DE); Gary M. Diamond, Santa Clara, CA (US); Christopher Goh, North Adams, MA (US); Anne M. LaPointe, Santa Clara, CA (US); Margarete K. Leclerc, Santa Clara, CA (US); James A. W. Shoemaker, Santa Clara, CA (US)

(73) Assignee: Symyx Technologies, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/436,145

(22) Filed: May 16, 2006

(65) Prior Publication Data

US 2006/0211892 A1 Sep. 21, 2006

Related U.S. Application Data

(62) Division of application No. 10/957,036, filed on Sep. 30, 2004, now Pat. No. 7,126,031, which is a division of application No. 10/421,212, filed on Apr. 23, 2003, now Pat. No. 6,841,502.

(60) Provisional application No. 60/375,363, filed on Apr. 24, 2002.

(51) Int. Cl.
*C08F 4/60* (2006.01)
*C08F 4/64* (2006.01)
*C08F 4/642* (2006.01)

(52) U.S. Cl. .............. 502/171; 502/103; 502/167; 526/132; 526/133; 526/134; 526/161; 526/165; 526/172

(58) Field of Classification Search ............ 502/103, 502/167, 171; 526/132, 133, 134, 161, 165, 526/172

See application file for complete search history.

(56) References Cited

U.S. PATENT DOCUMENTS 4,297,465 A 10/1981 Smith (Continued)

FOREIGN PATENT DOCUMENTS

EP 0 277 004 8/1988

(Continued)

OTHER PUBLICATIONS

Agapie et al., "Mechanistic Studies of the Ethylene Trimerization Reaction with Xhromium-Diphosphine Catalysts: Experimental Evidence for a Mechanism Involving Metalacyclic Intermediates", J. Am. Chem. Soc., vol. 126, 2004, pp. 1304-1305.

(Continued)

*Primary Examiner*—Caixia Lu

(57) ABSTRACT

New ligands and compositions with bridged bis-aromatic ligands are disclosed that catalyze the polymerization of monomers into polymers. These catalysts with metal centers have high performance characteristics, including higher comonomer incorporation into ethylene/olefin copolymers, where such olefins are for example, 1-octene, propylene or styrene. The catalysts also polymerize propylene into isotactic polypropylene.

13 Claims, 2 Drawing Sheets front view of complex C5:

U.S. PATENT DOCUMENTS

| | | | |
|---|---|---|---|
| 4,452,914 | A | 6/1984 | Coleman, III et al. |
| 4,971,936 | A | 11/1990 | Wilson et al. |
| 5,064,802 | A | 11/1991 | Stevens et al. |
| 5,093,415 | A | 3/1992 | Brady, III et al. |
| 5,153,157 | A | 10/1992 | Hlatky et al. |
| 5,318,935 | A | 6/1994 | Canich et al. |
| 5,385,993 | A | 1/1995 | Fujita |
| 5,453,410 | A | 9/1995 | Kolthammer et al. |
| 5,599,761 | A | 2/1997 | Turner |
| 5,616,664 | A | 4/1997 | Timmers et al. |
| 5,985,356 | A | 11/1999 | Schultz et al. |
| 6,030,917 | A | 2/2000 | Weinberg et al. |
| 6,175,409 | B1 | 1/2001 | Nielsen et al. |
| 6,214,939 | B1 | 4/2001 | Shinozaki et al. |
| 6,239,236 | B1 | 5/2001 | Morini et al. |
| 6,260,407 | B1 | 7/2001 | Petro et al. |
| 6,262,199 | B1 | 7/2001 | Ewen et al. |
| 6,294,388 | B1 | 9/2001 | Petro |
| 6,306,658 | B1 | 10/2001 | Turner et al. |
| 6,406,632 | B1 | 6/2002 | Safir et al. |
| 6,436,292 | B1 | 8/2002 | Petro |
| 6,454,947 | B1 | 9/2002 | Safir et al. |
| 6,455,316 | B1 | 9/2002 | Turner et al. |
| 6,461,515 | B1 | 10/2002 | Safir |
| 6,475,391 | B2 | 11/2002 | Safir et al. |
| 6,489,168 | B1 | 12/2002 | Wang et al. |
| 6,491,816 | B2 | 12/2002 | Petro |
| 6,491,823 | B1 | 12/2002 | Safir et al. |
| 6,508,984 | B1 | 1/2003 | Turner et al. |
| 6,548,026 | B1 | 4/2003 | Dales et al. |
| 6,713,577 | B2 | 3/2004 | Boussie |
| 6,759,014 | B2 | 7/2004 | Dales et al. |
| 6,841,502 | B2 * | 1/2005 | Boussie et al. ............ 502/125 |
| 6,869,904 | B2 | 3/2005 | Boussie et al. |
| 6,897,276 | B2 | 5/2005 | Boussie et al. |
| 2002/0002256 | A1 | 1/2002 | Peterson |
| 2006/0211892 | A1 | 9/2006 | Boussie et al. |

FOREIGN PATENT DOCUMENTS

| | | |
|---|---|---|
| EP | 0 292 134 | 11/1988 |
| EP | 0 534 405 | 3/1993 |
| EP | 0 582 194 | 2/1994 |
| EP | 0 622 380 | 11/1994 |
| EP | 0 922 712 | 6/1999 |
| EP | 1 110 930 | 6/2001 |
| JP | 08-134064 | 5/1996 |
| JP | 08-217775 | 8/1996 |
| JP | 2002-280179 | 9/2002 |
| WO | WO 94/07926 | 4/1994 |
| WO | WO 94/11409 | 5/1994 |
| WO | WO 98/03521 | 6/1998 |
| WO | WO 99/05186 | 2/1999 |
| WO | WO 99/06413 | 2/1999 |
| WO | WO 99/42467 | 8/1999 |
| WO | WO 00/09255 | 2/2000 |
| WO | WO 01/00581 | 1/2001 |
| WO | WO 01/48028 | 7/2001 |
| WO | WO 01/98371 | 12/2001 |
| WO | WO 02/02576 | 1/2002 |
| WO | WO 02/36638 | 5/2002 |
| WO | WO 02/083306 | 10/2002 |
| WO | WO 02/085820 | 10/2002 |

OTHER PUBLICATIONS

Arrowsmith et al., "Comparison of the Polymerization of Propene by Homogeneous and Heterogeneous Metallocene/MAO-Catalysts Under Different Polymerization Conditions", Macromol. Chem. Phys., vol. 202, 2001. pp. 2161-2167.

Balsells et al., "Insight into the Mechanism of the Asymmetric Addition of Alkyl Groups to Aldehydes Catalyzed by Titanium-BINOLate Species", J. Am. Chem. Soc., vol. 124, 2002, pp. 10336-10348.

Barron, "Alkylalumoxanes: Synthesis, Structure, and Reactivity", Metallocene-Based Polyolefins—Preparation, Properties & Technology, Scheirs and Kaminsky (Eds.), vol. 1, 2000, pp. 33-67.

Bennett et al., "Catalytic Conjugate Addition Promoted by the Copper(1)-monothiobinaphthol System. Part 3. Comparison of Three Thiolate-based Catalytic Systems", J. Chem. Soc., Perkins Trans., vol. 1, 1999, pp. 3127-3132.

Blaser et al., "Enantioselective Synthesis", Appl. Homogeneous Catalysts, vol. 3, 2002, pp. 1131-1149.

Bochmann et al., "Base-Free Cationic Zirconium Benzyl Complexes as Highly Active Polymerization Catalysts", Organometallics, vol. 12, 1993, pp. 633-640.

Brintzinger et al., "Stereospecific Olefin Polymerization with Chiral Metallocene Catalysts", Angew. Chem. Int. Ed. Engl., vol. 34, 1995, pp. 1143-1170.

Carter et al., "High Activity Ethylene Timerisation Catalysts Based on Diphosphine Ligands", Chem. Commun., 2002, pp. 858-859.

Chang et al., "Syntheses of New Lactones Containing Phenyl or Methyl Groups", J. Korean Ind. & Eng. Chemistry, vol. 9, No. 6, Nov. 1998, pp. 842-845.

Chen et al., "Cocatalysts for Metal-Catalyzed Olefin Polymerization: Activators, Activation Processes, and Structure-Activity Relationships", Chem. Rev., vol. 100, 2000, pp. 1391-1434.

Chen et al., "Divalent ansa-Zirconocenes: Stereospecific Synthesis and High Activity for Propylene Polymerization", J. Am. Chem. Soc., vol. 126, 2004, pp. 42-43.

Coates, "Precise Control of Polyolefin Stereochemistry Using Single-Site Metal Catalysts", Chem. Rev., vol. 100, 2000, pp. 1223-1252.

Comils et al., (Eds.), Applied Homogeneous Catalysis with Organometallic Compounds, vol. 1: Applications, 2002, pp. 213-273.

Cornils et al. (Eds.), Applied Homogeneous Catalysis with Organometallic Compounds, vol. 2: Developments, 2002, pp. 740-747.

Cram et al., "A Spherand Containing an Enforced Cavity That Selectively Binds Lithium and Sodium Ions", J.C.S. Chem. Commun., 1979, pp. 948-950.

Cram et al., "Augmented and Diminished Spherands and Scales of Binding", J. Am. Chem. Soc., vol. 103, 1981, pp. 6228-6232.

Cram et al., "Spherand Complexation and Decomplexation Rates with Sodium and Lithium Picrates, and Activation Parameters for Decomplexation", J. Chem. Soc., Chem. Commun., vol. 5, 1982, pp. 301-304.

Cram et al., "Host-Guest Complexation. 33. Search for New Chiral Hosts", J. Org. Chem., vol. 50, 1985, pp. 1486-1496.

Cram et al., "Host-Guest Complexation. 35. Spherands, The First Completely Preorganized Liquid Systems", J. Am. Chem. Soc., vol. 107, 1985, pp. 3645-3657.

Cram et al., "Host-Guest Complexation. 36. Spherand and Lithium and Sodium Ion Complexation Rates and Equilibria", J. Am. Chem. Soc., vol. 107, 1985, pp. 3657-3668.

Cram et al., "Host-Guest Complexation. 52. Bridged and Chiral Hemispherands", J. Org. Chem., vol. 54, 1989, pp. 5460-5482.

Deckers et al., "Catalytic Trimerization of Ethene with Highly Active Cyclopentadienyl-Arene Titanium Catalysts", Organometallics, vol. 21, 2002, pp. 5122-5135.

Deng et al., "Synthesis of High-Melting, Isotactic Polypropene with C(2)- and C(1)-Symmetrical Zirconocenes", Macromolecules, vol. 29, 1996, pp. 6371-6376.

Diamond et al., "Efficient Synthesis of Chiral ansa-Metallocenes by Amine Elimination", J. Am. Chem. Soc., vol. 118, 1996, pp. 8024-8033.

Ewen, "Evaluation of the Dimethylsilyl-Bis(2-Methyl-4-Phenyl-1-Indenyl) Ligand with Group 4 Triad Metals in Propene Polymerizations with Methylaluminoxane", Macromol. Rapid Commun., vol. 19, 1998, pp. 71-73.

Fink, "Propane Polmerization with Silica-Supported Metallocene/MAO Catalysts", Chem. Rev., vol. 100, 2000, pp. 1377-1390.

Fomi et al., "Kinetics and Mechanism of Propylene to 4-Methyl-1-pentene Catalytic Dimerization", Ind. Eng. Chem. Process Des. Develop., vol. 12, 1973, pp. 455-459.

Gibson et al., "The Search for New-Generation Olefin Polymerization Catalysts: Life Beyond Metallocenes", Angew. Chem. Int. Ed. Engl., vol. 38, 1999, pp. 428-447.

Gibson et al., "Advances in Non-Metallocene Olefin Polymerization Catalysis", Chem. Rev., vol. 103, 2003, pp. 283-315.

Gladysz, "Frontiers in Metal-Catalyzed Polymerization: Designer Metallocenes, Designs on New Monomers, Demystifying MAO, Metathesis Deshabille", Chemical Reviews, vol. 100, No. 4, Apr. 2000, 2 pgs.

Helgeson et al., "The Lithium Chloride Complex of the Anti Isomer of the Bridged Spherand C(50)H(48)O(6)", Acta. Crystallographica Section C, vol. 56, 2000, pp. 795-797.

Hlatky, "Heterogeneous Single-Site Catalysts for Olefin Polymerization", Chem. Rev., vol. 100, 2000, pp. 1347-1376.

Hoveyda, "Chiral Zirconium Catalysts for Enantioselective Synthesis", Titanium and Zirconium in Organic Synthesis, Marek (Ed.), Wiley-VCH Verlag GmbH, Weinheim, 2002, pp. 180-229.

Jordan, "Chemistry of Cationic Dicyclopentadienyl Group 4 Metal-Alkyl Complexes", Adv. Organometallic Chem., vol. 32, 1991, pp. 325-387.

Kaminsky et al., "The Influence of the Polymerization Process on the Product Properties of Metallocene-Polypropene", Chem. Eng. Technol., vol. 24, No. 11, 2001, pp. 1124-1128.

Klapars et al., "A General and Efficient Copper Catalyst for the Amidation of Aryl Halides and the N-Arylation of Nitrogen Heterocycles", J. Am. Chem. Soc., vol. 123, No. 31, 2001, pp. 7727-7729.

Knobler et al., "The Crystal and Molecular Structures of Bridged Spherands", J. Incl. Phen. & Molec. Recog. in Chem., vol. 12, 1992, pp. 341-360.

Kol et al., "Isospecific Living Polymerization of 1-Hexene by a Readily Available Nonmetallocene C (2)-Symmetrical Zirconium Catalyst", J. Am. Chem. Soc., vol. 122, No. 43, 2000, pp. 10706-10707.

Kuber, "Metallocenes as a Source of Fine Chemicals", Appl. Homogeneous Catalysis with Organometallic Compounds, Cornils & Herrmann (Eds.), vol. 2, 1996, pp. 893-902.

LaPointe et al., "New Family of Weakly Coordinating Anions", J. Am. Chem. Soc., vol. 122, 2000, pp. 9560-9561.

LoCoco et al., "Chelate-Controlled Synthesis of rac- and meso-Me(2)Si(3-(t)Bu-C(5)H(3))(2)ZrCl(2)", Organometallics, vol. 22, 2003, pp. 5498-5503.

Luongo, "Infrared Study of Polypropylene", J. Appl. Polym. Sci., vol. III, No. 9, 1960, pp. 302-309.

March (Ed.), Advanced Organic Chemistry, 4th Ed., 1992, Wiley, New York.

Marek (Ed.), Titanium and Zirconium in Organic Synthesis, 2002, Wiley-VCH Verlag GmbH, Weinheim.

Marks et al., "Cocatalysts for Metal-Catalyzed Olefin Polymerization: Activators, Activation Processes, and Structure-Activity Relationships", Chem. Rev., vol. 100, 2000, pp. 1391-1434.

Maruoka, "Asymmetric Reactions with Chiral Lewis Acid Catalysts", Ojima (Ed.), Catalytic Asymmetric Synthesis, Chap. 9, 1993, pp. 413-440.

McGuinness et al., "Novel Cr-PNP Complexes as Catalysts for the Trimerisation of Ethylene", Chem. Commun., 2003, pp. 334-335.

McGuinness et al., "First CR(III)-SNS Complexes and Their Use as Highly Efficient Catalysts for the Trimerization of Ethylene to 1-Hexene", J. Am. Chem. Soc., vol. 125, No. 18, 2003, pp. 5272-5273.

Negishi, "Some Newer Aspects of Organizirconium Chemistry of Relevance to Organic Synthesis: Zr-Ca'alyzed Enantioselective Carbometallation", Pure Appl. Chem., vol. 73, No. 2, 2001, pp. 239-242.

Pellecchia et al., "Synthesis, Crystal Structure, and Olefin Polymerization of a Zwitterionic (n6)-Arene Zirconium Tris(hydrocarbyl)", J. Am. Chem. Soc., vol. 115, 1993, pp. 1160-1162.

Pellecchia et al., "Single Insertion of (alpha)-Olefins into the Cationic Complex [Zr(CH(2)Ph(3)] + Affording Isolable [Zr(CH(2)Ph(2)(CH(2)CHRCH(2)Ph)] + Adducts: A Model for the Insertion Mechanism in Ziegler-Natta Polymerization", Organometallics, vol. 13, 1994, pp. 298-302.

Pellecchia et al., "A Novel (n7) Coordination Mode of a Benzyl Ligand a Cationic Zirconium Complex", Organometallics, vol. 13, 1994, pp. 3373-3775.

Piers et al., "New Bifunctional Perfluoroaryl Boranes: Synthesis and Reactivity of the Ortho-Phenylene-Bridged Diboranes . . . ", J. Am. Chem. Soc., vol. 121, 1999, pp. 3244-3245.

Resconi et al., "Selectivity in Propene Polymerization with Metallocene Catalysts", Chem. Rev., vol. 100, 2000, pp. 1253-1345.

Ringwald et al., "Asymmetric Thermal Transformation, a New Way to Enantiopure Biphenyl-Bridged Titanocene and Zirconocene Complexes: Efficient Catalysts for Asymmetric Imine Hydrogenation", J. Am. Chem. Soc., vol. 121, No. 7, 1999, pp. 1524-1527.

Schrock et al., "Synthesis of Titanium, Zirconium, and Hafnium Complexes That Contain Diamido Donor Ligands of the Type [(t-BuN-o-C6H4)2O]2- and an Evaluation of Activated Versions for the Polymerization of 1-Hexene", Organometallics, vol. 18, 1999, pp. 3649-3670.

Scott et al., "Zirconium Catalysed Enantioselective Hydramination/Cyclisation", Chem. Commun., 2004, pp. 894-895.

Stanforth, "Catalytic Cross-Coupling Reactions in Biaryl Synthesis", Tetrahedron, vol. 54, 1998, pp. 263-303.

Sundell, "Isotacticity Determination of Polypropylene Using FT-Raman Spectroscopy", Polymer, vol. 37, No. 15, 1996, pp. 3227-3231.

Svejda et al., "Ethylene Oligomerization and Propylene Dimerization Using Cationic (alpha)-Diimine)nickel(II) Catalysts", Organometallics, vol. 18, No. 1, 1999, pp. 65-74.

Takahashi et al., "An Expedient Route to Some Monoalkyl Ethers of Enantiomerically Pure Bi-Beta-Naphtol", Tetrahedron Asymmetry, vol. 8, No. 18, 1997, pp. 3125-3130.

Ueda et al., "Doubly Helical, Chiral Crown Thioether Fully Preorganized for Planar Coordination", J. Chem. Soc. Chem. Commun., 1995, pp. 935-936.

Vathauer et al., "Extremely Active Polymerization of Propene by Bisindenzylzirconocenes and Tetra(pentafluorophenyl)-borate", Polymer, vol. 42, 2001, pp. 4017-4024.

Walshm "Titanium-Catalyzed Enantioselective Additions of Alkyl Groups to Aldehydes: Mechanistic Studies and New Concepts in Asymmetric Catalysis", Acc. Chem. Res., vol. 36, No. 10, 2003, pp. 739-749.

Walter et al., "Novel Polypropylene Materials", J.M.S.-Pure Appl. Chem., vol. A36, No. 11, 1999, pp. 1613-1639.

Wuff et al., "Active Site Design in a Chemzyme: Development of a Highly Asymmetric and Remarkably Temperature-Independent Catalyst for the Imino Aldol Reaction", Angew. Chem. Int. Ed., vol. 40, 2001, pp. 2271-2274.

Yamashita et al., "Chiral Hetero Diels-Alder Products by Enantioselective and Diastereoeselective Zirconium Catalysts. Scope, Limitation, Mechanism, and Application to the Concise Synthesis of (+)-Prelactone C and (+)-9-Deoxygoniopypyrone", J. Am. Chem. Soc., 125, 2003, pp. 3793-3798.

Zhang et al., "General Synthesis of Racemic Me(2)Si-Bridged Bis(indenyl) Zirconocene Complexes", J. Am. Chem. Soc., vol. 122, 2000, pp. 8093-8094.

* cited by examiner

Figure 1a: front view of complex C5:
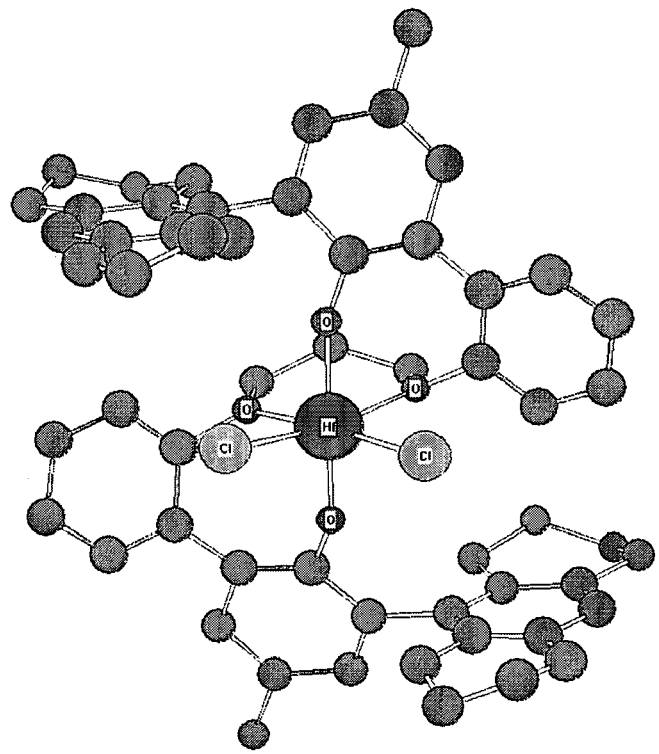
Figure 1b: side view of complex C5
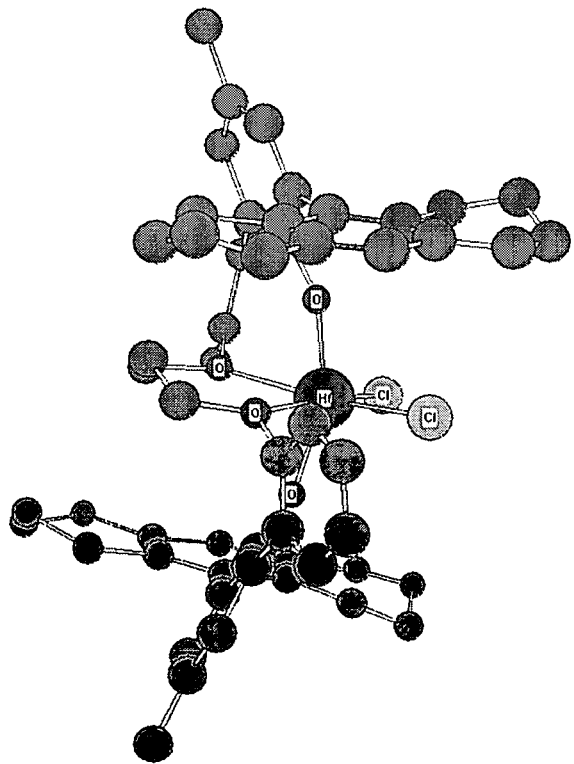

Figure 2: {1H}13C NMR spectra of selected examples, pentad region (25-15 ppm). Polymer samples A-D were obtained at 110° polymerization temperature with ligand-metal compositions as described in example 41. A: LL5 (table 1, entry 1) B: LL4 (table 1 entry 6), C: LL2 (table 2 entry 7), D: LL6 (table 2, entry 20).
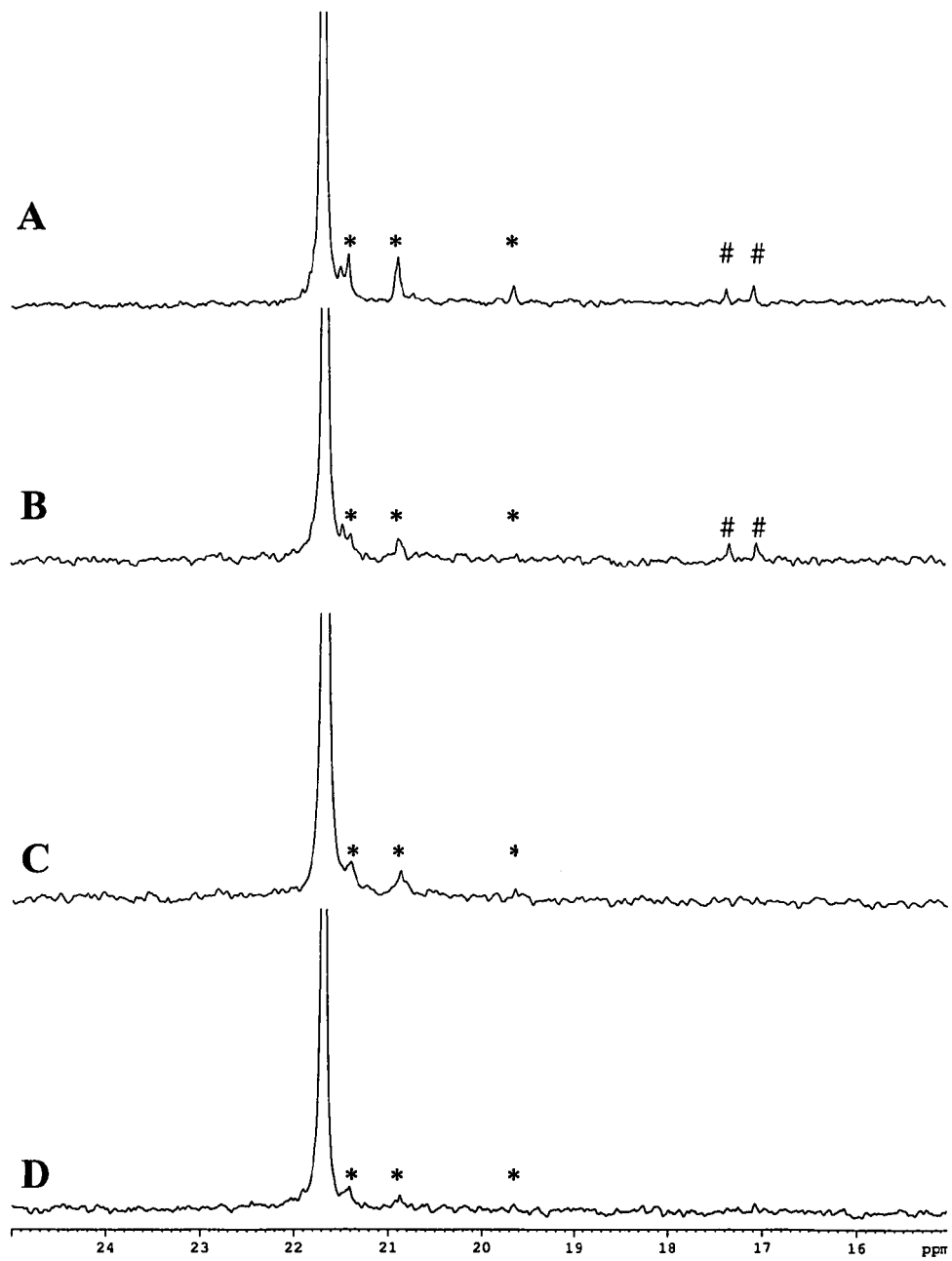
\* Indicates signals of isolated stereoerrors
\# Indicates signals of regioerrors

BRIDGED BI-AROMATIC LIGANDS, CATALYSTS, PROCESSES FOR POLYMERIZING AND POLYMERS THEREFROM

This application is a divisional application of commonly assigned and U.S. application Ser. No. 10/957,036, filed Sep. 30, 2004 now issued as U.S. Pat. No. 7,126,031, which itself is a divisional application of U.S. application Ser. No. 10/421,212, filed Apr. 23, 2003 now issued as U.S. Pat. No. 6,841,502, which itself claims the benefit of U.S. Provisional Application No. 60/375,363 filed on Apr. 24, 2002, each of which are incorporated herein by reference for all purposes.

FIELD OF THE INVENTION

The present invention relates to ligands, complexes, compositions and/or catalysts that provide enhanced olefin polymerization capabilities. The catalysts are based on bridged bi-aromatic ligands and metal precursor compositions and/or metal complexes including such ligands combined with activators (or co-catalysts). The invention also relates to methods of polymerization, and in particular to a high-activity solution polymerization process. The invention also relates to novel polymers and their preparation based on the use of these novel catalysts, including isotactic polypropylene and methods of preparing isotactic polypropylene.

BACKGROUND OF THE INVENTION

Ancillary (or spectator) ligand-metal coordination complexes (e.g., organometallic complexes) and compositions are useful as catalysts, additives, stoichiometric reagents, monomers, solid-state precursors, therapeutic reagents and drugs. Ancillary ligand-metal coordination complexes of this type can be prepared by combining an ancillary ligand with a suitable metal compound or metal precursor in a suitable solvent at a suitable temperature. The ancillary ligand contains functional groups that bind to the metal center(s), remain associated with the metal center(s), and therefore provide an opportunity to modify the steric, electronic and chemical properties of the active metal center(s) of the complex.

Certain known ancillary ligand-metal complexes and compositions are catalysts for reactions such as oxidation, reduction, hydrogenation, hydrosilylation, hydrocyanation, hydroformylation, polymerization, carbonylation, isomerization, metathesis, carbon-hydrogen activation, carbon-halogen activation, cross-coupling, Friedel-Crafts acylation and alkylation, hydration, dimerization, trimerization, oligomerization, Diels-Alder reactions and other transformations.

One example of the use of these types of ancillary ligand-metal complexes and compositions is in the field of polymerization catalysis. In connection with single site catalysis, the ancillary ligand typically offers opportunities to modify the electronic and/or steric environment surrounding an active metal center. This allows the ancillary ligand to assist in the creation of possibly different polymers. Group 4 metallocene based single site catalysts are generally known for polymerization reactions. See, generally, "Chemistry of Cationic Dicyclopentadienyl Group 4 Metal-Alkyl Complexes", Jordan, *Adv. Organometallic Chem.*, 1991, Vol. 32, pp. 325–153 and the references therein, all of which is incorporated herein by reference.

One application for metallocene catalysts is producing isotactic polypropylene. An extensive body of scientific literature examines catalyst structures, mechanism and polymers prepared by metallocene catalysts. See, e.g., Resconi et al., "Selectivity in Propene Polymerization with Metallocene Catalysts," *Chem. Rev.* 2000, 100, 1253–1345 and G. W. Coates, "Precise Control of Polyolefin Stereochemistry Using Single-Site Metal Catalysts," *Chem. Rev.* 2000, 100, 1223–1252 and the references sited in these review articles. Isotactic polypropylene has historically been produced with heterogeneous catalysts that may be described as a catalyst on a solid support (e.g., titanium tetrachloride and aluminum alkyls on magnesium dichloride). This process typically uses hydrogen to control the molecular weight and electron-donor compounds to control the isotacticity. See also EP 0 622 380, EP 0 292 134 and U.S. Pat. Nos. 4,971,936, 5,093,415, 4,297,465, 5,385,993 and 6,239,236.

Given the extensive research activities with respect to metallocene catalysts, there is continued interested in the next generation of non-cyclopentadienyl ligands for olefin polymerization catalysts providing attractive alternatives. See, e.g., "The Search for New-Generation Olefin Polymerization Catalysts: Life beyond Metallocenes", Gibson, et al., *Angew. Chem. Int. Ed.*, 1999, vol. 38, pp. 428–447; *Organometallics* 1999, 18, pp. 3649–3670 and "Advances in Non-Metallocene Olefin polymerization Catalysts", Gibson, et al., *Chem Rev.* 2003, 103, 283–315. Recently, for isotactic polypropylene, bis-amide catalysts have been disclosed in U.S. Pat. No. 5,318,935 and amidinate catalysts have been disclosed in WO 99/05186. See also U.S. Pat. No. 6,214,939 for non-metallocene isotactic polypropylene catalysts.

Isotactic polypropylene and its production has been extensively studied. See, e.g., U.S. Pat. No. 6,262,199 for isotactic polypropylene produced with metallocene catalysts. In general, those of skill in the art have concentrated on $C_2$ symmetrical metal complexes based on the theory that such symmetry allows for tacticity control. See, e.g., "Stereospecific Olefin Polymerization with Chiral Metallocene Catalysts", Brintzinger, et al., *Angew. Chem. Int. Ed. Engl.*, 1995, Vol. 34, pp. 1143–1170. For example, Kol et al., *J. Am. Chem. Soc.* 2000, 122, 10706–10707 and WO 02/36638 disclose a $C_2$-symmetrical structure that may induce tacticity control. However, the art still fails to provide a higher molecular-weight, narrow polydispersity, isotactic polypropylene with a high melting point, in part provided by an isotactic polypropylene having few, if any, regio-errors (or regio-irregularities), produced at high temperatures (e.g., greater than 100° C.) that is commercially desirable.

Therefore, a need exists for the discovery and optimization of non-cyclopentadienyl based catalysts for olefin polymerization, and in particular for certain polymers, such as isotactic polypropylene and ethylene-alpha-olefin copolymers. Furthermore, a need still exists for new catalysts to produce high molecular weight isotactic polypropylene with a high melting point, particularly in a solution process and at higher polymerization temperatures.

SUMMARY OF THE INVENTION

This invention provides a resolution to these needs. This invention discloses enhanced catalytic performances for olefin polymerization when certain ligands are employed in a catalyst, where the ligands are dianionic chelating ligands that can occupy up to four coordination sites of a metal atom and more specifically have a bridged-bis-bi-aryl structure. In addition, some of the ligands, metal complexes and polymers disclosed herein are themselves novel.

This invention discloses catalysts, compositions and complexes (including activated complexes) based on certain bridged bis-bi-aromatic ancillary ligands. For example, the compositions of this invention comprise a ligand and a metal precursor and optionally an activator. In some embodiments, the ligands and the method of making the ligands is also part of this invention.

The catalysts in some embodiments are compositions comprising the ligand and metal precursor, and optionally may additionally include an activator, combination of activators or activator package. In other embodiments, the catalysts are metal-ligand complexes and optionally may additionally include an activator, combination of activators or activator package. For example, the metal-ligand complexes of this invention can be characterized by the general formula:

where (4,2,O,S) is a dianionic ligand having at least 4 atoms that are oxygen or sulfur and chelating to the metal M at at least 2, more specifically 4, coordination sites through oxygen and/or sulfur atoms; M is a metal selected from the group consisting of groups 3–6 and Lanthanide elements of the Periodic Table of Elements, more specifically, from group 4 (Hf, Zr and Ti); L is independently selected from the group consisting of halide (F, Cl, Br, I), optionally substituted alkyl, alkenyl, alkynyl, heteroalkyl, heteroalkenyl, heteroalkynyl, aryl, heteroaryl, alkoxyl, aryloxyl, silyl, boryl, phosphino, amino, alkylthio, arylthio, nitro, hydrido, allyl, diene, phosphine, carboxylates, 1,3-dionates, oxalates, carbonates, nitrates, sulphates, ethers, thioethers and combinations thereof; and optionally two or more L groups may be linked together in a ring structure; n' is 1, 2, 3, or 4.

In another aspect of the invention, a polymerization process is disclosed for monomers. The polymerization process involves subjecting one or more monomers to the catalyst compositions or complexes of this invention under polymerization conditions. The polymerization process can be continuous, batch or semi-batch and can be homogeneous, supported homogeneous or heterogeneous. Another aspect of this invention relates to arrays of ligands, metal precursors and/or metal-ligand complexes. These arrays are useful for the high speed or combinatorial materials science discovery or optimization of the catalyst compositions or complexes disclosed herein.

In particular, a method of producing isotactic polypropylene in a solution process is disclosed and is surprisingly tunable based on the polymerization conditions, activators and substituents on the catalyst. Other polymerization processes that are tunable based on the same criteria are the copolymerization of ethylene and styrene (or substituted styrene) and ethylene and other alpha-olefins with high incorporation of styrene or the alpha-olefin.

Thus, it is an object of this invention to polymerize olefins and unsaturated monomers using metal-ligand complexes. It is also an object of this invention to polymerize olefins and unsaturated monomers using compositions including certain bridged bis-aromatic ligands and metal precursors and/or bridged bis-aromatic ligand-metal complexes.

It is still a further object of this invention to polymerize olefins and unsaturated monomers with the metal-ligand complexes that additionally comprise an activator or combination of activators.

It is also an object of this invention to use non-metallocene group 4 complexes as polymerization catalysts for the production of isotactic polypropylene or other polymers.

Further objects and aspects of this invention will be evident to those of skill in the art upon review of this specification.

BRIEF DESCRIPTION OF THE DRAWINGS

FIG. 1a is an X-ray crystal structure of the compound identified herein as C5 and FIG. 1b is an alternate view of the same crystal structure.

FIG. 2, including parts A, B, C and D, is a spectrum comparing various isotactic polypropylene polymers made in accord with this invention, some with regio-errors and others without detectible regio-errors.

DETAILED DESCRIPTION OF THE INVENTION

As used herein, the phrase "characterized by the formula" is not intended to be limiting and is used in the same way that "comprising" is commonly used. The term "independently selected" is used herein to indicate that the R groups, e.g., $R^1$, $R^2$, $R^3$, $R^4$, and $R^5$ can be identical or different (e.g. $R^1$, $R^2$, $R^3$, $R^4$, and $R^5$ may all be substituted alkyls or $R^1$ and $R^2$ may be a substituted alkyl and $R^3$ may be an aryl, etc.). Use of the singular includes use of the plural and vice versa (e.g., a hexane solvent, includes hexanes). A named R group will generally have the structure that is recognized in the art as corresponding to R groups having that name. The terms "compound" and "complex" are generally used interchangeably in this specification, but those of skill in the art may recognize certain compounds as complexes and vice versa. For the purposes of illustration, representative certain groups are defined herein. These definitions are intended to supplement and illustrate, not preclude, the definitions known to those of skill in the art.

"Optional" or "optionally" means that the subsequently described event or circumstance may or may not occur, and that the description includes instances where said event or circumstance occurs and instances where it does not. For example, the phrase "optionally substituted hydrocarbyl" means that a hydrocarbyl moiety may or may not be substituted and that the description includes both unsubstituted hydrocarbyl and hydrocarbyl where there is substitution.

The term "alkyl" as used herein refers to a branched or unbranched saturated hydrocarbon group typically although not necessarily containing 1 to about 50 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein may contain 1 to about 12 carbon atoms. The term "lower alkyl" intends an alkyl group of one to six carbon atoms, specifically one to four carbon atoms. "Substituted alkyl" refers to alkyl substituted with one or more substituent groups (e.g., benzyl or chloromethyl), and the terms "heteroatom-containing alkyl" and "heteroalkyl" refer to alkyl in which at least one carbon atom is replaced with a heteroatom (e.g., —$CH_2OCH_3$ is an example of a heteroalkyl).

The term "alkenyl" as used herein refers to a branched or unbranched hydrocarbon group typically although not necessarily containing 2 to about 50 carbon atoms and at least one double bond, such as ethenyl, n-propenyl, isopropenyl, n-butenyl, isobutenyl, octenyl, decenyl, and the like. Generally, although again not necessarily, alkenyl groups herein contain 2 to about 12 carbon atoms. The term "lower alkenyl" intends an alkenyl group of two to six carbon atoms, specifically two to four carbon atoms. "Substituted alkenyl" refers to alkenyl substituted with one or more substituent groups, and the terms "heteroatom-containing alkenyl" and "heteroalkenyl" refer to alkenyl in which at least one carbon atom is replaced with a heteroatom.

The term "alkynyl" as used herein refers to a branched or unbranched hydrocarbon group typically although not necessarily containing 2 to about 50 carbon atoms and at least one triple bond, such as ethynyl, n-propynyl, isopropynyl, n-butynyl, isobutynyl, octynyl, decynyl, and the like. Generally, although again not necessarily, alkynyl groups herein may have 2 to about 12 carbon atoms. The term "lower alkynyl" intends an alkynyl group of two to six carbon atoms, specifically three or four carbon atoms. "Substituted alkynyl" refers to alkynyl substituted with one or more substituent groups, and the terms "heteroatom-containing alkynyl" and "heteroalkynyl" refer to alkynyl in which at least one carbon atom is replaced with a heteroatom.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group having one to six, more specifically one to four, carbon atoms. The term "aryloxy" is used in a similar fashion, with aryl as defined below. The term "hydroxy" refers to —OH.

Similarly, the term "alkylthio" as used herein intends an alkyl group bound through a single, terminal thioether linkage; that is, an "alkylthio" group may be represented as —S-alkyl where alkyl is as defined above. A "lower alkyl thio" group intends an alkyl thio group having one to six, more specifically one to four, carbon atoms. The term "arylthio" is used similarly, with aryl as defined below. The term "thioxy" refers to —SH.

The term "allenyl" is used herein in the conventional sense to refer to a molecular segment having the structure —CH=C=CH$_2$. An "allenyl" group may be unsubstituted or substituted with one or more non-hydrogen substituents.

The term "aryl" as used herein, and unless otherwise specified, refers to an aromatic substituent containing a single aromatic ring or multiple aromatic rings that are fused together, linked covalently, or linked to a common group such as a methylene or ethylene moiety. More specific aryl groups contain one aromatic ring or two or three fused or linked aromatic rings, e.g., phenyl, naphthyl, biphenyl, anthracenyl, phenanthrenyl, and the like. In particular embodiments, aryl substituents have 1 to about 200 carbon atoms, typically 1 to about 50 carbon atoms, and specifically 1 to about 20 carbon atoms. "Substituted aryl" refers to an aryl moiety substituted with one or more substituent groups, (e.g., tolyl, mesityl and perfluorophenyl) and the terms "heteroatom-containing aryl" and "heteroaryl" refer to aryl in which at least one carbon atom is replaced with a heteroatom (e.g., rings such as thiophene, pyridine, isoxazole, pyrazole, pyrrole, furan, etc. or benzo-fused analogues of these rings are included in the term "heteroaryl"). In some embodiments herein, multi-ring moieties are substituents and in such an embodiment the multi-ring moiety can be attached at an appropriate atom. For example, "naphthyl" can be 1-naphthyl or 2-naphthyl; "anthracenyl" can be 1-anthracenyl, 2-anthracenyl or 9-anthracenyl; and "phenanthrenyl" can be 1-phenanthrenyl, 2-phenanthrenyl, 3-phenanthrenyl, 4-phenanthrenyl or 9-phenanthrenyl.

The term "aralkyl" refers to an alkyl group with an aryl substituent, and the term "aralkylene" refers to an alkylene group with an aryl substituent; the term "alkaryl" refers to an aryl group that has an alkyl substituent, and the term "alkarylene" refers to an arylene group with an alkyl substituent.

The terms "halo" and "halogen" are used in the conventional sense to refer to a chloro, bromo, fluoro or iodo substituent. The terms "haloalkyl," "haloalkenyl" or "haloalkynyl" (or "halogenated alkyl," "halogenated alkenyl," or "halogenated alkynyl") refers to an alkyl, alkenyl or alkynyl group, respectively, in which at least one of the hydrogen atoms in the group has been replaced with a halogen atom.

The term "heteroatom-containing" as in a "heteroatom-containing hydrocarbyl group" refers to a molecule or molecular fragment in which one or more carbon atoms is replaced with an atom other than carbon, e.g., nitrogen, oxygen, sulfur, phosphorus, boron or silicon. Similarly, the term "heteroalkyl" refers to an alkyl substituent that is heteroatom-containing, the term "heterocyclic" refers to a cyclic substituent that is heteroatom-containing, the term "heteroaryl" refers to an aryl substituent that is heteroatom-containing, and the like. When the term "heteroatom-containing" appears prior to a list of possible heteroatom-containing groups, it is intended that the term apply to every member of that group. That is, the phrase "heteroatom-containing alkyl, alkenyl and alkynyl" is to be interpreted as "heteroatom-containing alkyl, heteroatom-containing alkenyl and heteroatom-containing alkynyl."

"Hydrocarbyl" refers to hydrocarbyl radicals containing 1 to about 50 carbon atoms, specifically 1 to about 24 carbon atoms, most specifically 1 to about 16 carbon atoms, including branched or unbranched, saturated or unsaturated species, such as alkyl groups, alkenyl groups, aryl groups, and the like. The term "lower hydrocarbyl" intends a hydrocarbyl group of one to six carbon atoms, specifically one to four carbon atoms. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom.

By "substituted" as in "substituted hydrocarbyl," "substituted aryl," "substituted alkyl," "substituted alkenyl" and the like, as alluded to in some of the aforementioned definitions, is meant that in the hydrocarbyl, hydrocarbylene, alkyl, alkenyl, aryl or other moiety, at least one hydrogen atom bound to a carbon atom is replaced with one or more substituents that are functional groups such as hydroxyl, alkoxy, alkylthio, phosphino, amino, halo, silyl, and the like. When the term "substituted" appears prior to a list of possible substituted groups, it is intended that the term apply to every member of that group. That is, the phrase "substituted alkyl, alkenyl and alkynyl" is to be interpreted as "substituted alkyl, substituted alkenyl and substituted alkynyl." Similarly, "optionally substituted alkyl, alkenyl and alkynyl" is to be interpreted as "optionally substituted alkyl, optionally substituted alkenyl and optionally substituted alkynyl."

By "divalent" as in "divalent hydrocarbyl", "divalent alkyl", "divalent aryl" and the like, is meant that the hydrocarbyl, alkyl, aryl or other moiety is bonded at two points to atoms, molecules or moieties with the two bonding points being covalent bonds. The term "aromatic" is used in its usual sense, including unsaturation that is essentially delocalized across multple bonds, such as around a ring.

As used herein the term "silyl" refers to the —SiZ$^1$Z$^2$Z$^3$ radical, where each of Z$^1$, Z$^2$, and Z$^3$ is independently selected from the group consisting of hydride and optionally substituted alkyl, alkenyl, alkynyl, heteroatom-containing alkyl, heteroatom-containing alkenyl, heteroatom-containing alkynyl, aryl, heteroaryl, alkoxy, aryloxy, amino, silyl and combinations thereof.

As used herein the term "boryl" refers to the —$BZ^1Z^2$ group, where each of $Z^1$ and $Z^2$ is as defined above. As used herein, the term "phosphino" refers to the group —$PZ^1Z^2$, where each of $Z^1$ and $Z^2$ is as defined above. As used herein, the term "phosphine" refers to the group: $PZ^1Z^2Z^3$, where each of $Z^1$, $Z^3$ and $Z^2$ is as defined above. The term "amino" is used herein to refer to the group —$NZ^1Z^2$, where each of $Z^1$ and $Z^2$ is as defined above. The term "amine" is used herein to refer to the group: $NZ^1Z^2Z^3$, where each of $Z^1$, $Z^2$ and $Z^3$ is as defined above.

The term "saturated" refers to lack of double and triple bonds between atoms of a radical group such as ethyl, cyclohexyl, pyrrolidinyl, and the like. The term "unsaturated" refers to the presence of one or more double and triple bonds between atoms of a radical group such as vinyl, acetylide, oxazolinyl, cyclohexenyl, acetyl and the like.

Other abbreviations used herein include: "$^i$Pr" to refer to isopropyl; "$^t$Bu" to refer to tertbutyl; "Me" to refer to methyl; "Et" to refer to ethyl; and "Ph" refers to phenyl.

The ligands that are suitable for use in the catalysts herein have several general, alternative descriptions. In one embodiment, the ligands are dianionic, chelating ligands that may occupy up to four coordination sites of a metal atom. The ligands can also be described as diaionic ligands that, when chelated to a metal atom, form at least one or two seven member metalocycles (counting the metal atom as one member of the seven member ring). Also, in some embodiments, the ligands can be described as dianionic, chelating ligands that use either oxygen or sulfur as binding atoms to the metal atom. In still other embodiments, the ligands can be described as non-metallocene ligands that can coordinate in an approximate $C_2$-symmetcial complex with a metal atom. These embodiments can be used together or separately.

For example, suitable ligands useful in this invention may be characterized by the following general formulas:

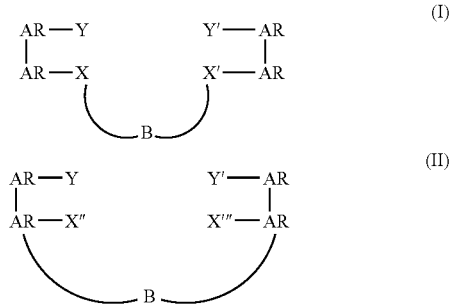

wherein each ligand has at least two hydrogen atoms capable of removal in a binding reaction with a metal atom or metal precursor or base; AR is an aromatic group that can be the same or different from the other AR groups with, generally, each AR being independently selected from the group consisting of optionally substituted aryl or heteroaryl; B is a bridging group having from one to 50 atoms (not counting hydrogen atoms); X and X' are the same or different and are independently selected from the group consisting of oxygen, sulfur, —$NR^{30}$—, —$PR^{30}$—, where $R^{30}$ is selected from the group consisting of hydride, halide, and optionally substituted hydrocarbyl, heteroatom-containing hydrocarbyl, silyl, boryl, alkoxy, aryloxy and combinations thereof; X" and X'" are the same or different and are independently selected from the group consisting of optionally substituted amino, phosphino, hydroxy, alkoxy, aryloxy, thioxy, alkylthio and arylthio; Y and Y' are the same or different and are independently selected from the group consisting of optionally substituted amino, phosphino, hydroxy, alkoxy, aryloxy, thioxy, alkylthio and arylthio; when the AR group attached to the bridge is an optionally substituted heteroaryl, X and/or X' can be part of the aromatic ring. The difference between formulas I and II are that the bridge is either directly attached to the aromatic ring (formula II) or is attached to the aromatic ring via the X and/or X' group (formula I).

In formula I and formula II, it is required that there be at least 2 hydrogen atoms associated with each ligand that are capable of being removed in a complexation reaction with a metal atom or metal precursor or base. In some embodiments, prior to such a complexation reaction, a base may be reacted with the ligand to form a salt, the product of which may then be reacted with a metal precursor (as described herein). In some embodiments at least two of X, X', Y and Y' or at least two of X", X'", Y and Y' have at least one hydrogen atom. In some embodiments, $R^{30}$ is selected from the group consisting of hydride and optionally substituted alkyl, alkenyl, alkynyl, heteroalkyl, heteroalkenyl, heteroalkynyl, aryl, heteroaryl, alkoxyl, aryloxyl, silyl, boryl, phosphino, amino, thioxy, alkylthio, arylthio, halide, nitro, and combinations thereof. In some embodiments, X and X' are independently selected from the group consisting of oxygen, sulfur and —$NR^{30}$—; and in still other embodiments X and X' are independently selected from the group consisting of oxygen and sulfur. In some embodiments, Y and Y' are selected from the group consisting of amino, hydroxy, alkoxy, aryloxy, thioxy, alkylthio and arylthio; and in still other embodiments Y and Y' are independently selected from the group consisting of hydroxy and thioxy.

Generally, the "upper aromatic ring" is the ring to which a Y group (such as Y, Y') is bonded or part of. Similarly, the "lower aromatic ring" is the ring to which an X group (such as X, X', X", etc.) is bonded or part of. In some embodiments, at least one AR is a heteroaromatic and more specifically a heteroaryl group. In other embodiments, at least one upper aromatic ring is a heteroaromatic and more specifically a heteroaryl. Other embodiments include those where at least one lower aromatic ring is a heteroaromatic and more specifically a heteroaryl.

In some embodiments, the bridging group B is selected from the group consisting of optionally substituted divalent hydrocarbyl and divalent heteroatom containing hydrocarbyl. In other embodiments, B is selected from the group consisting of optionally substituted divalent alkyl, alkenyl, alkynyl, heteroalkyl, heteroalkenyl, heteroalkynyl, aryl, heteroaryl and silyl. In still other embodiments, B can be represented by the general formula -($Q''R^{40}_{2-z''}$)$_{z'}$— wherein each Q" is either carbon or silicon and each $R^{40}$ may be the same or different from the others such that each $R^{40}$ is selected from the group consisting of hydride and optionally substituted hydrocarbyl, and optionally two or more $R^{40}$ groups may be joined into a ring structure having from 3 to 50 atoms in the ring structure (not counting hydrogen atoms); and z' is an integer from 1 to 10, more specifically from 1–5 and even more specifically from 2–5 and z" is 0, 1 or 2. For example, when z" is 2, there is no $R^{40}$ groups associated with Q", which allows for those cases where one Q" is multiply bonded to a second Q". In more specific embodiments, $R^{40}$ is selected from the group consisting of hydride, halide, and optionally substituted alkyl, alkenyl, alkynyl, heteroalkyl, heteroalkenyl, heteroalkynyl, aryl, heteroaryl, alkoxyl, aryloxyl, silyl, boryl, phosphino, amino, thioxy, alkylthio, arylthio, and combinations thereof. Specific B groups within these embodiments include —(CH$_2$)$_2$—, —(CH$_2$)$_3$—, —(CH$_2$)$_4$—, and —(CH$_2$)—(C$_6$H$_4$)—(CH$_2$)—. Other specific bridging moieties are set forth in the example ligands and complexes herein.

In other embodiments, the ligands can be characterized by the general formula:

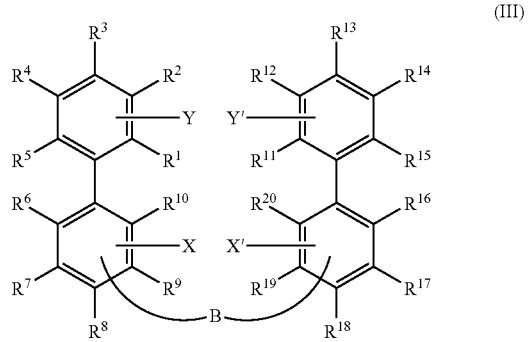

(III)

wherein each of R$^1$, R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, R$^{16}$, R$^{17}$, R$^{18}$, R$^{19}$, and R$^{20}$ is independently selected from the group consisting of hydride, halide, and optionally substituted hydrocarbyl, heteroatom-containing hydrocarbyl, alkoxy, aryloxy, silyl, boryl, phosphino, amino, thioxy, alkylthio, arylthio, nitro, and combinations thereof; optionally two or more R groups can combine together into ring structures (for example, single ring or multiple ring structures), with such ring structures having from 3 to 12 atoms in the ring (not counting hydrogen atoms); B is a bridging group having from one to 50 atoms (not counting hydrogen atoms); X and X' and Y and Y' are as defined above. The notation —Y, —Y', —X and —X' is intended to mean that the group can be part of the aromatic ring (forming a heteroaryl) and/or replace one or more of the R groups (R$^1$–R$^{20}$). The notation for the bridging group B (∪B∪) can be combined with either or both —X and —X' or the bridging group can replace one or more of the R groups on the indictated structure (e.g., such as R$^9$ and/or R$^{19}$). In those embodiments where the bridging group B is not combined with the —X and/or —X' group, X and X' are defined as X'' and X''', above.

In more specific embodiments, each of R$^1$, R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, R$^{15}$, R$^{16}$, R$^{17}$, R$^{19}$, and R$^{20}$ is independently selected from the group consisting of hydride, halide, and optionally substituted alkyl, heteroalkyl, aryl, heteroaryl, alkoxyl, aryloxyl, silyl, boryl, phosphino, amino, thioxy, alkylthio, arylthio, nitro, and combinations thereof. In even more specific embodiments, each of R$^1$, R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, R$^{16}$, R$^{17}$, R$^{18}$, R$^{19}$, and R$^{20}$ is independently selected from the group consisting of hydride, halide, and optionally substituted alkyl, heteroalkyl, aryl, heteroaryl, alkoxyl, aryloxyl, silyl, amino, alkylthio and arylthio. In some embodiments, at least one of R$^2$ and R$^{12}$ is not hydrogen and in still other embodiments both R$^2$ and R$^{12}$ are not hydrogen.

In more specific embodiments, the ligands useful in this invention can be characterized by the formula:

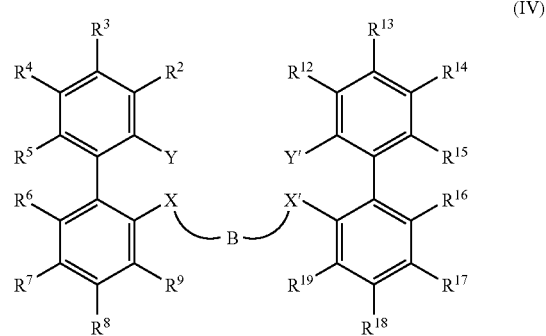

(IV)

wherein R$^2$, R$^3$, R$^4$, R$^5$, R$^6$, R$^7$, R$^8$, R$^9$, R$^{12}$, R$^{13}$, R$^{14}$, R$^{15}$, R$^{16}$, R$^{17}$, R$^{18}$, and R$^{19}$ are as defined above, B is as defined above, X and X' are as defined above, and Y and Y' are as defined above with the proviso that each of Y and Y' include hydrogen.

In more specific embodiments, the ligands useful in this invention can be characterized by the formula:

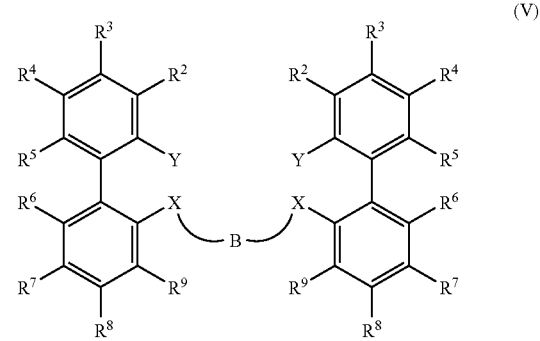

(V)

In formula (V), the bridging group has been made part of the X moieties and the bis-aryl moieties have been made the same as each other. The Y moieties again include hydrogen. In addition, in formula (V), each of R$^2$, R$^3$, R$^4$, R$^5$, R$^6$, R$^7$, R$^8$ and R$^9$ is independently selected from the group consisting of hydride, halide, and optionally substituted alkyl, alkenyl, alkynyl, heteroalkyl, heteroalkenyl, heteroalkynyl, aryl, heteroaryl, alkoxyl, aryloxyl, silyl, boryl, phosphino, amino, thioxy, alkylthio and arylthio, nitro, and combinations thereof.

Specific ligands within the scope of this invention include:

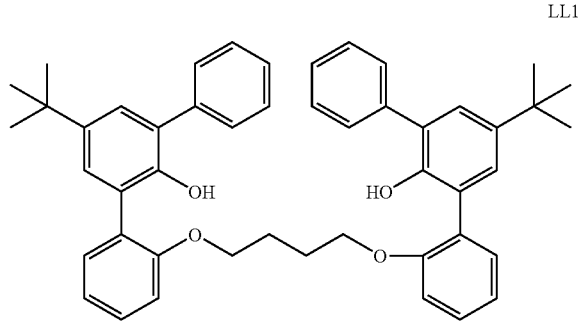

LL1

LL2
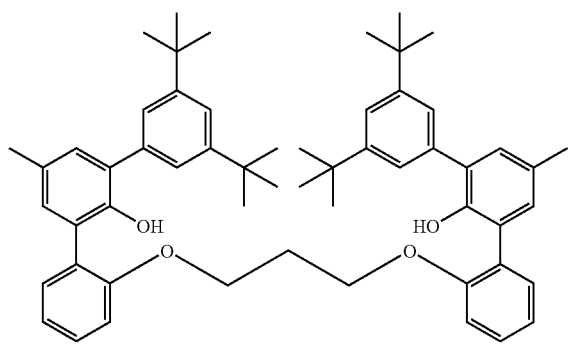
LL6
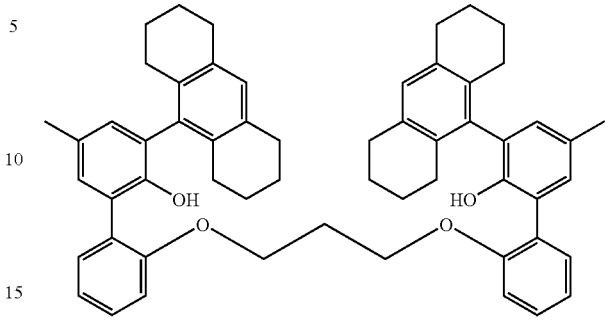
LL3
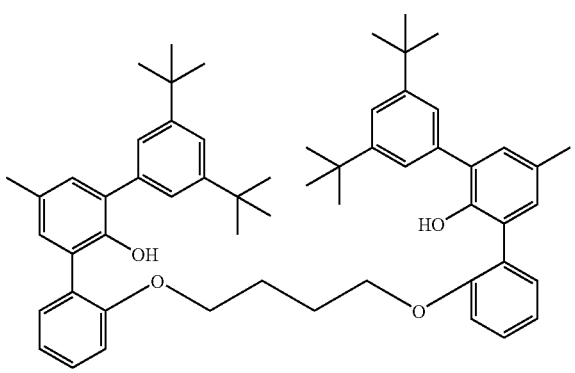
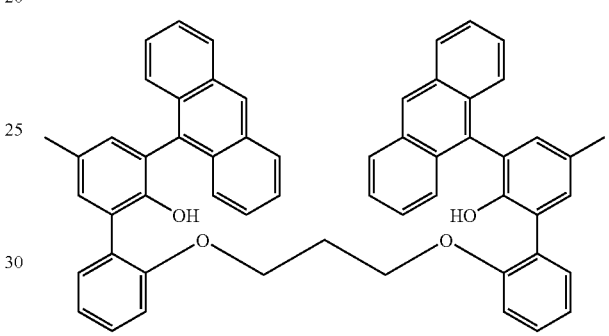
LL4
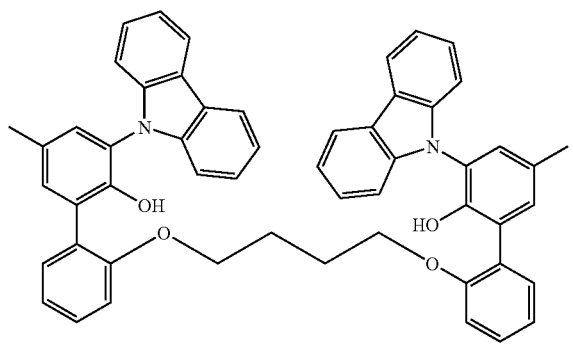
LL52
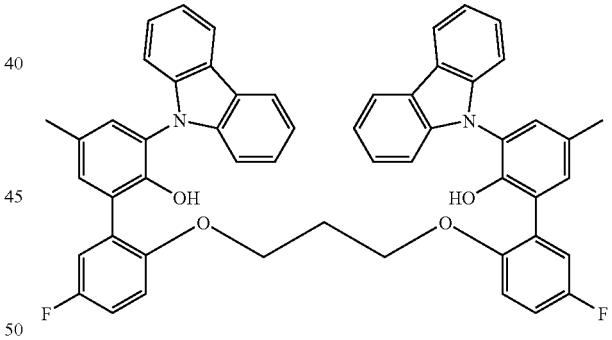
LL5
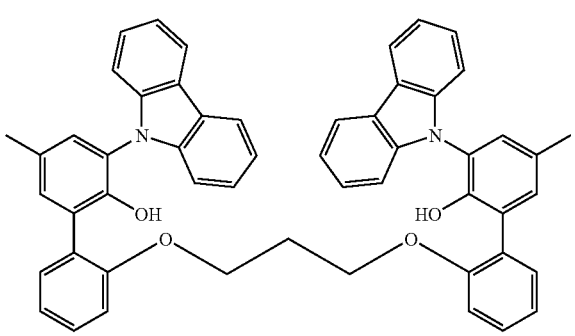
LL53
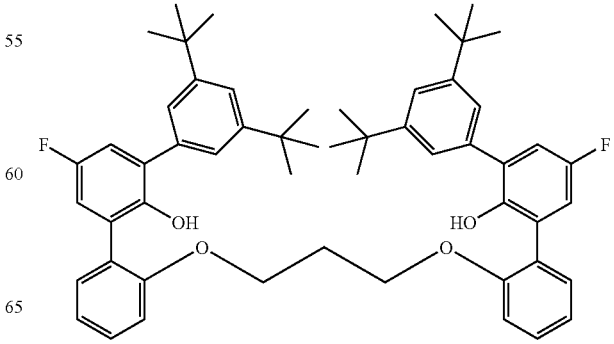

-continued
LL54
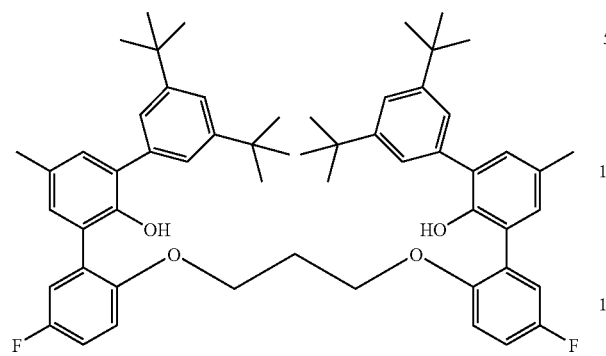
LL55
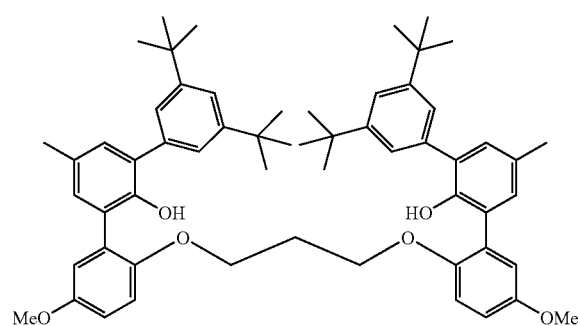
LL56
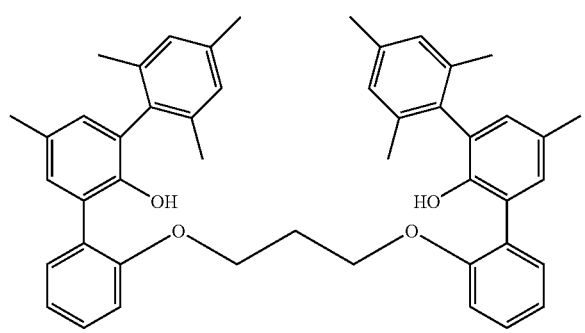
LL57
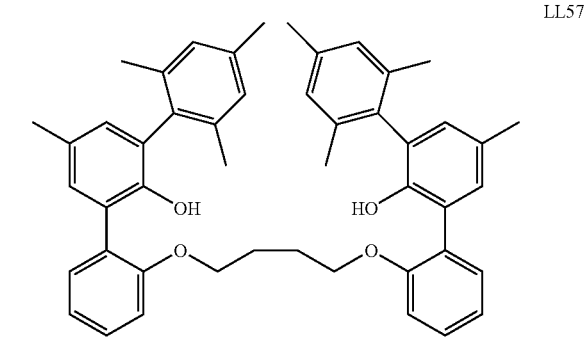
-continued
LL7
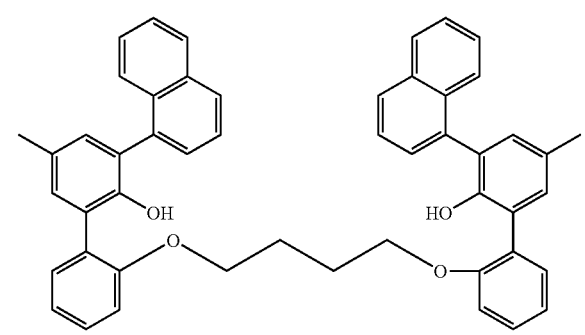
LL8
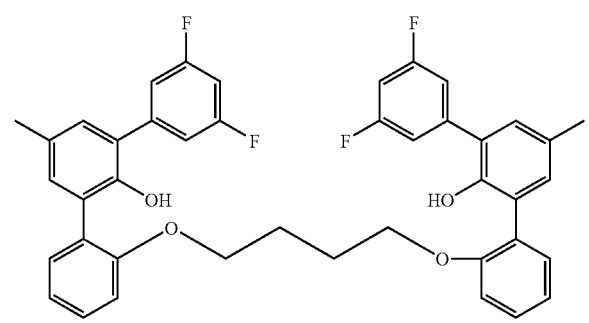
LL9
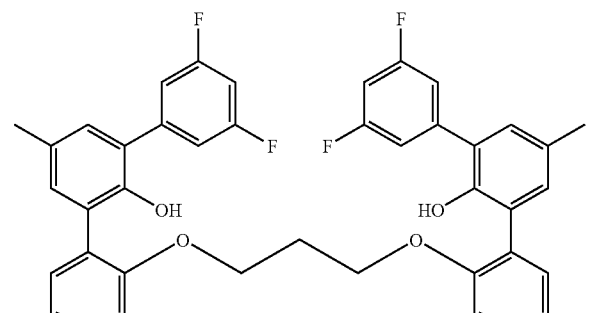
LL10
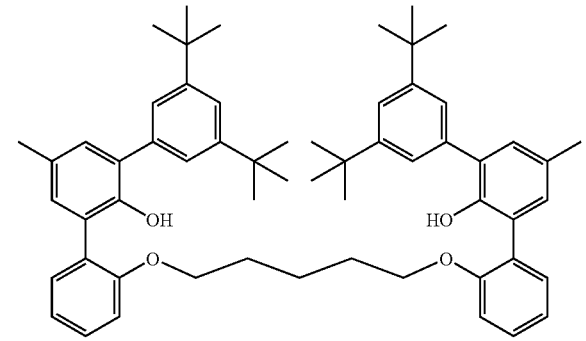

-continued
LL11
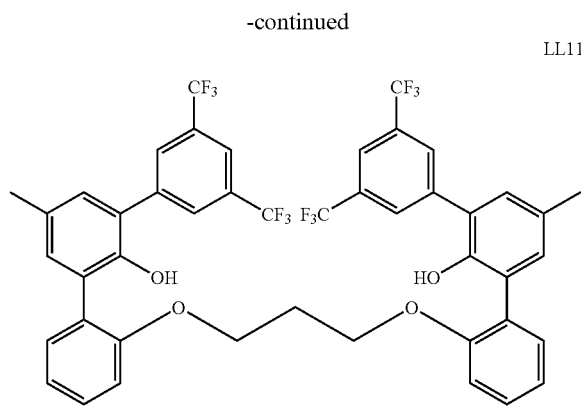
LL15
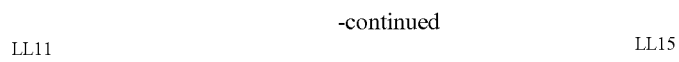
LL12
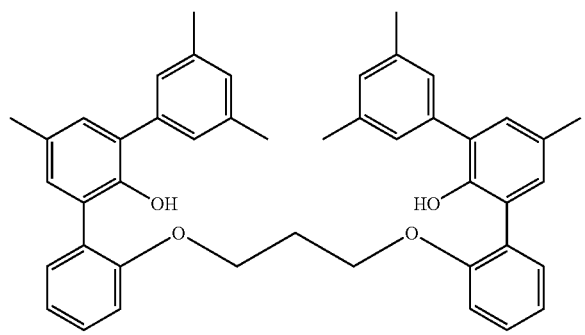
LL16
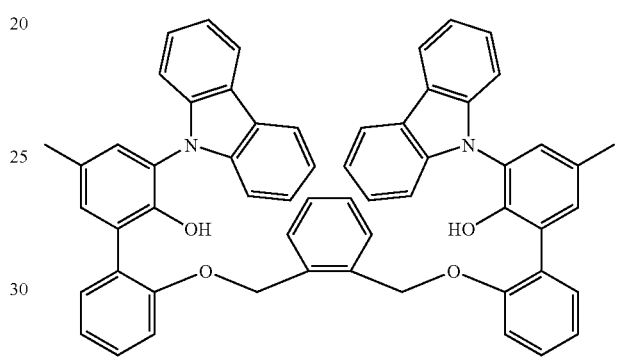
LL13
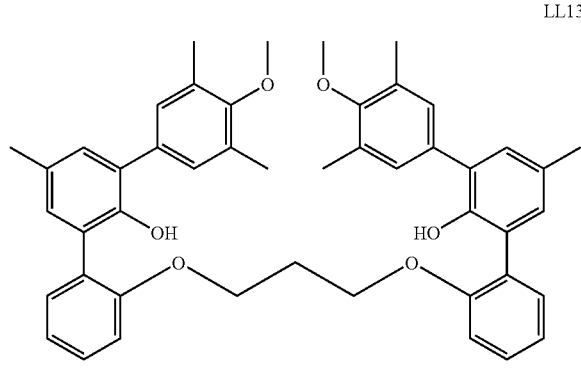
LL17
LL14
LL18
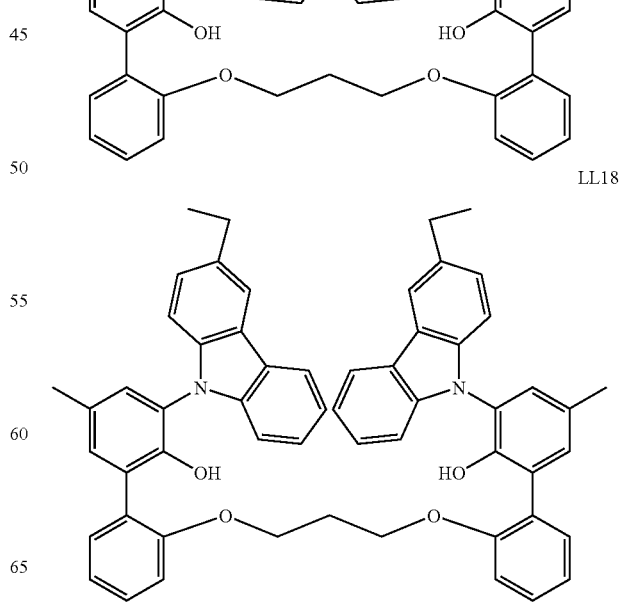

-continued

-continued
LL29
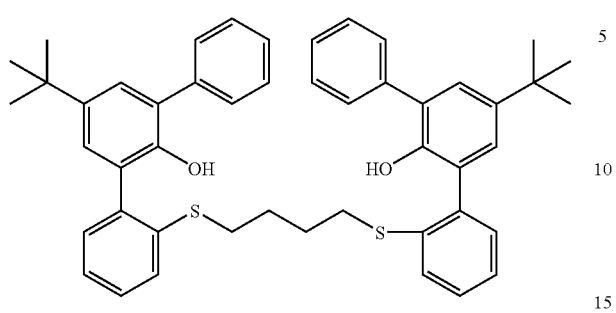
LL30
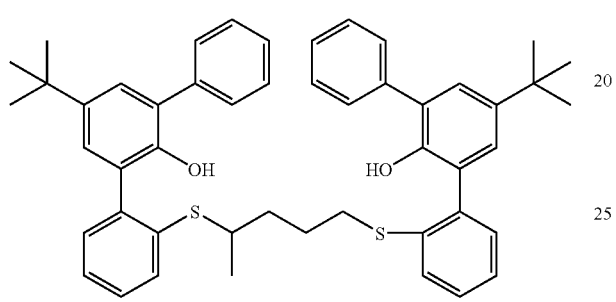
LL31
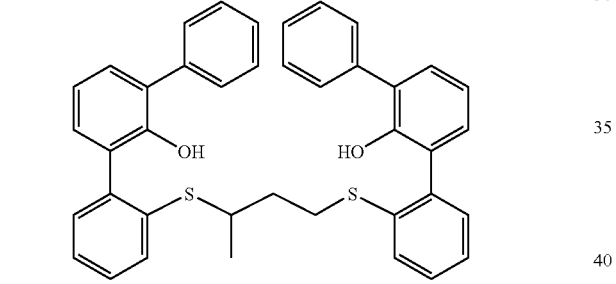
LL32
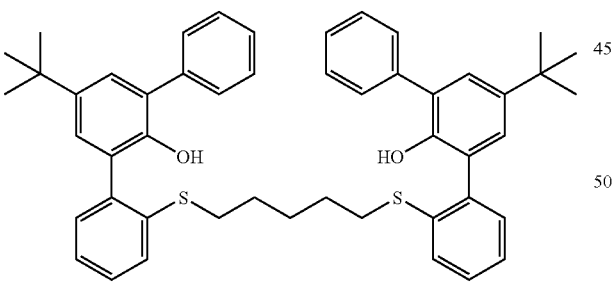
LL33
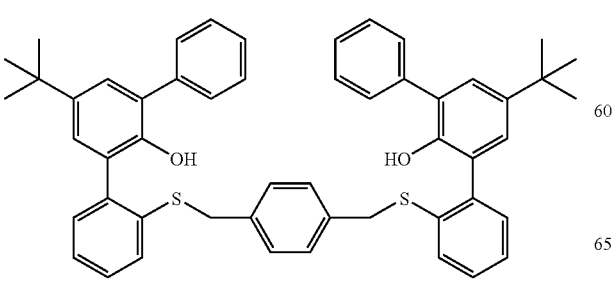
-continued
LL34
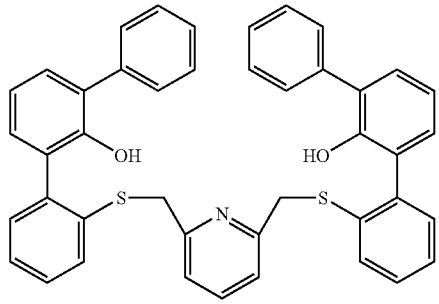
LL35
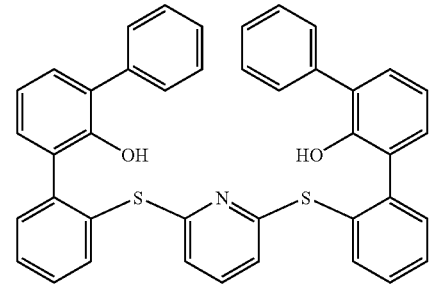
LL36
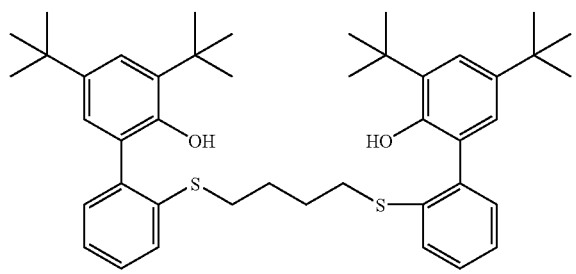
LL37
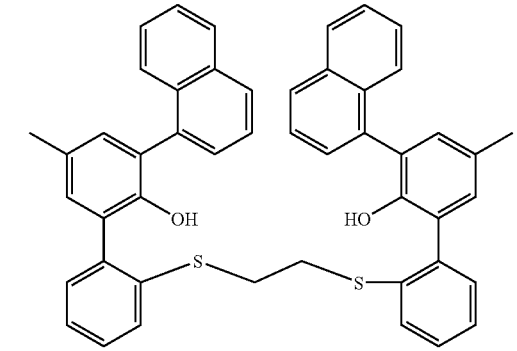
LL38
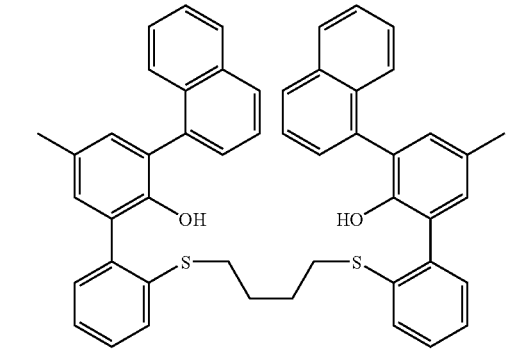

-continued
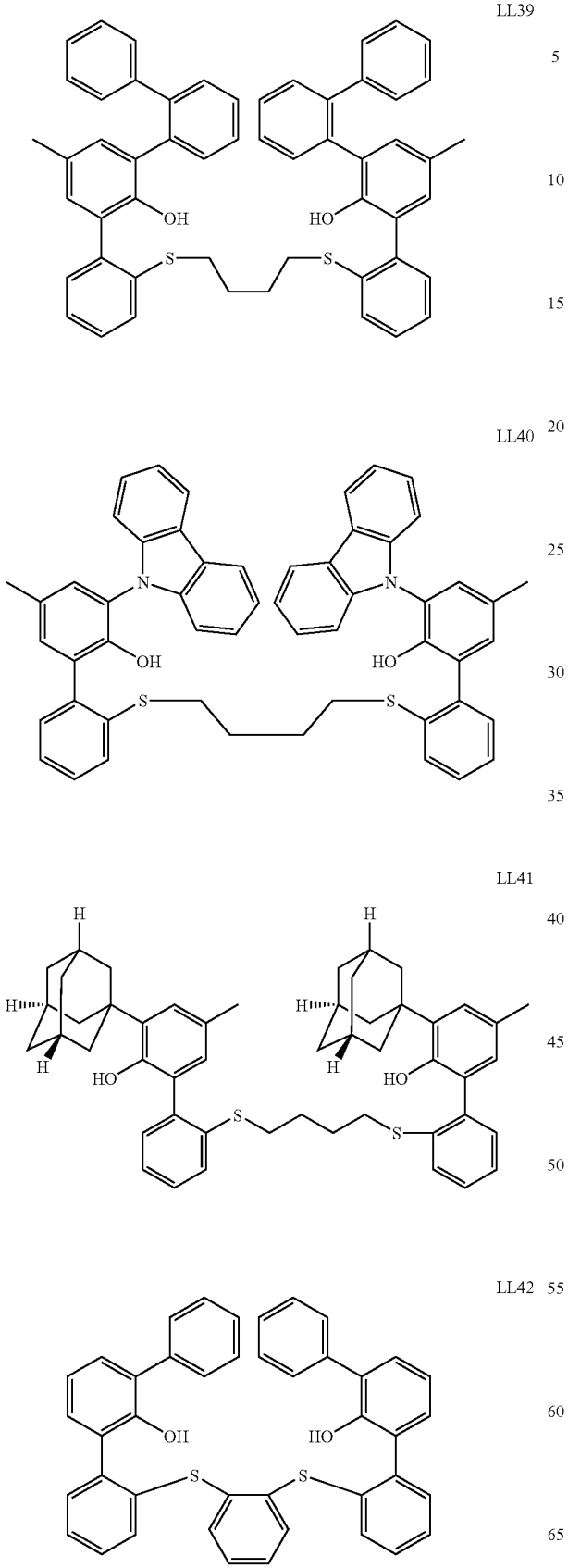

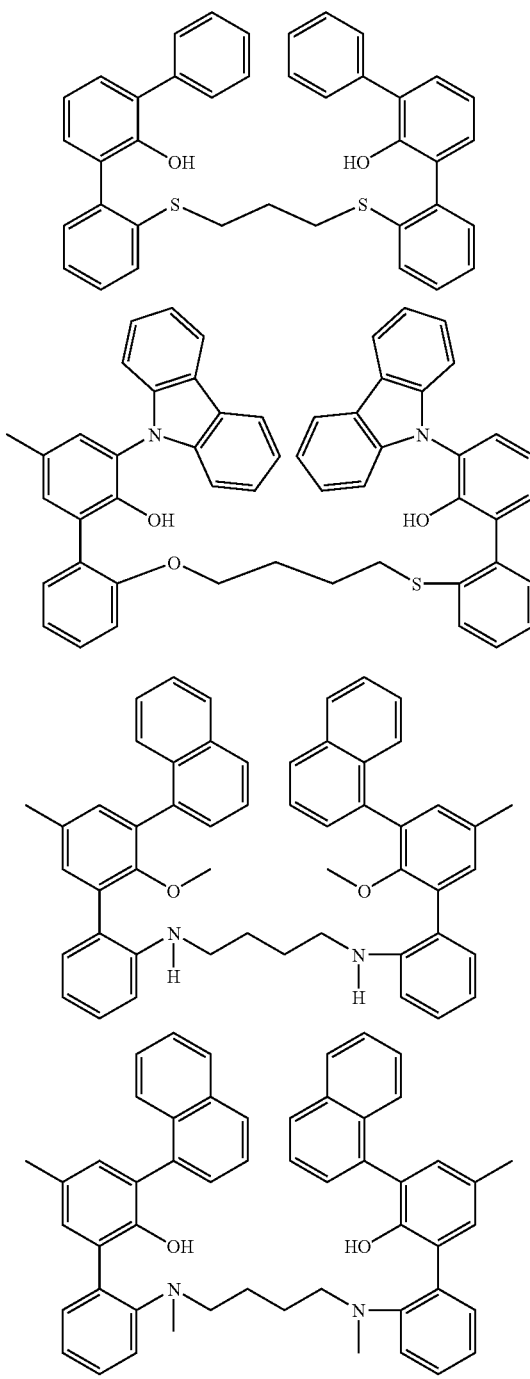

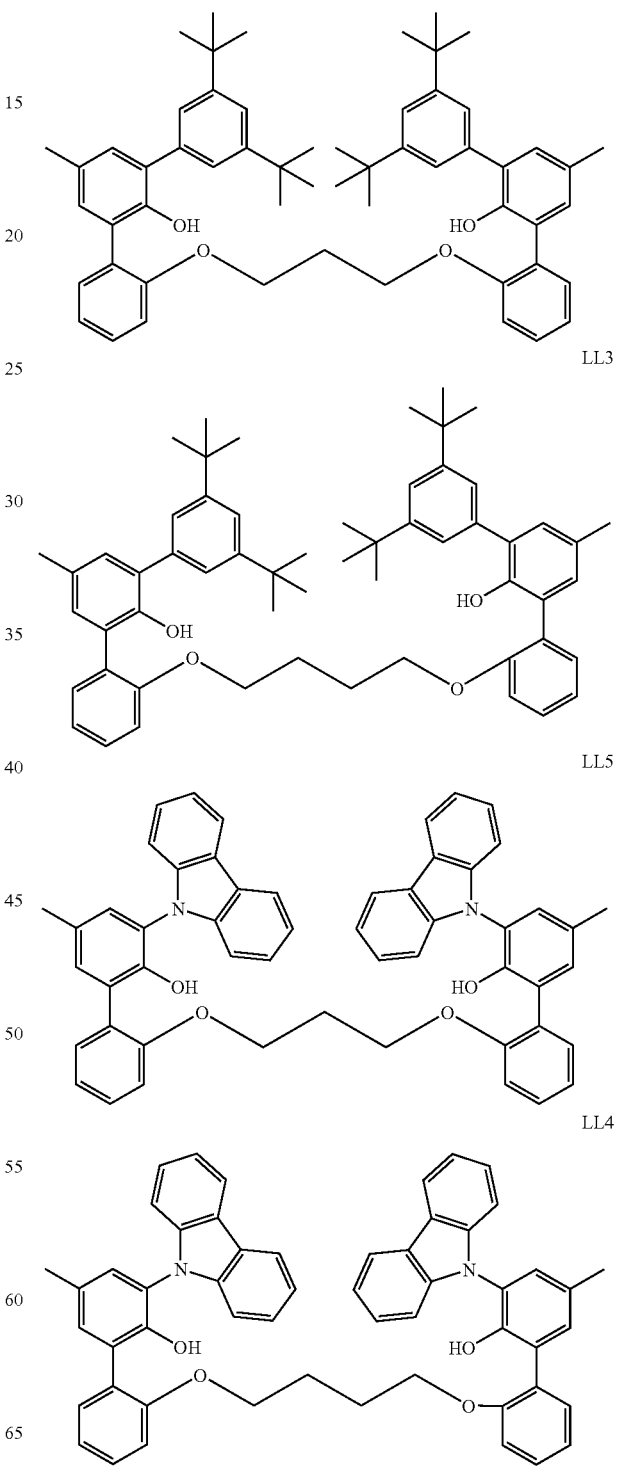

are bulky substituents and may be independently selected from the group consisting of optionally substituted cycloalkylaryl, aryl and heteroaryl. More specifically, each $R^2$ and/or $R^{12}$ is independently selected from the group consisting of optionally substituted aryl and heteroaryl. Specific $R^2$ and/or $R^{12}$ groups include carbozole, 3,5-bis-tert-butyl-phenyl, 1,2,3,4,5,6,7,8-octahydroanthacenyl, 1-naphthyl, 9-anthracenyl and 2,4,6-trimethylphenyl. Specific ligands within the scope of this particularization for bulky substituents include:

In some embodiments the choice of X, X', Y, Y', $R^2$, $R^{12}$ and B have a strong influence on the production of isotactic polypropylene in a solution process. Specific ligands within the scope of this particularization include for example: LL1–LL10, LL12–LL23, LL26–LL32, LL37–LL40, LL45–LL49 and LL52–LL57.

In some embodiments, the size and identity of the substituents on the AR-Y and AR-Y', such as the $R^2$ and/or $R^{12}$ groups, has an influence on the production of isotactic polypropylene in a solution process, allowing for a range of isotactic polypropylene polymers to be prepared with desired properties. Thus, in such embodiments, $R^2$ and $R^{12}$

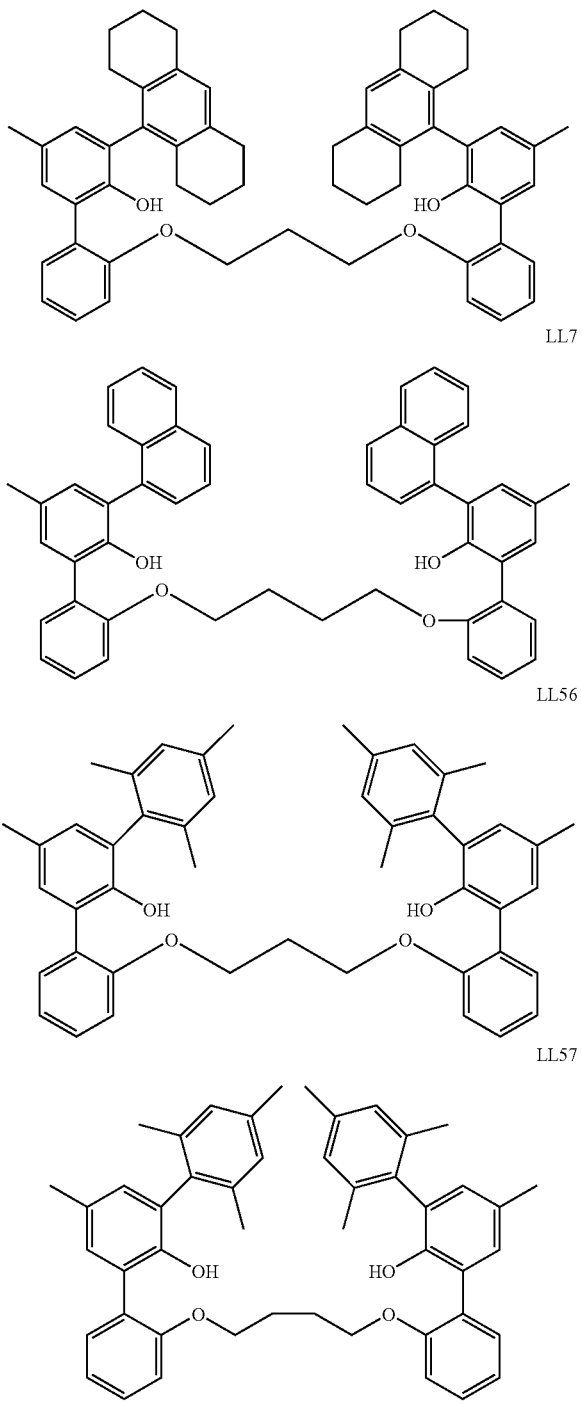

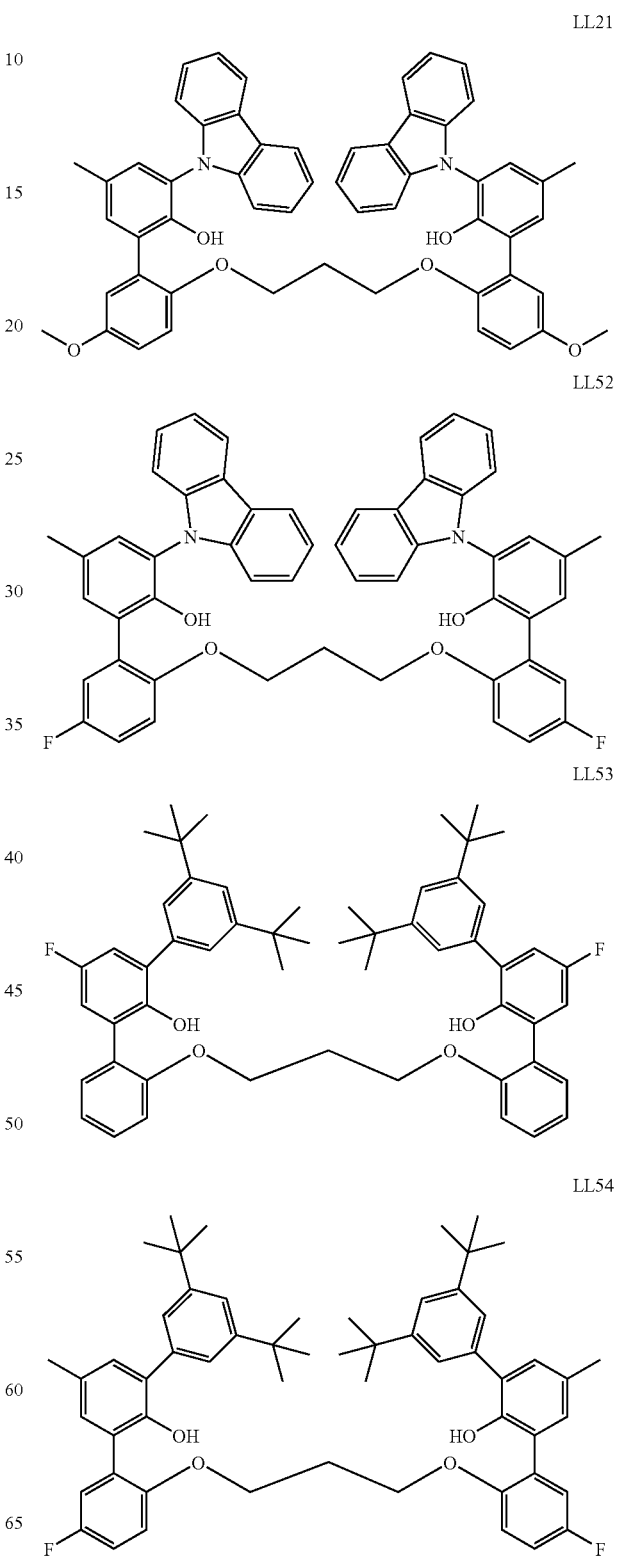

arylthio. Similarly in such embodiments, $R^4$ and $R^{14}$ may be independently selected from the group consisting of halo and optionally substituted hydrocarbyl, alkoxy, aryloxy, dialkyl- or diarylamino, alkyl- or arylthio. Specific ligands within the scope of this particularization include:

In some embodiments, the size and identity of the substituents on the upper aromatic ring (e.g., AR-X and AR-X'), such as the $R^7$ and/or $R^{17}$ groups, has an influence on the production of isotactic polypropylene in a solution process, allowing for a range of isotactic polypropylene polymers to be prepared with desired properties. Thus, in such embodiments, $R^7$ and $R^{17}$ may be independently selected from the group consisting of halo and optionally substituted hydrocarbyl, alkoxy, aryloxy, dialkyl- or diarylamino, alkyl- or -continued

LL55

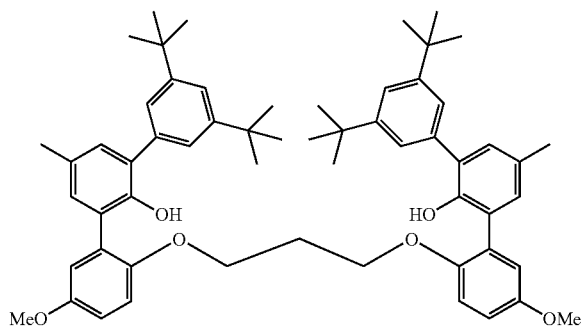

Certain of the ligands are novel compounds and those of skill in the art will be able to identify such compounds from the above. Also, certain embodiments of these ligands are preferred for the polymerization of certain monomers in a catalytic composition and/or in a metal complex. These certain embodiments are discussed further below.

In some embodiments, the ligands of the invention may be prepared using known procedures. See, for example, Advanced Organic Chemistry, March, Wiley, New York 1992 (4th Ed.). Specifically, the ligands of the invention may be prepared using a variety of synthesis routes, depending on the variation desired in the ligand. In general, building blocks are prepared that are then linked together with a bridging group. Variations in the R group substituents can be introduced in the synthesis of the building blocks. Variations in the bridge can be introduced with the synthesis of the bridging group.

Specific ligands within the scope of this invention may be prepared according to the general schemes shown below, where building blocks (designated BB) are first prepared and then coupled together. There are several different ways to use these building blocks. In one embodiment, generally, each of the optionally substituted phenyl rings is prepared as a separate building block (schemes 1 (a and b) and 2). The desired optionally substituted phenyls are then combined into bi-phenyl building blocks (schemes 3 and 4), which are then bridged together (schemes 7, 8, 9, and 10). In another embodiment, the optionally substituted phenyl building blocks are bridged together (schemes 5 and 6) and then additional optionally substituted phenyl building blocks are added to form the bridged bi-aryl structures (schemes 11, 12, 13, and 14). In addition, schemes to effect certain substitutions on the phenyl groups are included (schemes 15, 16, 17 and 18). In many of these schemes, cross coupling reactions are used (e.g., Suzuki, Negishi or Buchwald-Hartwig cross coupling). These cross coupling reactions are generally known in the art; for example, see *Tetrahedron*, 1998, 54(3/4), 263–303 and *J. Am. Chem. Soc.* 2001, 123(31), 7727–7729. The starting materials or reagents used in these schemes are generally commercially available, or are prepared via routine synthetic means.

To facilitate the description of the ligand synthesis techniques used, following are some abbreviations that are used in this description (including the schemes): PG="protecting group", which typically means a phenol or thiophenol protecting group including, but not limited to: methyl (Me), benzyl (Bn), substituted benzyl (2-methoxyphenylmethyl: MPM, etc.), alkoxymethyl (methoxymethyl:MOM, etc.), tetrahydropyranyl (THP), silyl (trimethylsilyl:TMS, tert-butyldimethylsilyl:TBS, etc.) and allyl (Allyl); LG="leaving group"=leaving group for nucleophilic displacement reactions group including, but not limited to: chloro, bromo, iodo, tosyl (para-toluenesulfonyl) and triflic (trifluoromethylsulfonyl). The symbol

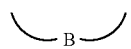

depicts a bridging moiety as defined elsewhere in this specification. The term "upper phenyl ring" is used consistently with the term "upper aromatic ring", described above. The term "lower phenyl ring" is used consistently with the term "lower aromatic ring", described above.

Scheme 1a below is a general building block synthesis scheme, specifically depicting the synthesis of Y-protected, 2-bromo substituted, upper phenyl ring building blocks:

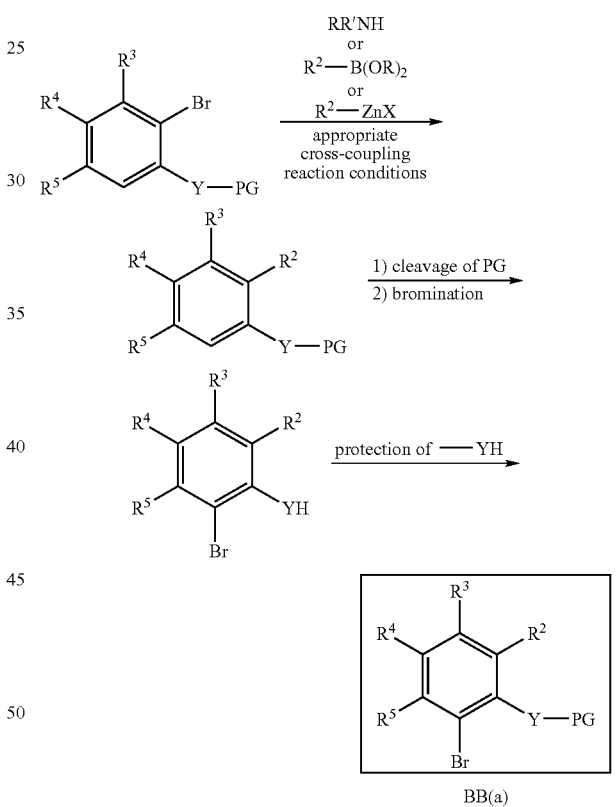

As shown in Scheme 1a, a protecting group (PG) is used to prepare the appropriate building block (BB(a)). The substituents on the building block are as defined above. The variables R and R' are generally selected from the same group as $R^2$, and may be optionally substituted alkyl, aryl, amino and the like; optionally R and R' may be linked or fused. "Appropriate cross-coupling reaction conditions" are generally known to those of skill in the art, and may be found in the above-cited references. Other reaction conditions will be known to those of skill in the art, with reference to the examples herein.

As an alternative, Scheme 1b shows a general synthesis scheme for Y-protected, 2-bromo substituted, upper phenyl ring building blocks:

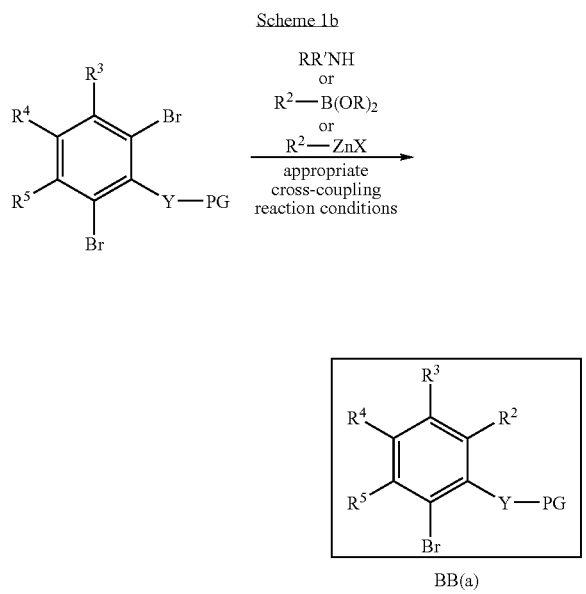

In scheme 1b, the variables are defined as discussed above.

Scheme 2 below is a general scheme for the synthesis of X-protected 2-boronic ester substituted lower phenyl ring building blocks, X-protected 2-ZnCl substituted lower-ring building blocks, and X-deprotected 2-boronic acid substituted lower ring building blocks:

In scheme 2, the variables are defined as discussed above. In addition the phrase "cat. H⁺" refers to an acid catalyzed reaction that supplies a hydrogen ion, such as p-toluenesulfonic acid (TsOH) or hydrochloric acid (HCl), as is known to those of skill in the art.

Scheme 3 below is a general scheme for the synthesis of Y-protected upper phenyl ring, X-deprotected lower phenyl ring building block:

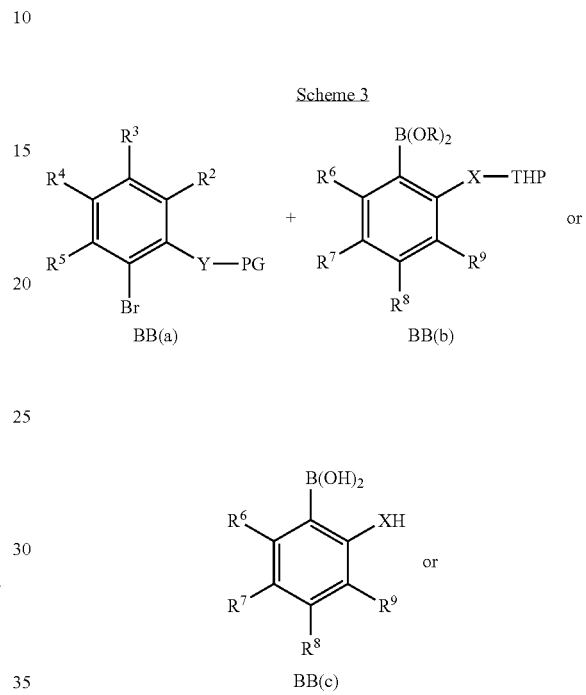

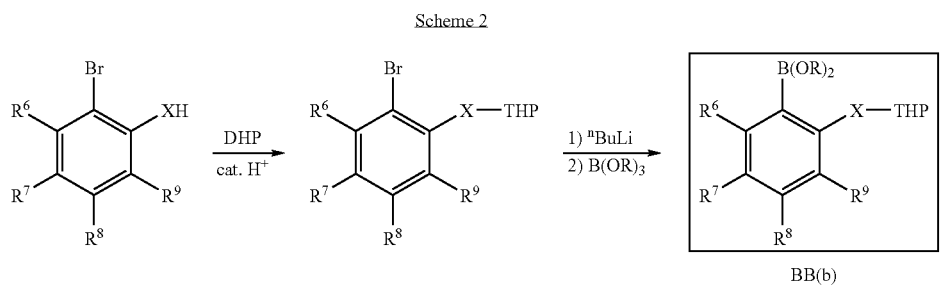

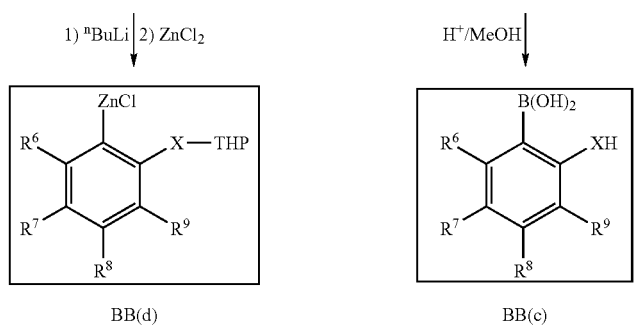

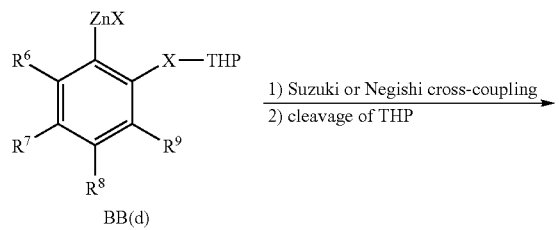

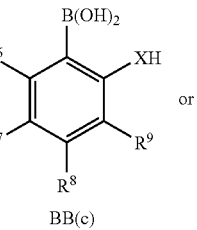

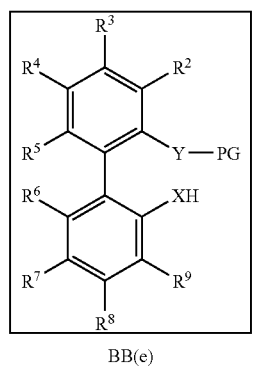

In scheme 3, the variables are defined as discussed above.

Scheme 4 below is a general scheme for the synthesis of 2-bromo substituted, Y-protected upper phenyl ring, X-deprotected lower phenyl ring building block:

Scheme 4

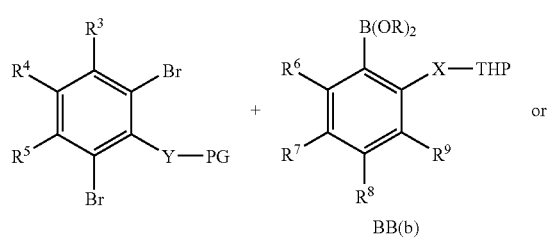

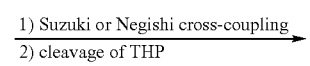

In scheme 4, the variables are defined as discussed above.

Scheme 5 below is a general scheme for the synthesis of symmetric 2-Br substituted, 2-boronic ester-substituted and 2-ZnCl-substituted, bridged lower phenyl ring building blocks:

Scheme 5

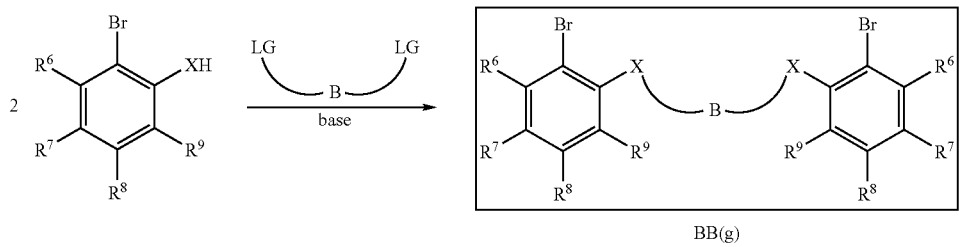

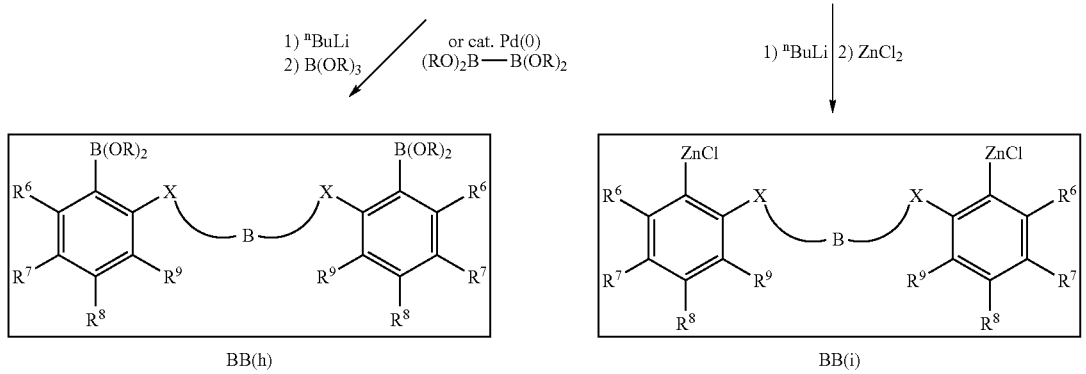

In scheme 5, the variables are defined as discussed above. In addition the phrase "base" refers to bases in general (such as cesium carbonate or potassium tert-butoxide), as is known to those of skill in the art. Also the phrase "cat. Pd(0)" refers to a catalyst that uses a ligand-stabilized Pd⁰ complex, known to those of skill in the art.

Scheme 6 below is a general scheme for the synthesis of unsymmetric 2-Br substituted, 2-boronic ester-substituted and 2-ZnCl-substituted, bridged lower phenyl ring building blocks:

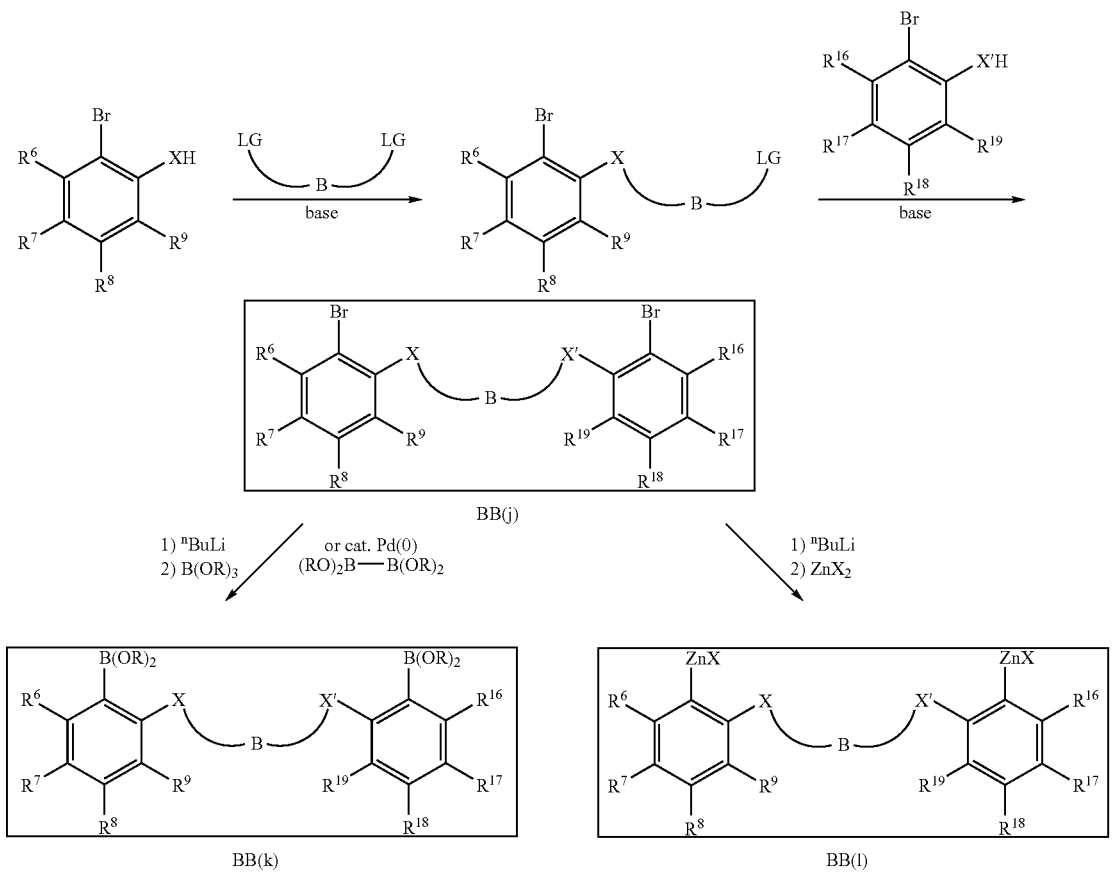

In scheme 6, the variables are defined as discussed above.

Scheme 7 below is a general scheme for the synthesis of symmetric Y-protected, upper phenyl ring 2-bromo-substituted, lower phenyl ring bridged building blocks:

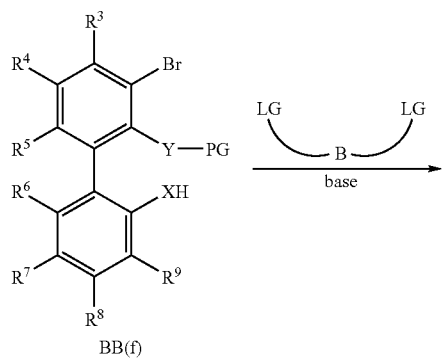

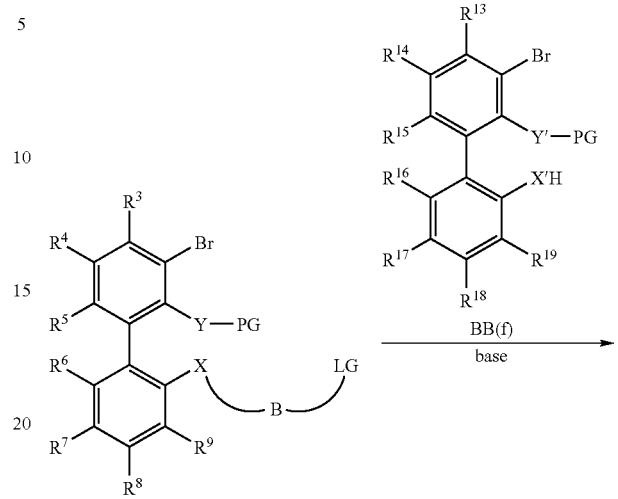

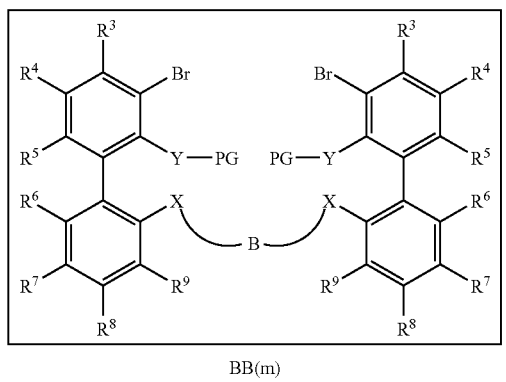

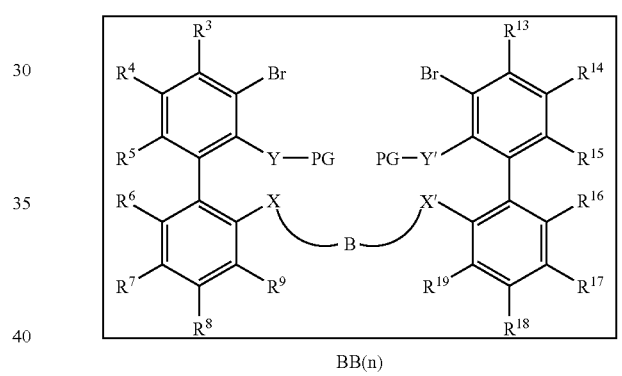

In scheme 7, the variables are defined as discussed above.

Scheme 8 below is a general scheme for the synthesis of unsymmetric Y,Y'-protected, upper phenyl ring 2-bromo-substituted, lower phenyl ring bridged building blocks:

In scheme 8, the variables are defined as discussed above.

Scheme 9 below is a general scheme for the double reaction of building block BB(e) with bridge, followed by deprotection:

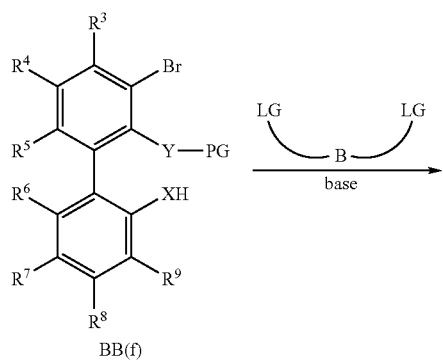

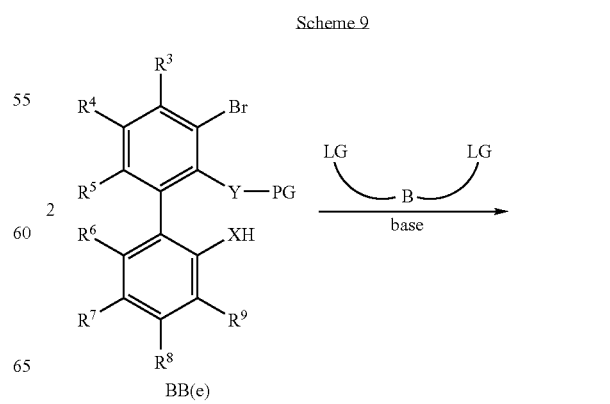

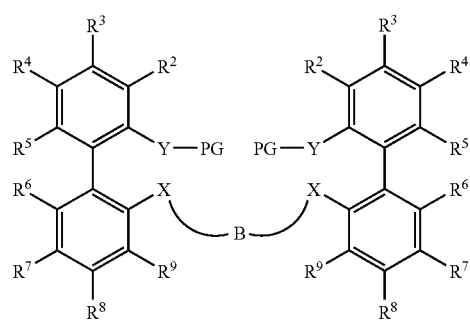
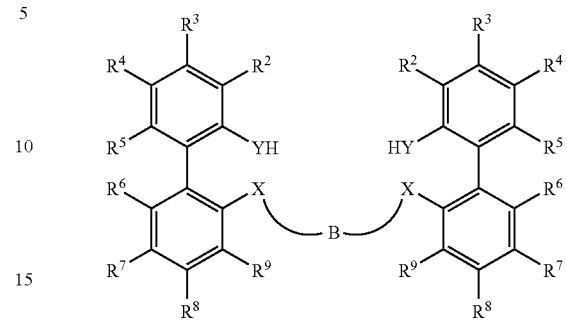
In scheme 9, the variables are defined as discussed above.
Scheme 10 below is a general scheme for the sequential reaction of building blocks BB(e) and BB(f) with bridge, followed by deprotection:
Scheme 10
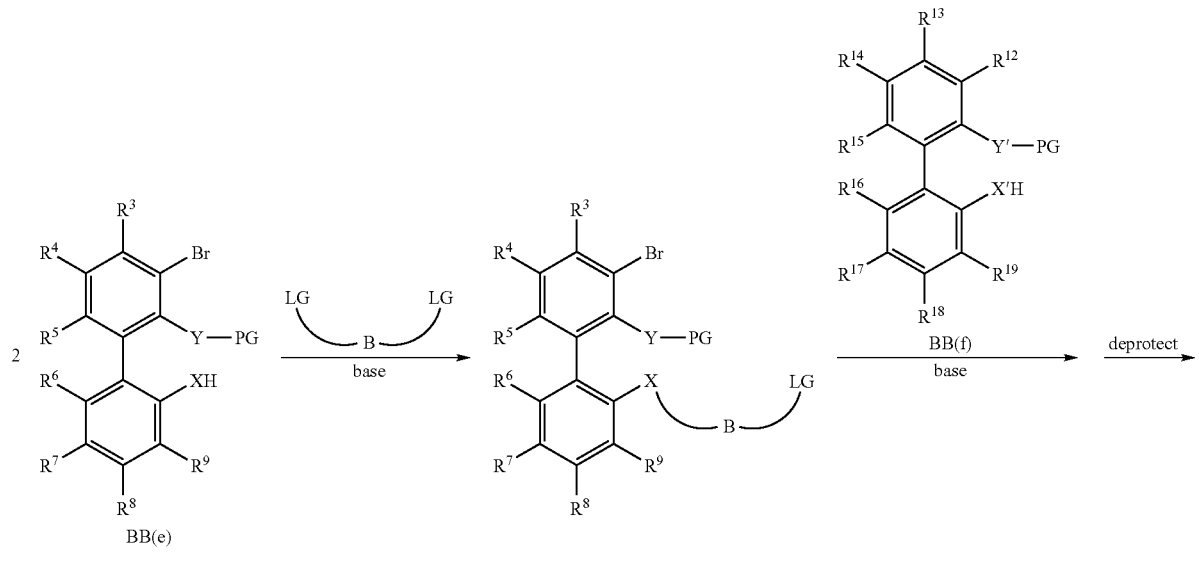
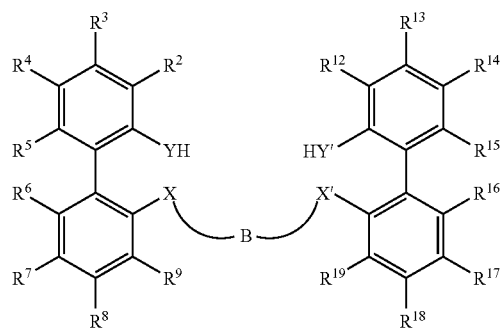
In scheme 10, the variables are defined as discussed above.

Scheme 11 below is a general scheme for the conversion of building block BB(a) to a boronic ester or ZnCl derivative, followed by double cross-coupling with building block BB(g) and subsequent deprotection:

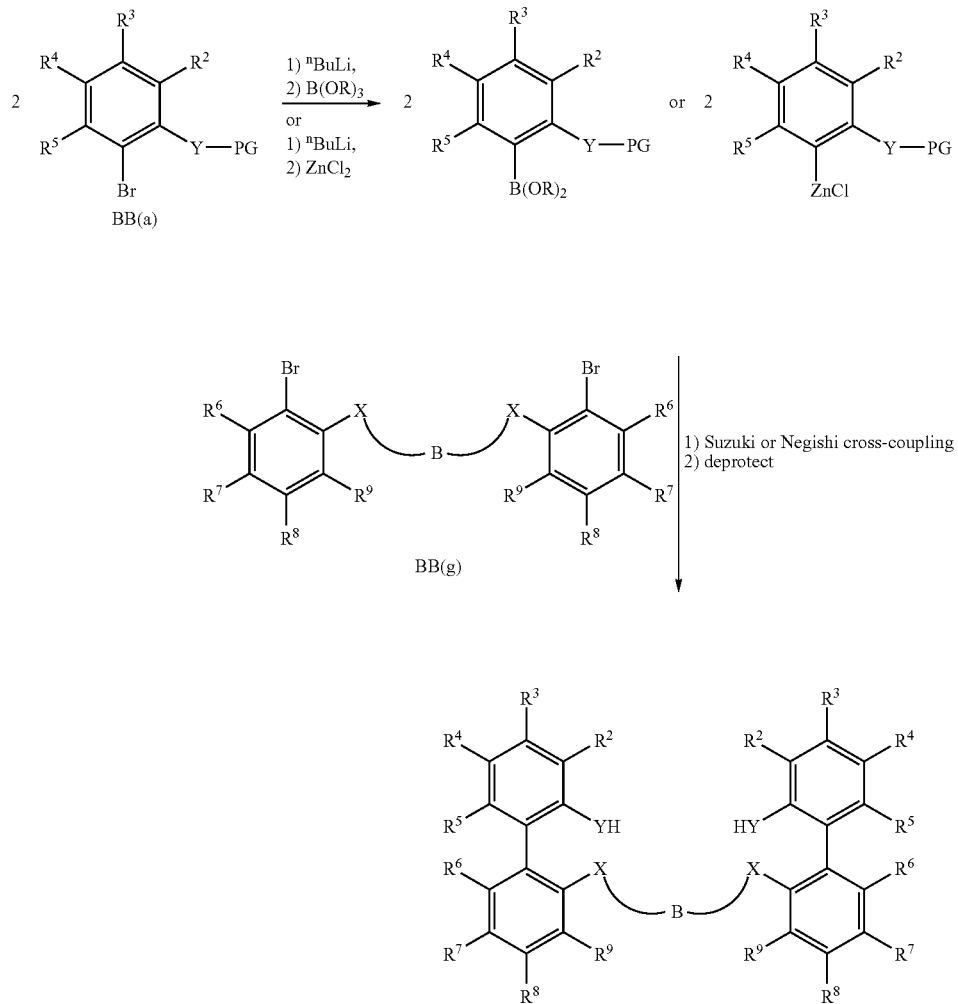

In scheme 11, the variables are defined as discussed above.

Scheme 12 below is a general scheme for the conversion of building block BB(a) to a boronic ester or ZnCl derivative, followed by double cross-coupling with building block BB(j) and subsequent deprotection:

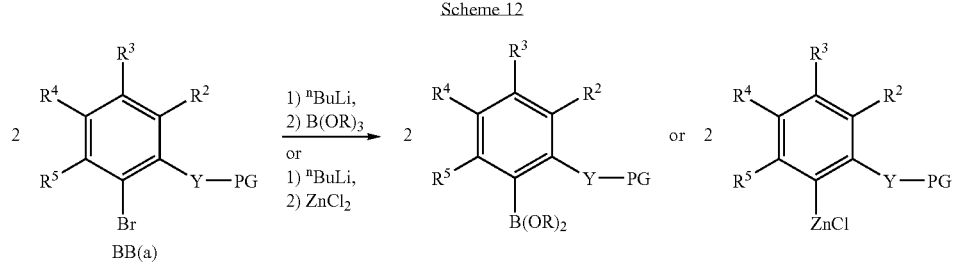

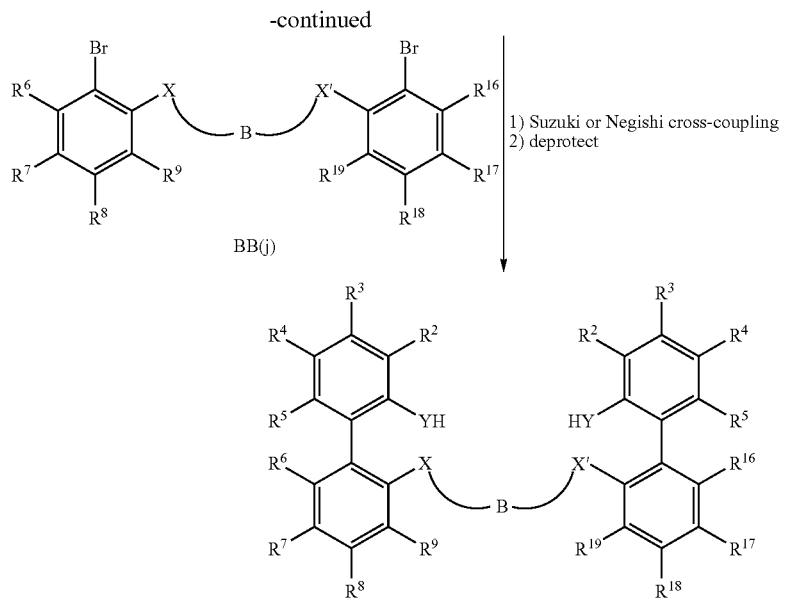
BB(j)
In scheme 12, the variables are defined as discussed above.
Scheme 13 below is a general scheme for the double cross-coupling of building blocks BB(h) or BB(i) with building block BB(a), followed by deprotection:
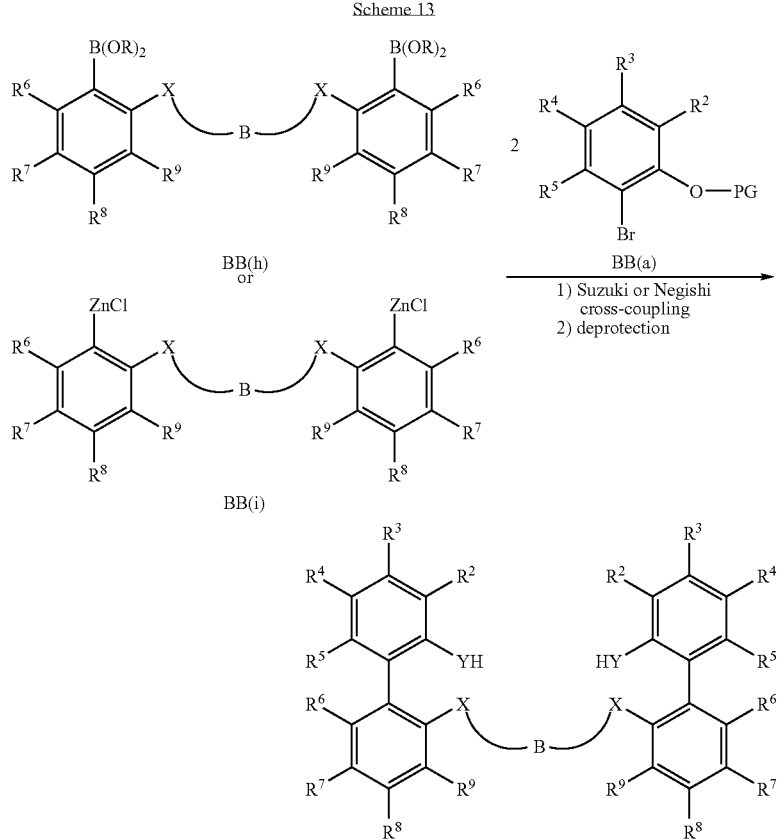
In scheme 13, the variables are defined as discussed above.

Scheme 14 below is a general scheme for the double cross-coupling of building blocks BB(k) or BB(l) with building block BB(a), followed by deprotection:
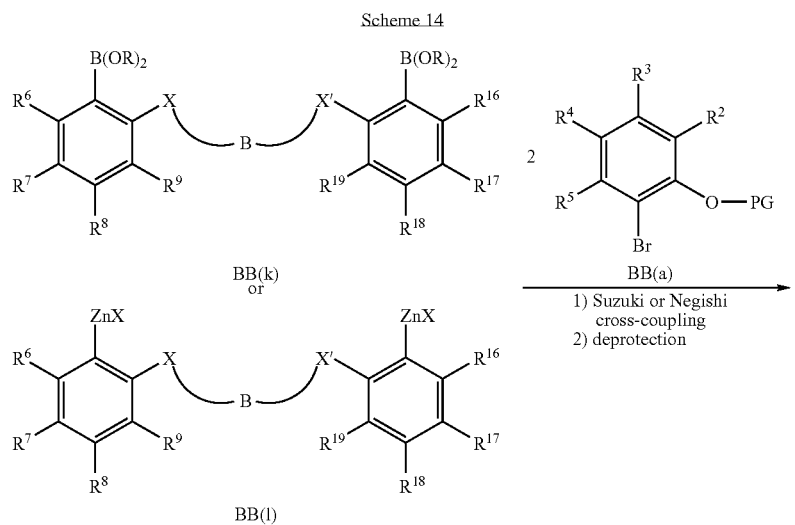
In scheme 14, the variables are defined as discussed above.
Scheme 15 below is a general scheme for the double cross-coupling of building block BB(m), followed by deprotection:
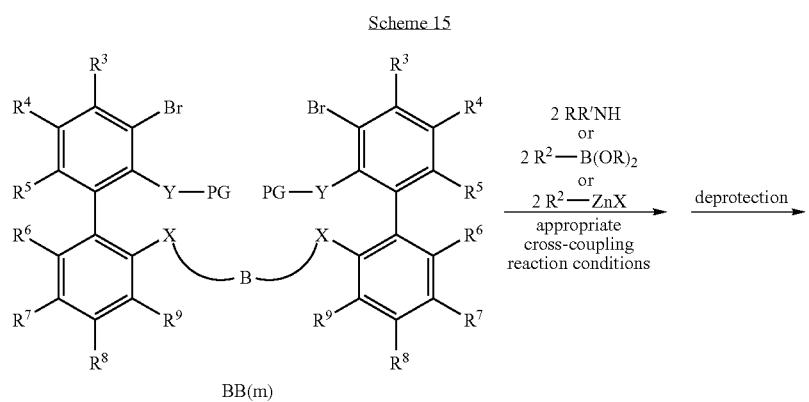

-continued
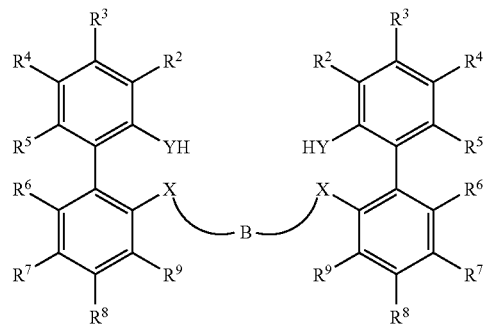
In scheme 15, the variables are defined as discussed above.
Scheme 16 below is a general scheme for the double cross-coupling of building block BB(n), followed by deprotection:
Scheme 16
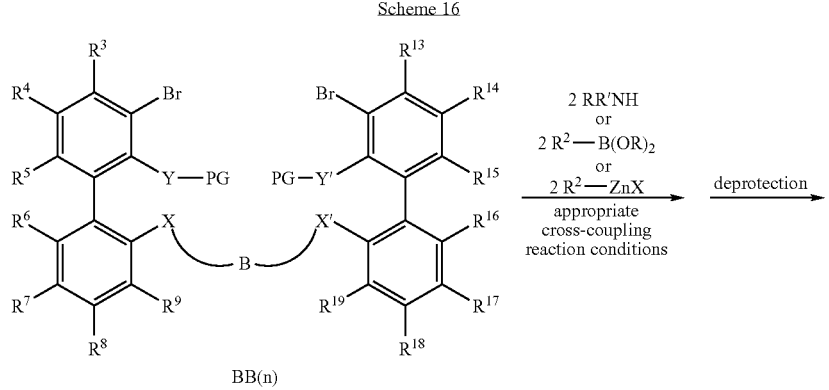
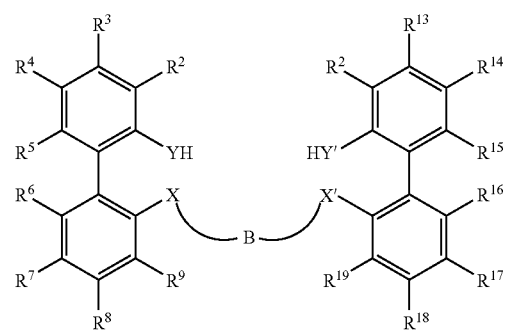
In scheme 16, the variables are defined as discussed above.

Scheme 17 below is a general scheme for the conversion of building block BB(m) into a B(OR)$_2$ or ZnX derivative, followed by double cross-coupling and deprotection:
Scheme 17
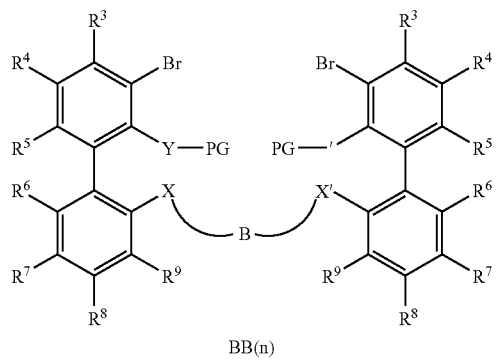
BB(n)
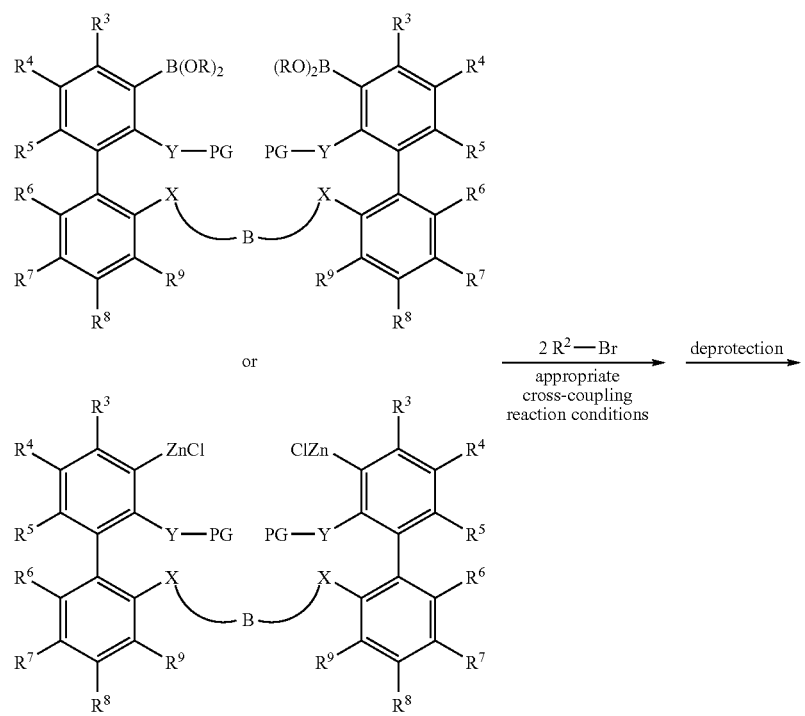
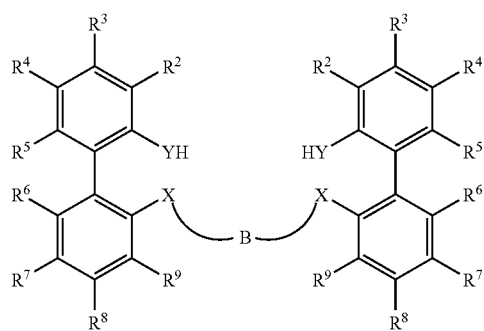

Scheme 18 below is a general scheme for the conversion of building block BB(n) into a B(OR)$_2$ or ZnX derivative, followed by double cross-coupling and deprotection:

or reacted with an activator (described below) prior to combination or reaction with the ancillary ligand. In some applications, the ligands of this invention will be combined

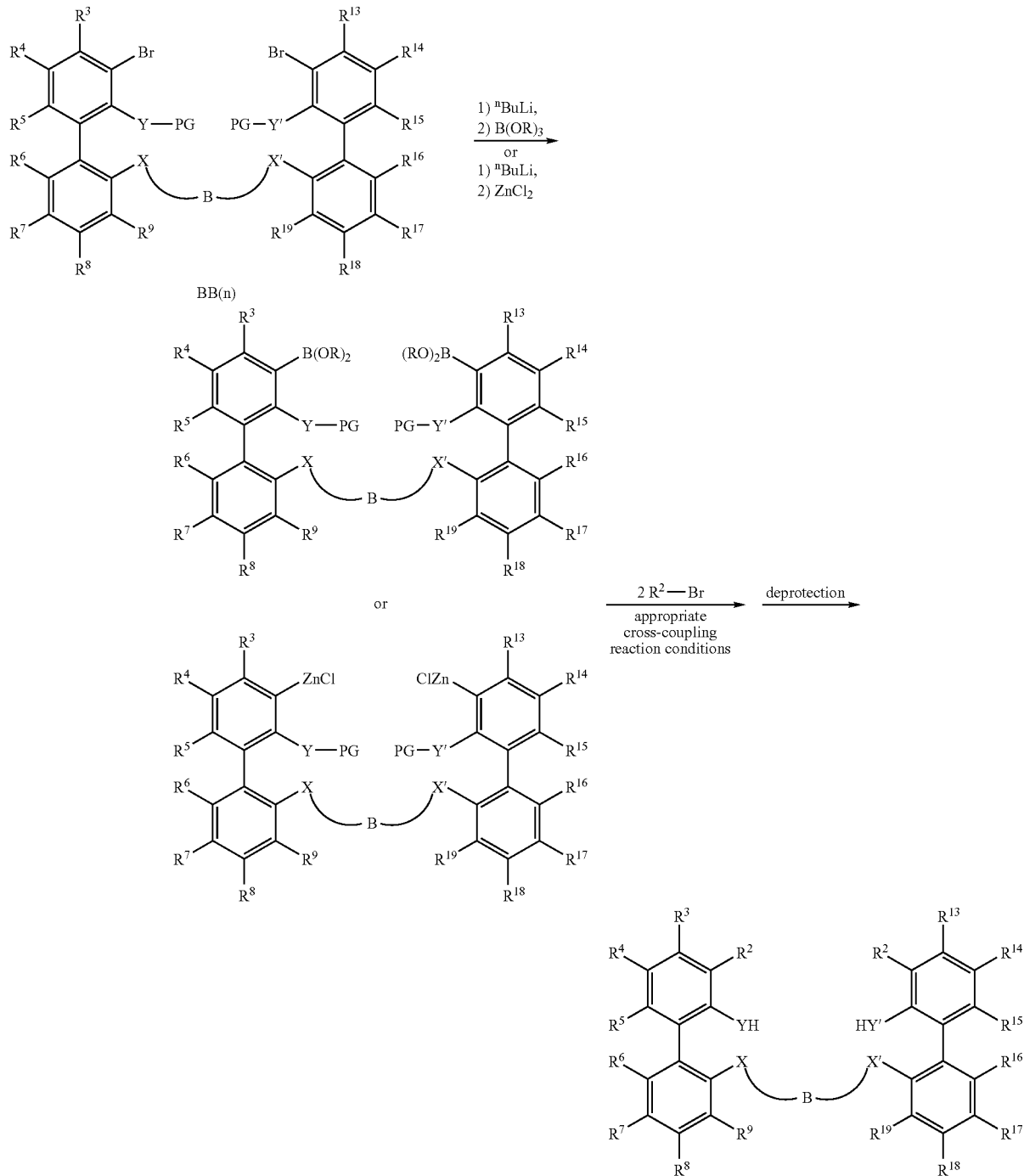

Once the desired ligand is formed, it may be combined with a metal atom, ion, compound or other metal precursor compound. For example, in some embodiments, the metal precursors are activated metal precursors, which refers to a metal precursor (described below) that has been combined with a metal compound or precursor and the product of such combination is not determined, if a product forms. For example, the ligand may be added to a reaction vessel at the same time as the metal or metal precursor compound along with the reactants, activators, scavengers, etc. Additionally, the ligand can be modified prior to addition to or after the addition of the metal precursor, e.g. through a deprotonation reaction or some other modification.

For formulas I, II, III, IV and V, the metal precursor compounds may be characterized by the general formula $M(L)_n$ where M is a metal selected from the group consisting of groups 3–6 and Lanthanide elements of the Periodic Table of Elements, more specifically, from group 4 (Hf, Zr and Ti); L is independently selected from the group consisting of halide (F, Cl, Br, I), optionally substituted alkyl, alkenyl, alkynyl, heteroalkyl, heteroalkenyl, heteroalkynyl, aryl, heteroaryl, alkoxyl, aryloxyl, silyl, boryl, phosphino, amino, thioxy, alkylthio, arylthio, hydrido, allyl, diene, phosphine, carboxylates, 1,3-dionates, oxalates, carbonates, nitrates, sulphates, ethers, thioethers and combinations thereof; L may also be ionically bonded to the metal M and for example, L may be a non-coordinated or loosely coordinated or weakly coordinated anion (e.g., L may be selected from the group consisting of those anions described below in the conjunction with the activators), see Marks et al., Chem. Rev. 2000, 100, 1391–1434 for a detailed discussion of these weak interactions; and optionally two or more L groups may be linked together in a ring structure. n is 1, 2, 3, 4, 5, or 6. The metal precursors may be monomeric, dimeric or higher orders thereof. Specific examples of suitable titanium, hafnium and zirconium precursors include, but are not limited to $TiCl_4$, $Ti(CH_2Ph)_4$, $Ti(CH_2CMe_3)_4$, $Ti(CH_2SiMe_3)_4$, $Ti(CH_2Ph)_3Cl$, $Ti(CH_2CMe_3)_3Cl$, $Ti(CH_2SiMe_3)_3Cl$, $Ti(CH_2Ph)_2Cl_2$, $Ti(CH_2CMe_3)_2Cl_2$, $Ti(CH_2SiMe_3)_2Cl_2$, $Ti(NMe_2)_4$, $Ti(NEt_2)_4$, Ti(O-isopropyl)$_4$, and $Ti(N(SiMe_3)_2)_2Cl_2$; $HfCl_4$, $Hf(CH_2Ph)_4$, $Hf(CH_2CMe_3)_4$, $Hf(CH_2SiMe_3)_4$, $Hf(CH_2Ph)_3Cl$, $Hf(CH_2CMe_3)_3Cl$, $Hf(CH_2SiMe_3)_3Cl$, $Hf(CH_2Ph)_2Cl_2$, $Hf(CH_2CMe_3)_2Cl_2$, $Hf(CH_2SiMe_3)_2Cl_2$, $Hf(NMe_2)_4$, $Hf(NEt_2)_4$, and $Hf(N(SiMe_3)_2)_2Cl_2$; $ZrCl_4$, $Zr(CH_2Ph)_4$, $Zr(CH_2CMe_3)_4$, $Zr(CH_2SiMe_3)_4$, $Zr(CH_2Ph)_3Cl$, $Zr(CH_2CMe_3)_3Cl$, $Zr(CH_2SiMe_3)_3Cl$, $Zr(CH_2Ph)_2Cl_2$, $Zr(CH_2CMe_3)_2Cl_2$, $Zr(CH_2SiMe_3)_2Cl_2$, $Zr(NMe_2)_4$, $Zr(NEt_2)_4$, $Zr(NMe_2)_2Cl_2$, $Zr(NEt_2)_2Cl_2$, and $Zr(N(SiMe_3)_2)_2Cl_2$. Lewis base adducts of these examples are also suitable as metal precursors, for example, ethers, amines, thioethers, phosphines and the like are suitable as Lewis bases. Specific examples include $HfCl_4(THF)_2$, $HfCl_4(SMe_2)_2$ and $Hf(CH_2Ph)_2Cl_2(OEt_2)$. Activated metal precursors may be ionic or zwitterionic compounds, such as $(M(CH_2Ph)_3^+)(B(C_6F_5)_4^-)$ or $(M(CH_2Ph)_3^+)(PhCH_2B(C_6F_5)_3^-)$ where M is defined above (and more specifically Hf or Zr). Activated metal precursors or such ionic compounds can be prepared in the manner shown in Pellecchia et al., Organometallics, 1994, 13, 298–302; Pellecchia et al., J. Am. Chem. Soc., 1993, 115, 1160–1162; Pellecchia et al., Organometallics, 1993, 13, 3773–3775 and Bochmann et al., Organometallics, 1993, 12, 633–640, each of which is incorporated herein by reference.

The ligand to metal precursor compound ratio is typically in the range of about 0.01:1 to about 100:1, more specifically in the range of about 0.1:1 to about 10:1 and even more specifically about 1:1.

This invention, in part, relates to new metal-ligand complexes. Generally, the ligand is mixed with a suitable metal precursor (and optionally other components, such as activators) prior to or simultaneously with allowing the mixture to be contacted with the reactants (e.g., monomers). When the ligand is mixed with the metal precursor compound, a metal-ligand complex may be formed, which may be a catalyst or may need to be activated to be a catalyst.

The metal-ligand complexes of this invention can in general be characterized in overlapping or alterative descriptions. In one embodiment, the metal-ligand complexes have dianionic, chelating ligands that may occupy up to four coordination sites of the metal atom. The metal-ligand complexes can also be described as having dianionic ligands that form two seven-member metallocycles with the metal atom (counting the metal atom as one member of the seven member ring). Also, in some embodiments, the metal-ligand complexes can be described as having dianionic, chelating ligands that use oxygen and/or sulfur as binding atoms to the metal atom. In still other embodiments, the metal-ligand complexes can be described as having non-metallocene ligands that can coordinate in an approximate $C_2$ symmetric complex with the metal atom. By approximate $C_2$ symmetry it is meant that coordination of the ligand with the metal may still be considered so that the ligand parts occupy four approximately $C_2$ symmetric quadrants around the metal center extending towards the ligands L and approximate means that true symmetry may not exist due to several factors that effect symmetry, including, for example, the effect of the bridge. In particular, the bulky $R^2$ and/or $R^{12}$ group the ligand may be approximately $C_2$ symmetrically arranged around the metal center. FIGS. 1a and 1b demonstrate what is meant herein by approximate $C_2$ symmetry. Also, this approximate symmetry can be determined by proton NMR.

In some embodiments, the metal-ligand complexes of this invention can be characterized by the general formula:

$$(4,2,O,S)ML_{n'} \qquad (VI)$$

where (4,2,O,S) is a dianionic ligand having at least 4 atoms that are each independently oxygen or sulfur and chelating to the metal M at 4 coordination sites through oxygen and/or sulfur atoms with two of the bonds between the oxygen or sulfur atoms and the metal being covelent in nature and two of the bonds being dative in nature (i.e., oxygen or sulfur atoms acting as Lewis bases and the metal center acting as a Lewis acid); M is a metal selected from the group consisting of groups 3–6 and Lanthanide elements of the Periodic Table of Elements, more specifically, from group 4 (Hf, Zr and Ti); L is independently selected from the group consisting of halide (F, Cl, Br, I), optionally substituted alkyl, alkenyl, alkynyl, heteroalkyl, heteroalkenyl, heteroalkynyl, aryl, heteroaryl, alkoxyl, aryloxyl, silyl, boryl, phosphino, amino, thioxy, alkylthio, arylthio, nitro, hydrido, allyl, diene, phosphine, carboxylates, 1,3-dionates, oxalates, carbonates, nitrates, sulphates, ethers, thioethers and combinations thereof; and optionally two or more L groups may be linked together in a ring structure; n' is 1, 2, 3, or 4.

In other embodiments, the metal-ligand complexes of this invention are those comprising two seven-member metallocycles formed with bonds from the metal atom to at least 2 heteroatoms (e.g., O, S, N, P, Se and the like). In more specific forms, these metal-ligand complexes comprise two seven-member metallocycles and even more specifically, there are at least two seven-member metallocycles that are joined together by at least one bridging group. In still other embodiments, two, bridged seven-member metallocycles form a symmetrical complex. Thus for example, the metal-ligand complex below is one embodiment of this invention:

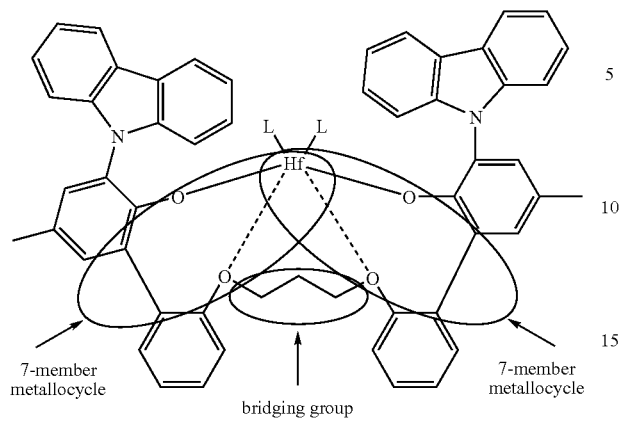

where the complex includes two metallocycles bound by a single bridging group.

In still other embodiments, the metal-ligand complexes of this invention may be characterized by the general formulas:

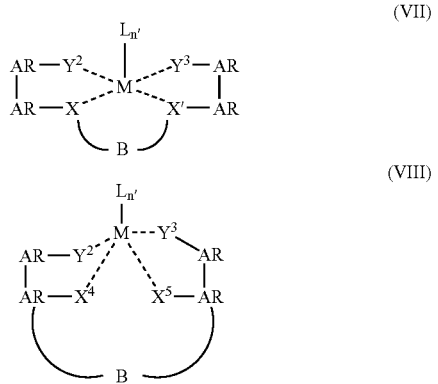

wherein each of AR, M, L, B, and n', are as defined above; and the dotted lines indicate possible binding to the metal atom, provided that at least two of the dotted lines are covalent bonds. X, X', $X^4$, $X^5$, $Y^2$ and $Y^3$ are derived from the definitions detailed above in that at least two hydrogen atoms are removed from X, X', X", X''', Y and Y', in a manner known to those of skill in the art, to form the at least two covalent bonds between the X and/or Y moieties and the metal. Depending on the number of covalent bonds, as those of skill in the art can determine, in some embodiments, X and X' and $Y^2$ and $Y^3$ are the same or different and are independently selected from the group consisting of oxygen, sulfur, —$NR^{30}$—, and —$PR^{30}$—, where $R^{30}$ is selected from the group consisting of hydride, halide, and optionally substituted hydrocarbyl, heteroatom-containing hydrocarbyl, silyl, boryl, alkoxy, aryloxy and combinations thereof. In other embodiments, $Y^2$ and $Y^3$ are the same or different and are independently selected from the group consisting of optionally substituted amino, phosphino, hydroxy, alkoxy, aryloxy, thioxy, alkylthio and arylthio. In some embodiments, $X^4$ and $X^5$ are the same or different and are independently selected from the group consisting of optionally substituted amino, phosphino, hydroxy, alkoxy, aryloxy, thioxy, alkylthio and arylthio, provided that when the bond to the metal is covalent $X^4$ and $X^5$ are independently selected from the group consisting of oxygen, sulfur, —$NR^{30}$—, and —$PR^{30}$—. Note also that $L_{n'}$ indicates that the metal M is bonded to a number n' groups of L, as defined above.

In still other embodiments, the metal-ligand complexes of this invention may be characterized by the general formula:

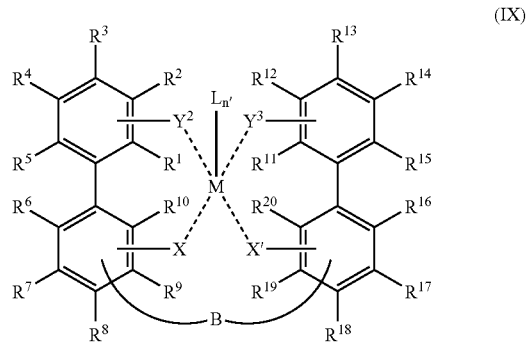

wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, M, L, n', B, X, X', $Y^2$ and $Y^3$ are as defined above and as further explained in connection which structures (VII) and (VIII). The dotted lines indicate possible binding to the metal atom, provided that at least two of the dotted lines are covalent bonds.

In still other embodiments, the metal-ligand complexes of this invention may be characterized by the general formula:

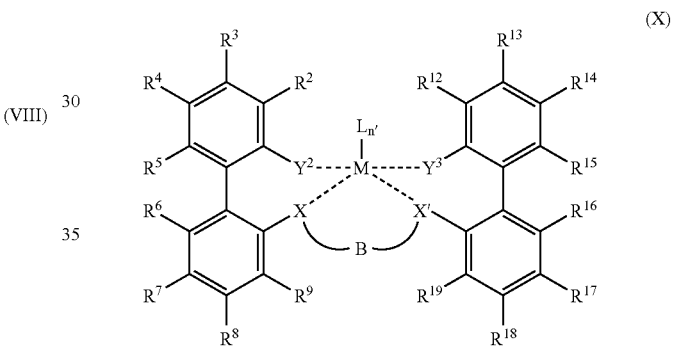

wherein $R^2$, $R^3$, $R^4$, $R^5$, $R^6$, $R^7$, $R^8$, $R^9$, $R^{12}$, $R^{13}$, $R^{14}$, $R^{15}$, $R^{16}$, $R^{17}$, $R^{18}$, $R^{19}$, M, L, n', B, X, X', $Y^2$ and $Y^3$ are as defined above are as defined above and as further explained in connection which structures (VII) and (VIII). The dotted lines indicate possible binding to the metal atom, provided that at least two of the dotted lines are covalent bonds.

In more specific embodiments, the the metal-ligand complexes of this invention may be characterized by the general formula:

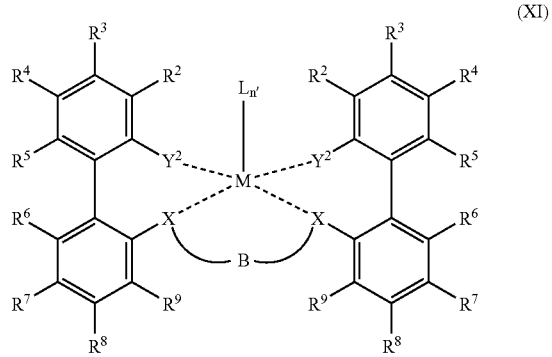

wherein $R^2$, $R^3$, $R^4$, $R^5$, $R^6$, $R^7$, $R^8$, $R^9$, M, L, n', B, X, X', and $Y^2$ are as defined above are as defined above and as further explained in connection which structures (VII) and (VIII). The dotted lines indicate possible binding to the metal atom, provided that at least two of the dotted lines are covalent bonds. In formula (XI), the metal-ligand complex may also have approximate $C_2$ symmetry that may provide control of tacticity in the polymerization of propylene to isotactic polypropylene, when combined with appropriate activator(s).

In addition, specifics for the substituents on the ligands for production of the particular polymers discussed above (e.g., isotactic polypropylene) apply to the metal-ligand complexes. In addition, Lewis base adducts of the metal-ligand complexes in the above formulas are also suitable, for example, ethers, amines, thioethers, phosphines and the like are suitable as Lewis bases. The metal-ligand complexes can be formed by techniques known to those of skill in the art, such as combinations of metal precursors and ligands under conditions to afford complexation. For example, the complexes of this invention can be prepared according to the general scheme shown below:

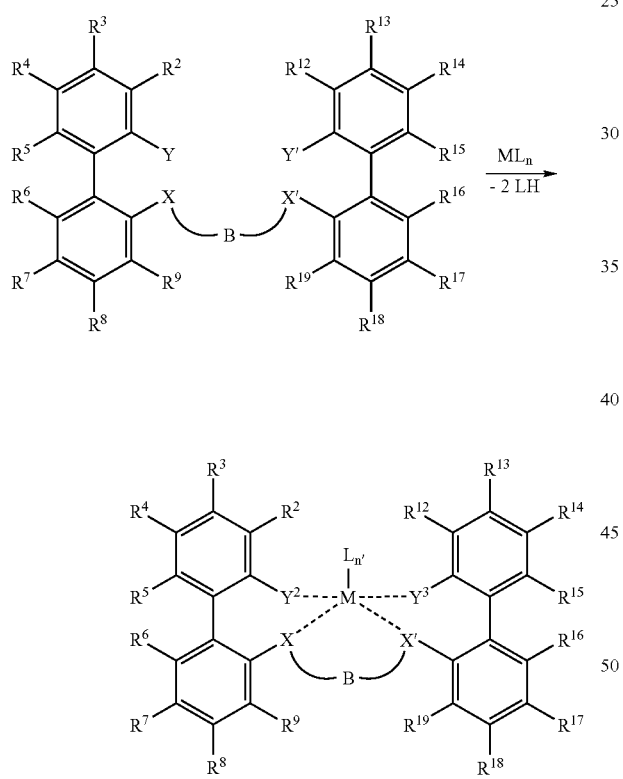

As shown in Scheme 16, a ligand according to formula (IV) is combined with the metal precursor under conditions to cause the removal of at least 2 leaving group ligands L, which are shown in the scheme as combining with a hydrogen (H). Other schemes where the leaving group ligand combines with other moieties (e.g., Li) employing other known routes for complexation may be used, including for example, reactions where the ligand L reacts with other moieties (e.g., where the alkali metal salt of the ligand is used and the complexation reaction proceeds by salt elimation).

Specific metal-ligand complexes with approximate $C_2$ symmetry within the scope of the invention include:

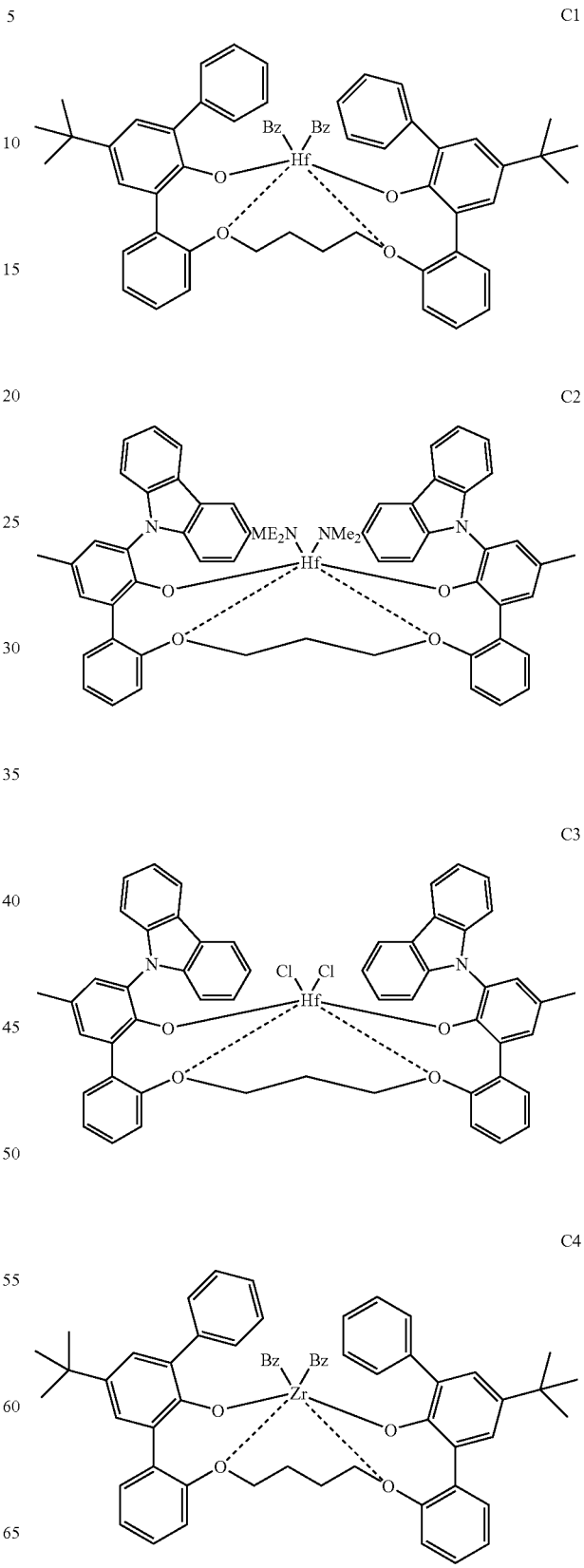

-continued

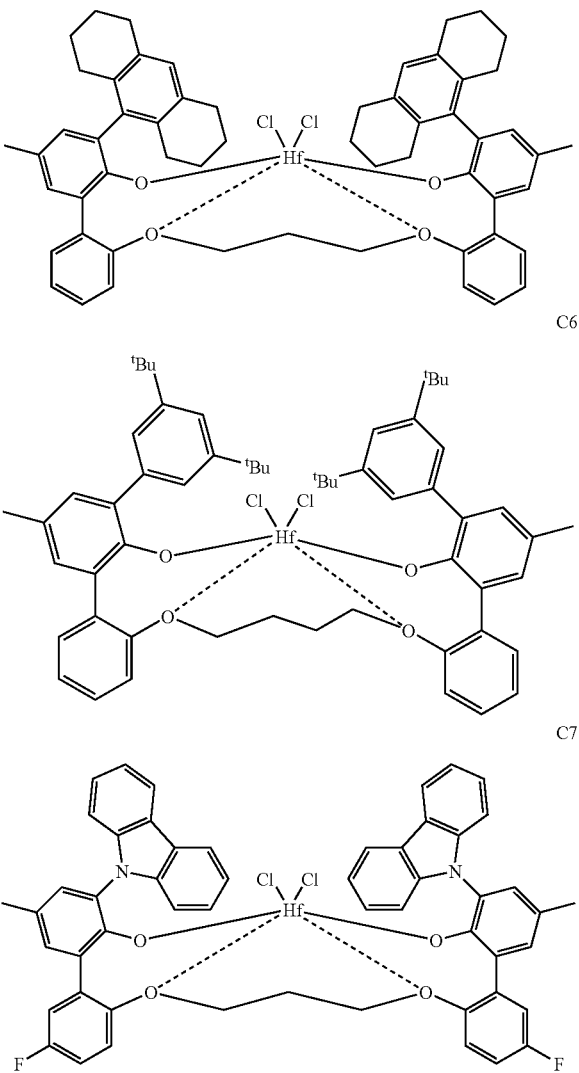

C5

C6

C7

The x-ray crystal structure of molecule C5 is shown in FIGS. 1a and 1b.

The ligands, complexes or catalysts may be supported on organic or inorganic supports. Suitable supports include silicas, aluminas, clays, zeolites, magnesium chloride, polystyrenes, substituted polystyrenes and the like. Polymeric supports may be cross-linked or not. Similarly, the ligands, complexes or catalysts may be supported on similar supports known to those of skill in the art. See for example, Hlatky, Chem. Rev. 2000, 100, 1347–1376 and Fink et al., Chem. Rev. 2000, 100, 1377–1390, both of which are incorporated herein by reference. In addition, the catalysts of this invention may be combined with other catalysts in a single reactor and/or employed in a series of reactors (parallel or serial) in order to form blends of polymer products.

The metal-ligand complexes and compositions are active catalysts typically in combination with a suitable activator, combination of activators, activating technique or activating package, although some of the ligand-metal complexes may be active without an activator or activating technique. Broadly, the activator(s) may comprise alumoxanes, Lewis acids, Bronsted acids, compatible non-interfering activators and combinations of the foregoing. These types of activators have been taught for use with different compositions or metal complexes in the following references, which are hereby incorporated by reference in their entirety: U.S. Pat. Nos. 5,599,761, 5,616,664, 5,453,410, 5,153,157, 5,064,802, EP-A-277,004 and Marks et al., Chem. Rev. 2000, 100, 1391–1434. In particular, ionic or ion forming activators are preferred.

Suitable ion forming compounds useful as an activator in one embodiment of the present invention comprise a cation that is a Bronsted acid capable of donating a proton, and an inert, compatible, non-interfering, anion, $A^-$. Preferred anions are those containing a single coordination complex comprising a charge-bearing metal or metalloid core. Mechanistically, said anion should be sufficiently labile to be displaced by olefinic, diolefinic and unsaturated compounds or other neutral Lewis bases such as ethers or nitriles. Suitable metals include, but are not limited to, aluminum, gold and platinum. Suitable metalloids include, but are not limited to, boron, phosphorus, and silicon. Compounds containing anions that comprise coordination complexes containing a single metal or metalloid atom are, of course, well known and many, particularly such compounds containing a single boron atom in the anion portion are available commercially.

Specifically such activators may be represented by the following general formula:

$$(L^*\text{-H})_d^+(A^{d-})$$

wherein $L^*$ is a neutral Lewis base; $(L^*\text{-H})^+$ is a Bronsted acid; $A^{d-}$ is a non-interfering, compatible anion having a charge of d–, and d is an integer from 1 to 3. More specifically $A^{d-}$ corresponds to the formula: $(M'^{3+} Q_h)^{d-}$ wherein h is an integer from 4 to 6; h–3=d; M' is an element selected from Group 13 of the Periodic Table of the Elements; and Q is independently selected from the group consisting of hydride, dialkylamido, halide, alkoxide, aryloxide, hydrocarbyl, and substituted-hydrocarbyl radicals (including halide substituted hydrocarbyl, such as perhalogenated hydrocarbyl radicals), said Q having up to 20 carbons. In a more specified embodiment, d is one, i.e., the counter ion has a single negative charge and corresponds to the formula $A^-$.

Activators comprising boron or aluminum which are particularly useful in the preparation of catalysts of this invention may be represented by the following general formula:

$$(L^*\text{-H})^+(JQ_4)^-$$

wherein: $L^*$ is as previously defined; J is boron or aluminum; and Q is a fluorinated $C_{1-20}$ hydrocarbyl group. Most specifically, Q is independently selected from the group selected from the group consisting of fluorinated aryl group, especially, a pentafluorophenyl group (i.e., a $C_6F_5$ group) or a 3,5-bis$(CF_3)_2C_6H_3$ group. Illustrative, but not limiting, examples of boron compounds which may be used as an activating cocatalyst in the preparation of the improved catalysts of this invention are tri-substituted ammonium salts such as: trimethylammonium tetraphenylborate, triethylammonium tetraphenylborate, tripropylammonium tetraphenylborate, tri(n-butyl)ammonium tetraphenylborate, tri(t-butyl)ammonium tetraphenylborate, N,N-dimethylanilinium tetraphenylborate, N,N-diethylanilinium tetraphenylborate, N,N-dimethylanilinium tetra-(3,5-bis(trifluoromethyl)phenyl)borate, N,N-dimethyl-(2,4,6-trimethylanilinium)tetraphenylborate, trimethylammonium tetrakis (pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(secbutyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium)tetrakis(pentafluorophenyl)borate, trimethylammonium tetrakis-(2,3,4,6-tetrafluorophenylborate and N,N-dimethylanilinium tetrakis-(2,3,4,6-tetrafluorophenyl)borate; dialkyl ammonium salts such as: di-(i-propyl)ammonium tetrakis(pentafluorophenyl)borate, and dicyclohexylammonium tetrakis(pentafluorophenyl)borate; and tri-substituted phosphonium salts such as: triphenylphospnonium tetrakis(pentafluorophenyl)borate, tri(o-tolyl)phosphonium tetrakis(pentafluorophenyl)borate, and tri(2,6-dimethylphenyl)phosphonium tetrakis(pentafluorophenyl)borate; N,N-dimethylanilinium tetrakis(3,5-bis(trifluoromethyl)phenyl)borate; $HNMe(C_{18}H_{37})^+B(C_6F_5)_4^-$; $HNPh(C_{18}H_{37})^+B(C_6F_5)_4^-$ and $((4\text{-nBu-Ph})NH(n\text{-hexyl})_2)^+B(C_6F_5)_4^-$. Specific $(L^*\text{-H})^+$ cations are N,N-dimethylanilinium and $HNMe(C_{18}H_{37})^+$. Specified anions are tetrakis(3,5-bis(trifluoromethyl)phenyl)borate and tetrakis(pentafluorophenyl)borate. In some embodiments, the specific activator is $PhNMe_2H^+B(C_6F_5)_4^-$.

Other suitable ion forming activators comprise a salt of a cationic oxidizing agent and a non-interfering, compatible anion represented by the formula:

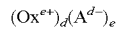

$$(Ox^{e+})_d(A^{d-})_e$$

wherein: $Ox^{e+}$ is a cationic oxidizing agent having a charge of e+; e is an integer from 1 to 3; and $A^{d-}$, and d are as previously defined. Examples of cationic oxidizing agents include: ferrocenium, hydrocarbyl-substituted ferrocenium, $Ag^+$, or $Pb^{+2}$. Specific embodiments of $A^{d-}$ are those anions previously defined with respect to the Bronsted acid containing activating cocatalysts, especially tetrakis(pentafluorophenyl)borate.

Another suitable ion forming, activating cocatalyst comprises a compound that is a salt of a carbenium ion or silyl cation and a non-interfering, compatible anion represented by the formula:

$$\copyright^+A^-$$

wherein: $\copyright^+$ is a $C_{1-100}$ carbenium ion or silyl cation; and $A^-$ is as previously defined. A preferred carbenium ion is the trityl cation, i.e. triphenylcarbenium. The silyl cation may be characterized by the formula $Z^4Z^5Z^6Si^+$ cation, where each of $Z^4$, $Z^5$, and $Z^6$ is independently selected from the group consisting of hydride, halide, and optionally substituted alkyl, alkenyl, alkynyl, heteroalkyl, heteroalkenyl, heteroalkynyl, aryl, heteroaryl, alkoxyl, aryloxyl, silyl, boryl, phosphino, amino, thioxy, alkylthio, arylthio, and combinations thereof. In some embodiments, a specified activator is $Ph_3C^+B(C_6F_5)_4^-$.

Other suitable activating cocatalysts comprise a compound that is a salt, which is represented by the formula $(A^{*+a})_b(Z^*J^*_j)^{-c}_d$ wherein $A^*$ is a cation of charge +a; $Z^*$ is an anion group of from 1 to 50, specifically 1 to 30 atoms, not counting hydrogen atoms, further containing two or more Lewis base sites; $J^*$ independently each occurrence is a Lewis acid coordinated to at least one Lewis base site of $Z^*$, and optionally two or more such $J^*$ groups may be joined together in a moiety having multiple Lewis acidic functionality; j is a number form 2 to 12; and a, b, c, and d are integers from 1 to 3, with the proviso that a×b is equal to c×d. See, WO 99/42467, which is incorporated herein by reference. In other embodiments, the anion portion of these activating cocatalysts may be characterized by the formula $((C_6F_5)_3M'''\text{-LN-}M''''(C_6F_5)_3)^-$ where $M''''$ is boron or aluminum and LN is a linking group, which is specifically selected from the group consisting of cyanide, azide, dicyanamide and imidazolide. The cation portion is specifically a quaternary amine. See, e.g., LaPointe, et al., *J. Am. Chem. Soc.* 2000, 122, 9560–9561, which is incorporated herein by reference.

In addition, suitable activators include Lewis acids, such as those selected from the group consisting of tris(aryl)boranes, tris(substituted aryl)boranes, tris(aryl)alanes, tris(substituted aryl)alanes, including activators such as tris(pentafluorophenyl)borane. Other useful ion forming Lewis acids include those having two or more Lewis acidic sites, such as those described in WO 99/06413 or Piers, et al. "New Bifunctional Perfluoroaryl Boranes: Synthesis and Reactivity of the ortho-Phenylene-Bridged Diboranes 1,2-$(B(C_6F_5)_2)_2C_6X_4$ (X=H, F)", *J. Am. Chem. Soc.*, 1999, 121, 3244–3245, both of which are incorporated herein by reference. Other useful Lewis acids will be evident to those of skill in the art. In general, the group of Lewis acid activators is within the group of ion forming activators (although exceptions to this general rule can be found) and the group tends to exclude the group 13 reagents listed below. Combinations of ion forming activators may be used.

Other general activators or compounds useful in a polymerization reaction may be used. These compounds may be activators in some contexts, but may also serve other functions in the polymerization system, such as alkylating a metal center or scavenging impurities. These compounds are within the general definition of "activator," but are not considered herein to be ion-forming activators. These compounds include a group 13 reagent that may be characterized by the formula $G^{13}R^{50}_{3-p}D_p$ where $G^{13}$ is selected from the group consisting of B, Al, Ga, In and combinations thereof, p is 0, 1 or 2, each $R^{50}$ is independently selected from the group consisting of hydride, halide, and optionally substituted alkyl, alkenyl, alkynyl, heteroalkyl, heteroalkenyl, heteroalkynyl, aryl, heteroaryl, and combinations thereof, and each D is independently selected from the group consisting of halide, hydride, alkoxy, aryloxy, amino, thioxy, alkylthio, arylthio, phosphino and combinations thereof. In other embodiments, the group 13 activator is an oligomeric or polymeric alumoxane compound, such as methylalumoxane and the known modifications thereof. In other embodiments, a divalent metal reagent may be used that is defined by the general formula $M'R^{50}_{2-p'}D_{p'}$ and p' is 0 or 1 in this embodiment and $R^{50}$ and D are as defined above. M' is the metal and is selected from the group consisting of Mg, Ca, Sr, Ba, Zn, Cd and combinations thereof. In still other embodiments, an alkali metal reagent may be used that is defined by the general formula $M''R^{50}$ and in this embodiment $R^{50}$ is as defined above. M'' is the alkali metal and is selected from the group consisting of Li, Na, K, Rb, Cs and combinations thereof. Additionally, hydrogen and/or silanes may be used in the catalytic composition or added to the polymerization system. Silanes may be characterized by the formula $SiR^{50}_{4-q}D_q$ where $R^{50}$ is defined as above, q is 1, 2, 3 or 4 and D is as defined above, with the proviso that there is at least one D that is a hydride.

The molar ratio of metal:activator (whether a composition or complex is employed as a catalyst) employed specifically ranges from 1:10,000 to 100:1, more specifically from 1:5000 to 10:1, most specifically from 1:10 to 1:1. In one embodiment of the invention mixtures of the above compounds are used, particularly a combination of a group 13 reagent and an ion-forming activator. The molar ratio of group 13 reagent to ion-forming activator is specifically from 1:10,000 to 1000:1, more specifically from 1:5000 to 100:1, most specifically from 1:100 to 100:1. In another embodiment, the ion forming activators are combined with a group 13 reagent. Another embodiment is a combination of the above compounds having about 1 equivalent of N,N-dimethylanilinium tetrakis(pentafluorophenyl)borate, and 5–30 equivalents of a Group 13 reagent.

In other applications, the ligand will be mixed with a suitable metal precursor compound prior to or simultaneous with allowing the mixture to be contacted to the reactants. When the ligand is mixed with the metal precursor compound, a metal-ligand complex may be formed, which may be a catalyst.

The compositions, complexes and/or catalysts of this invention are particularly effective at polymerizing α-olefins (such as propylene, 1-butene, 1-pentene, 1-hexene, 1-heptene, 1-octene, and styrene), copolymerizing ethylene with α-olefins (such as propylene, 1-butene, 1-pentene, 1-hexene, 1-heptene, 1-octene, and styrene), and copolymerizing ethylene with 1,1-disubstituted olefins (such as isobutylene). These compositions might also polymerize monomers that have polar functionalities in homopolymerizations or copolymerizations and/or homopolymerize 1,1- and 1,2-disubstituted olefins. Also, diolefins in combination with ethylene and/or α-olefins or 1,1- and 1,2-disubstituted olefins may be copolymerized.

In general monomers useful herein may be olefinically or unsaturated monomers having from 2 to 20 carbon atoms either alone or in combination. Generally, monomers may include olefins, diolefins and unsaturated monomers including ethylene and $C_3$ to $C_{20}$ α-olefins such as propylene, 1-butene, 1-hexene, 1-octene, 4-methyl-1-pentene, 1-norbornene, styrene and mixtures thereof, additionally, 1,1-disubstituted olefins, such as isobutylene, 2-methyl-1-butene, 2-methyl-1-pentene, 2-ethyl-1-pentene, 2-methyl-1-hexene, 3-trimethylsilyl-2-methyl-1-propene, α-methyl-styrene, either alone or with other monomers such as ethylene or $C_3$ to $C_{20}$ α-olefins and/or diolefins; additionally 1,2-substituted olefins, such as 2-butene. The α-olefins listed above may be polymerized in a stereospecific manner e.g. to generate isotactic or syndiotactic or hemiisotactic polypropylene. Additionally the α-olefins may be polymerized to produce a polymer with differing tacticity sequences within the polymer chain, such as polypropylene containing atactic and isotactic sequences within the same polymer chain. These definitions are intended to include cyclic olefins. Diolefins generally comprise 1,3-dienes such as (butadiene), substituted 1,3-dienes (such as isoprene) and other substituted 1,3-dienes, with the term substituted referring to the same types of substituents referred to above in the definition section. Diolefins also comprises 1,5-dienes and other non-conjugated dienes. The styrene monomers may be unsubstituted or substituted at one or more positions on the aryl ring. The use of diolefins in this invention is typically in conjunction with another monomer that is not a diolefin. In some embodiments, acetylenically unsaturated monomers may be employed.

More specifically, it has been found that the catalysts of the present invention are particularly active for certain monomers, particularly (X-olefins. Thus, the catalysts of the present invention may provide higher comonomer incorporation for copolymers of ethylene and co-monomers having three or more carbon atoms than is currently known from other catalysts. It has been found that particular catalysts of the present invention co-polymerize ethylene and styrene (or substituted styrenes), forming ethylene-styrene copolymers. Polymers that can be prepared according to the present invention include ethylene copolymers with at least one $C_3$–$C_{20}$ α-olefin, particularly propylene, 1-butene, 1-hexene, 4-methyl-1-pentene and 1-octene. The copolymers of ethylene with at least one $C_3$–$C_{20}$ α-olefin comprise from about 0.1 mol. % α-olefin to about 50 mol. % α-olefin, more specifically from about 0.2 mol. % α-olefin to about 50 mol. % α-olefin and still more specifically from about 2 mol. % α-olefin to about 30 mol. % higher olefin. For certain embodiments of this invention, copolymers include those of ethylene and a comonomer selected from the group consisting of propylene, 1-butene, 1-hexene, and 1-octene comprise from about 0.2 to about 30 mol. % comonomer, more specifically from about 1 to about 20 mol. % comonomer, even more specifically from about 2 to about 15 mol. % comonomer and most specifically from about 5 to about 12 mol. % comonomer.

Novel polymers, copolymers or interpolymers may be formed having unique physical and/or melt flow properties. Such novel polymers can be employed alone or with other polymers in a blend to form products that may be molded, cast, extruded or spun. End uses for the polymers made with the catalysts of this invention include films for packaging, trash bags, bottles, containers, foams, coatings, insulating devices and household items. Also, such functionalized polymers are useful as solid supports for organometallic or chemical synthesis processes.

The α-olefins listed above may be polymerized in a stereoselective manner e.g. to generate isotactic or syndiotactic or hemiisotactic poly-α-olefins. For example, 1-butene may be polymerized into isotactic poly-1-butene. Additionally the α-olefins may be polymerized to produce a polymer with differing tacticity sequences within the polymer chain, such as polypropylene containing atactic and isotactic sequences within the same polymer chain. The stereoregularity may be interrupted by stereoerrors, in particular isolated stereoerrors, which is an indication of enantiomorphic side control. Also regioerrors might be present in the isotactic polypropylene polymer as it is described in the literature (see, e.g., Resconi et al., "Selectivity in Propene Polymerization with Metallocene Catalysts," Chem. Rev. 2000, 100, 1253–1345).

More specifically, it has been found that particular catalysts of the present invention polymerize propylene to isotactic or crystalline polypropylene, forming polymers with novel properties. The combination of isotactic polypropylene properties that are obtained at higher polymerization temperatures is surprising. In particular, isotactic polypropylene can be produced having a narrow polydispersity (e.g., less than about 3.0 and more specifically less than 2.5) combined with a high molecular weight (e.g., greater than about 50,000, more specifically greater than about 100,000 and even more specifically greater than about 150,000) in a solution polymerization process at a temperature of greater than about 100° C., more specifically greater than 110° C. and even more specifically greather than 130° C. In addition the isotactic polypropylene produced by certain embodiments of this invention can be prepared with few or no detectable using $^{13}C$ NMR regio-errors (also known as regio-irrgularities). This is shown in FIG. 2 where the regio-errors are not detectable in certain isotactic polypropylene polymers prepared as discussed in the examples, using $^{13}C$ NMR methods as described in Rescnoi et al. cited above. It is intended that the $^{13}C$ NMR used herein are typical for polymer characterization.

The isotactic polypropylene polymers formed from these catalysts in a solution polymerization process can be produced at a higher temperature than has been described before, such as at a temperature of greater than about 100° C., more specifically greater than 110° C. and even more specifically greather than 130° C. The polymerization conditions are described herein, producing isotactic polypropylene with a crystallinity index of between about 0.35 and about 0.95, more specifically between about 0.65 and 0.95 and in some embodiments specifically above about 0.8, under the polymerization conditions employed. The crystallinity index is determined using FTIR as is known to those of skill in the art and calibrated based on a relative scale. In one embodiment, the crystallinity index value can be determined using commercially available FTIR equipment (such as a Bruker Equinox 55 with an IR Scope II in reflection mode using Pike MappIR software). The crystallinity index is obtained from the ratio of band heights at 995 cm$^{-1}$ and 972 cm$^{-1}$. Atactic polypropylene has a ratio of band heights or crystallinity index of 0.2. Greater than 98% isotactic polypropylene has a crystallinity index ratio of greater than 0.95. Generally, the amount of error in crystallinity index measurements is ±0.05. Polymer blends of various compositions show a linear relationship between % isotacticity and crystallinity index. See, for example, J. P. Luongo, *J. Appl. Polym. Sci.*, 3 (1960) 302–309 and T. Sundell, H. Fagerholm, H. Crozier, Polymer 37 (1996) 3227–3231, each of which is incorporated herein by reference.

As those of skill in the art will recognize, isotacticity can also be represented by percent pentads (% mmmm) as determined by $^{13}$C NMR spectroscopy. Proton decoupled $^{13}$C NMR spectroscopy can be performed using commercially available equipment (such as a Bruker 300 MHz at 100° C. probe temperature) to determine the degree of tacticity as % mmmm pentads (for assignment of $^{13}$C signals see the review Brintzinger H. H. et al., *Angew. Chem. Int. Ed. Eng.* 1995, 34, 1143, which is incorporated herein by reference; and Resconi, *Chem. Rev.* 2000, 100, 1253–1345 and Gibson, et al., *Chem Rev.* 2003, 103, 283–315). For example, a 15–30 mg polymer sample is dissolved in a 1:1 mixture of $C_2D_2Cl_4$ and $C_2Cl_4$ by heating the sample to ca. 100° C. The % mmmm is determined by the ratio of peak integral from 23.5 to 21.5 ppm and peak integral 23.5 to 19 ppm (in the absence of significant chain end regio-irregularity signals in this region). Proton decoupled $^{13}$C NMR spectroscopy can be also performed to determine the frequency of and nature of stereoerrors and regioerrors.

In addition, the melting point of the crystalline polypropylene is generally in the range of from about 115° C. to about 165° C., more specifically between about 120° C. and 155° C., and in some embodiments specifically above about 135° C. Melting points are determined by differential scanning calorimetry, as is known in the art (see also the example section, herein).

Novel polymers, copolymers or interpolymers may be formed having unique physical and/or melt flow properties. Polymers that can be prepared according to the present invention include propylene copolymers with at least one $C_4$–$C_{20}$ α-olefin, particularly 1-butene, 1-hexene, 4-methyl-1-pentene and 1-octene. The copolymers of propylene with at least one $C_4$–$C_{20}$ α-olefin comprise from about 0.1 wt. % higher olefin to about 60 wt. % higher olefin, more specifically from about 0.2 wt. % higher olefin to about 50 wt. % higher olefin and still more specifically from about 2 wt. % higher olefin to about 30 wt. % higher olefin. For certain embodiments of this invention, crystalline copolymers include those of propylene and a comonomer selected from the group consisting of ethylene, 1-butene, 1-hexene, and 1-octene comprise from about 0.2 to about 30 wt. % comonomer, more specifically from about 1 to about 20 wt. % comonomer, even more specifically from about 2 to about 15 wt. % comonomer and most specifically from about 5 to about 12 wt. % comonomer.

The novel polymers (such as isotactic polypropylene) disclosed herein can be employed alone or with other natural or synthetic polymers in a blend. Such other natural or synthetic polymers can be polyethylene (including linear low density polyethylene, low density polyethylene, high density polyethylene, etc.), atactic polypropylene, nylon, EPDM, ethylene-propylene elastomer copolymers, polystyrene (including syndiotactic polystryene), ethylene-styrene copolymers and terpolymers of ethylene-styrene and other $C_3$–$C_{20}$ olefins (such as propylene).

Melt flow rate (MRF) for polypropylene and copolymer of propylene and one or more $C_4$–$C_{20}$ α-olefins is measured according to ASTM D-1238, condition L (2.16 kg, 230° C.). In some embodiments of this invention, the MFR is in the range of 0.005–1,000, more specifically 0.01–500 and even more specifically 0.1–100. Flex modulus for polypropylene and copolymer of propylene and one or more $C_4$–$C_{20}$ α-olefins is measured according to ASTM D-790. In some embodiments of this invention, the flex modulus ranges from 20,000–400,000 psi, more specifically from 20,000–300,000 psi and even more specifically from 100,000–200,000 psi. Notch izod impact for polypropylene and copolymer of propylene and one or more $C_4$–$C_{20}$ α-olefins is measured according to ASTM D-256A. In some embodiments of this invention, the notch izod impact ranges from 0.1 to no break in ft-lbs/in.

The novel polypropylene and copolymer of propylene and one or more $C_4$–$C_{20}$ α-olefins disclosed in the present invention are useful for a wide variety of applications, including films (such as blown and cast film, clarity film and multi-layer films), thermoforming (such as cups, plates, trays and containers), injection moulding, blow-moulding, foams (such as structural foams), pipe (such as potable water pipe and high pressure pipe), automotive parts, and other applications that will be evident to those of skill in the art.

Melt strength (measured in cN) and melt drawability (measured in mm/s) tests are conducted by pulling ("taking-up") strands of the molten polymers or blends at constant acceleration until breakage occurs. An experimental set-up comprises a capillary rheometer and a Rheotens apparatus as a take-up device. The molten strands are drawn uniaxially to a set of accelerating nips located 100 mm below the die. The force required to uniaxially extend the strands is recorded as a function of the take-up velocity or the nip rolls. In the case of polymer melts exhibiting draw resonance (indicated by the onset of a periodic oscillation of increasing amplitude in the measured force profile), the maximum force and wheel velocity before the onset of draw resonance are taken as the melt strength and melt drawability, respectively. In the absence of draw resonance, the maximum force attained during testing is defined as the melt strength and the velocity at which breakage occurs is defined as the melt drawability. These tests are typically run under the following conditions:

| | |
|---|---|
| Mass flow rate | 1.35 grams/min |
| Temperature | 190° C. |
| Equilibration time at 190° C. | 10 minutes |
| Die | 20:1 (with entrance angle of approximately 45 degrees) |

-continued

| | |
|---|---|
| Capillary length | 41.9 mm |
| Capillary diameter | 2.1 mm |
| Piston diameter | 9.54 mm |
| Piston velocity | 0.423 mm/s |
| Shear rate | 33.0 s$^{-1}$ |
| Draw-down distance (die exit to take-up sheels) | 100 mm |
| Cooling conditions | Ambient air |
| Acceleration | 2.4 mm/s$^2$ |

For some aspects of the present invention the novel polymers are useful to produce foams having improved properties. For foams and other applications requiring melt strength, the MFR is typically in the range of 0.1–10, more specifically in the range of 0.3–3 and most specifically in the range of 0.5–2. The melt strength is typically greater than 5 cN, more specifically greater than 9 cN and most specifically greater than 12 cN. The drawability is typically greater than 15 mm/sec, more specifically greater than 25 mm/sec and most specifically greater than 35 mm/sec.

In some aspects of the present invention, the novel polymers disclosed herein are useful for a wide variety of applications where certain optical properties are beneficial. Gloss is measured according to ASTM D-1746. Haze is measured according to ASTM D-1003 and clarity is measured according to ASTM D-2457. The novel polymers disclosed herein in some aspects are films having haze of less than 10%. In addition films having clarity of greater than 91% may be beneficially obtained.

Polymerization is carried out under polymerization conditions, including temperatures of from −100° C. to 300° C. and pressures from atmospheric to 3000 atmospheres. Suspension, solution, slurry, gas phase or high-pressure polymerization processes may be employed with the catalysts and compounds of this invention. Such processes can be run in a batch, semi-batch or continuous mode. Examples of such processes are well known in the art. A support for the catalyst may be employed, which may be inorganic (such as alumina, magnesium chloride or silica) or organic (such as a polymer or cross-linked polymer). Methods for the preparation of supported catalysts are known in the art. Slurry, suspension, gas phase and high-pressure processes as known to those skilled in the art may also be used with supported catalysts of the invention.

Other additives that are useful in a polymerization reaction may be employed, such as scavengers, promoters, modifiers and/or chain transfer agents, such as hydrogen, aluminum alkyls and/or silanes.

As discussed herein, catalytic performance can be determined a number of different ways, as those of skill in the art will appreciate. Catalytic performance can be determined by the yield of polymer obtained per mole of metal complex, which in some contexts may be considered to be activity. The examples provide data for these comparisons.

Another measure of catalyst polymerization performance is co-monomer incorporation. As is well known in the art, many ethylene copolymers are prepared using ethylene and at least one other monomer. These copolymers or higher order polymers in some applications require higher amounts of additional co-monomer(s) than have been practical with known catalysts. Since ethylene tends to be the most reactive monomer, obtaining higher co-monomer incorporations is a benefit that is examined for polymerization catalysts. Two useful co-monomers are 1-octene and styrene. This invention offers the possibility of higher incorporation of co-monomers such as 1-octene and styrene.

As stated herein, a solution process is specified for certain benefits, with the solution process being run at a temperature above 90° C., more specifically at a temperature above 100° C., further more specifically at a temperature above 110° C. and even further more specifically at a temperature above 130° C. Suitable solvents for polymerization are non-coordinating, inert liquids. Examples include straight and branched-chain hydrocarbons such as isobutane, butane, pentane, isopentane, hexane, isohexane, heptane, octane, Isopar-E® and mixtures thereof; cyclic and alicyclic hydrocarbons such as cyclohexane, cycloheptane, methylcyclohexane, methylcycloheptane, and mixtures thereof; perhalogenated hydrocarbons such as perfluorinated $C_{4-10}$ alkanes, chlorobenzene, and aromatic and alkyl substituted aromatic compounds such as benzene, toluene, mesitylene, and xylene. Suitable solvents also include liquid olefins which may act as monomers or comonomers including ethylene, propylene, 1-butene, butadiene, cyclopentene, 1-hexene, 1-pentene, 3-methyl-1-pentene, 4-methyl-1-pentene, 1,4-hexadiene, 1-octene, 1-decene, isobutylene, styrene, divinylbenzene, allylbenzene, and vinyltoluene (including all isomers alone or in admixture). Mixtures of the foregoing are also suitable.

In some embodiments, a solution process is specified for crystalline polypropylene production. The solution process to prepare isotactic polypropylene comprises adding a catalyst and propylene monomer to a reactor and subjecting the contents to polymerization conditions.

The ligands, metal-ligand complexes and compositions of this invention can be prepared and tested for catalytic activity in one or more of the above reactions in a combinatorial fashion. Combinatorial chemistry generally involves the parallel or rapid serial synthesis and/or screening or characterization of compounds and compositions of matter. U.S. Pat. Nos. 5,985,356, 6,030,917 and WO 98/03521, all of which are incorporated herein by reference, generally disclose combinatorial methods. In this regard, the ligands, metal-ligand complexes or compositions may be prepared and/or tested in rapid serial and/or parallel fashion, e.g., in an array format. When prepared in an array format, ligands, metal-ligand complexes or compositions may be take the form of an array comprising a plurality of compounds wherein each compound can be characterized by any of the above general formulas (i.e., I, II, III, etc.). An array of ligands may be synthesized using the procedures outlined previously. The array may also be of metal precursor compounds, the metal-ligand complexes or compositions characterized by the previously described formulae and/or description. Typically, each member of the array will have differences so that, for example, a ligand or activator or metal precursor or R group in a first region of the array may be different than the ligand or activator or metal precursor or R group in a second region of the array. Other variables may also differ from region to region in the array.

In such a combinatorial array, typically each of the plurality of compositions or complexes has a different composition or stoichiometry, and typically each composition or complex is at a selected region on a substrate such that each compound is isolated from the other compositions or complexes. This isolation can take many forms, typically depending on the substrate used. If a flat substrate is used, there may simply be sufficient space between regions so that there cannot be interdiffusion between compositions or complexes. As another example, the substrate can be a microtiter or similar plate having wells so that each composition or complex is in a region separated from other compounds in other regions by a physical barrier. The array may also comprise a parallel reactor or testing chamber.

The array typically comprises at least 8 compounds, complexes or compositions each having a different chemical formula, meaning that there must be at least one different atom or bond differentiating the members in the array or different ratios of the components referred to herein (with components referring to ligands, metal precursors, activators, group 13 reagents, solvents, monomers, supports, etc.). In other embodiments, there are at least 20 compounds, complexes or compositions on or in the substrate each having a different chemical formula. In still other embodiments, there are at least 40 or 90 or 124 compounds, complexes or compositions on or in the substrate each having a different chemical formula. Because of the manner of forming combinatorial arrays, it may be that each compound, complex or composition may not be worked-up, purified or isolated, and for example, may contain reaction by-products or impurities or unreacted starting materials.

The catalytic performance of the compounds, complexes or compositions of this invention can be tested in a combinatorial or high throughput fashion. Polymerizations can also be performed in a combinatorial fashion, see, e.g., U.S. Pat. Nos. 6,306,658, 6,508,984 and WO 01/98371, each of which is herein incorporated by reference.

EXAMPLES

General: All reactions were performed under a purified argon or nitrogen atmosphere in a Braun or Vacuum Atmospheres glove box. All solvents used were anhydrous, deoxygenated and purified according to known techniques. All ligands and metal precursors were prepared according to procedures known to those of skill in the art, e.g., under inert atmosphere conditions, etc. Ethylene/styrene and ethylene/1-octene copolymerizations and propylene polymerizations were carried out in a parallel pressure reactor, which is fully described in U.S. Pat. Nos. 6,306,658, 6,455,316 and 6,489,168, and in U.S. application Ser. No. 09/177,170, filed Oct. 22, 1998, and WO 00/09255, each of which is incorporated herein by reference.

High temperature Size Exclusion Chromatography was performed using an automated "Rapid GPC" system as described in U.S. Pat. Nos. 6,491,816, 6,491,823, 6,475,391, 6,461,515, 6,436,292, 6,406,632, 6,175,409, 6,454,947, 6,260,407, and 6,294,388 each of which is incorporated herein by reference. In the current apparatus, a series of two 30 cm×7.5 mm linear columns, with one column containing PLgel 10 um, MixB and the other column containing PLgel 5 um, MixC (available from Polymer Labs). The GPC system was calibrated using narrow polystyrene standards. The system was operated at a eluent flow rate of 1.5 mL/min and an oven temperature of 160° C. o-dichlorobenzene was used as the eluent. The polymer samples were dissolved 1,2,4-trichlorobenzene at a concentration of about 1 mg/mL. Between 40 µL and 200 µL of a polymer solution were injected into the system. The concentration of the polymer in the eluent was monitored using an evaporative light scattering detector. All of the molecular weight results obtained are relative to linear polystyrene standards.

The ratio of 1-octene to ethylene incorporated in the ethylene-octene copolymer products was determined by Raman spectroscopy. All spectra were obtained using a Bruker Equinox 055 FRA 106/S FT-Raman Spectrometer (Raman back scattering) with a 4 min acquisition time, a laser power of 500 mW, and spectral resolution of 4 $cm^{-1}$. Analysis was performed using OPUS NT software package by measuring the absorbance of the peaks at 2953, 2955, and 2957 $cm^{-1}$ (for the asymmetric $CH_3$ stretch) and the peak maximum between 2844 and 2854 $cm^{-1}$ (for the symmetric $CH_2$ stretch). The absorbance of the baseline at 3200 $cm^{-1}$ was then subtracted from these values and the ratio of the peak heights was determined. Mol % 1-octene values determined from x=A2953/A2850 ratio where Mol %=1233.2×2−160.26x+8.2296. This method was calibrated using a set of ethylene/1-octene copolymers with a range of known wt. % 1-octene content.

Crystallinity in polypropylene was determined by FTIR spectroscopy. FTIR spectra of thin films deposited from solution onto gold coated Si wafers are acquired at 4 $cm^{-1}$ resolution and with 16 scans in reflection-absorption mode on a Bruker Equinox 55 FTIR spectrometer equipped with a Pike MappIR accessory. The height ratio of two bands at 995 $cm^{-1}$ (C—H bending and $CH_3$ rocking mode from regular crystalline isotactic helices) and 972 $cm^{-1}$ (coupled C—C stretching and $CH_3$ rocking mode, independent of crystallinity) is determined as a measure of isotacticity (as known in the art, see, e.g., J. P. Luongo, *J. Appl. Polym. Sci* 3 (1960) 302–309, and T. Sundell, H. Fagerholm, H. Crozier, *Polymer* 37 (1996) 3227–3231, each of which is incorporated herein by reference). For blends of atactic and isotactic polypropylene (PP) with 0–70% isotactic PP, the IR ratio is proportional to the percentage of isotactic PP. For greater than 98% isotactic PP the ratio is greater than 0.95, for amorphous PP the ratio is 0.2.

The ratio of styrene to ethylene incorporated in the polymer products, represented as the mol % of styrene incorporated in the polymer (mol % styrene) was determined using FTIR spectroscopy. The IR spectra (16 scans at 4 $cm^{-1}$ resolution) analyzed by Partial Least Squares (PLS) analysis with PLSplus/IQ V3.04 for GRAMS/32 (Galactic Industries) software, using the following training set for calibration.

Training Set

The analysis based on a training set consisting of 180 spectra of blends of ethylene-styrene copolymers with known styrene incorporation, and atactic homo-polystyrene. The 16 known copolymers had between 1 and 47 mol % incorporated styrene. The atactic homo-polystyrene content in the blends ranged from 0 to 90% of the total styrene content of the blend. Most blends are prepared from copolymers with up to 20 mol % incorporation. Multiple spectra per blend were included in the training set.

Preprocessing of the Spectra

Mean centering; linear baseline correction based on average absorbances at 2074 $cm^{-1}$–2218 $cm^{-1}$ and 3224 $cm^{-1}$–3465 $cm^{-1}$; thickness correction based on band area from 1483 $cm^{-1}$ to 1504 $cm^{-1}$ with baseline from 1389 $cm^{-1}$–1413 $cm^{-1}$ to 1518 $cm^{-1}$–1527 $cm^{-1}$.

Analysis

PLS-1 algorithm; spectral regions 499 $cm^{-1}$ to 2033 $cm^{-1}$ and 3577 $cm^{-1}$ to 4495 $cm^{-1}$. Prediction of number ratios of atactic homo-polystyrene to total styrene ($\propto$ % atactic homo-polystyrene to total styrene) with 10 factors and ethylene to total styrene ($\propto$ mol % total styrene) with 7 factors and calculation of mol % incorporated styrene from these 2 numbers.

FTIR method for determining mol % total styrene in product: FTIR was performed on a Bruker Equinox 55+IR Scope II in reflection mode using a Pike MappIR accessory with 16 scans. The ratio of total styrene to ethylene was obtained from the ratio of band heights at 4330 cm$^{-1}$ and 1602 cm$^{-1}$. This method was calibrated using a set of ethylene-styrene copolymers with a range of known styrene content. The total styrene content of the polymer products (mol % total styrene), includes both the styrene incorporated in the ethylene-styrene copolymer and any background homopolystyrene (PS) in the product sample. For the ethylene-styrene copolymerization conditions employed, the homopolystyrene background level is typically less than 3.5 wt % (1 mol %).

Differential Scanning Calorimetry (DSC) measurements were performed on a TA instrument DSC 2920 to determine the melting point of polymers. The sample was equilibrated at 2000 and held for 4 minutes. The sample was cooled to −50° C. with a rate of 10° C./min and held at −50° C. for 4 minutes. Then, the sample was heated to 200° C. at a rate of 10° C./min and data were collected during that heating period.

List of Abbreviations used in this section include: Me=methyl, Et=ethyl, Bn or Bz=benzyl, Ac=CH$_3$CO, EA=ethyl acetate, Ts=tosyl=para-toluenesulfonyl, THP=tetrahydropyran, dppf=1,1'-bis(diphenylphosphino)ferrocene, MOM=methoxymethyl=CH$_3$OCH$_2$—, DMF=dimethylformamide The ligands in these examples are prepared according to the general schemes described above and shown below, where "building blocks" are first prepared and then coupled together.

Part A: Synthesis of Building Blocks

Part 1: Synthesis of Substituted 2-Bromophenols and 2-Bromophenylether Building Blocks:

Example 1

Scheme A1

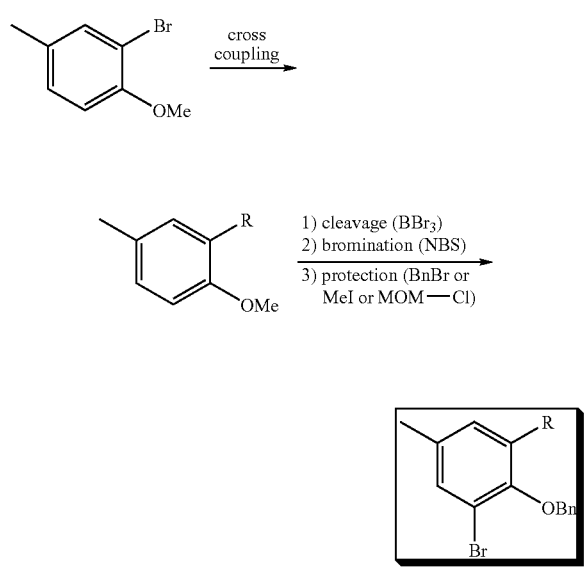

Scheme A1(a): Cross Coupling with Carbazole Derivatives

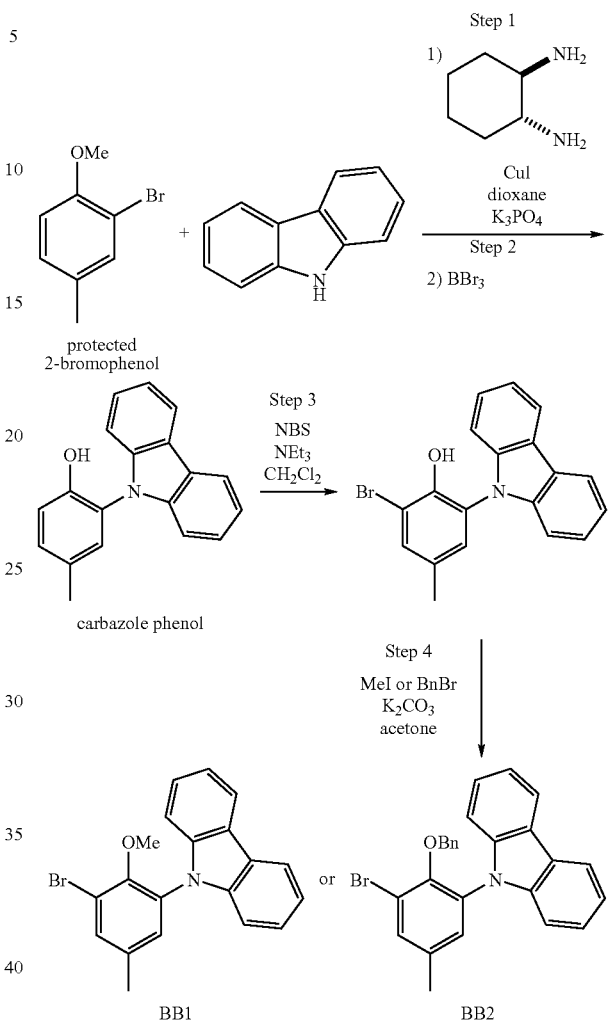

Building Blocks BB1 and BB2

Step 1: CuI-Catalyzed Cross-coupling:

A solution of the protected 2-bromophenol (4.6 mmol) and carbazole (5.5 mmol) in dioxane (8 mL) was degassed with argon. CuI (0.215 mmol, 5%), racemic trans-1,2-diaminocyclohexane (0.86 mmol, 20%), and K$_3$PO$_4$ (8 mmol) were added and the resulting mixture was stirred at 100° C. for 16 h. After filtration, the solvent was removed and crude product was purified by flash chromatography to give 4.04 mmol of the product (88% yield).

Step 2: Cleavage of the Methyl Ether:

To a solution of the carbazole methyl ether in dry CH$_2$Cl$_2$ were added two equivalents of BBr$_3$ (1 M solution in CH$_2$Cl$_2$) and the resulting solution was stirred for 5 hours (TLC control). Water was added, the resulting mixture was extracted with ethyl acetate, and the organic layer was dried over Na$_2$SO$_4$. The crude product was purified by flash chromatography.

Step 3: Bromination:

To a solution of the carbazole phenol (4.3 mmol) and NEt$_3$ (4.3 mmol) in CH$_2$Cl$_2$ (10 ml) was added dropwise a solution of NBS (N-bromosuccinimide, 4.8 mmol) in CH$_2$Cl$_2$ (30 mL). The resulting solution was stirred for 30 min and then quenched with 2N HCl (5 mL). Water (30 mL) was added, the mixture was extracted with CH$_2$Cl$_2$, and the organic layer was dried over Na$_2$SO$_4$. The crude product was purified by flash chromatography to give 1.8 mmol of the product (43% yield) (JZ-1009-31). $^1$H NMR (300 MHz, CDCl$_3$): 8.15 (d, 2H), 7.11–7.52 (m, 8H), 5.35 (s, 1H), 2.34 (s, 3H). (GC-MS available)

Step 4: Protection of Phenol as Methyl Ether (BB1) or Benzyl Ether (BB2):

A mixture of a phenol building block (1 equiv.), MeI or BnBr (1.5 equiv.) and K$_2$CO$_3$ (2 equiv.) in acetone (ca. 0.5 mmol/ml) was stirred at 60° C. for 2–4 hours. After addition of CH$_2$Cl$_2$ and filtration, the solvent was removed in vacu and the crude product was dried in a vacuum oven.

Some additional 2-bromophenol building blocks synthesized in a manner similar to that described in Scheme A1(a):

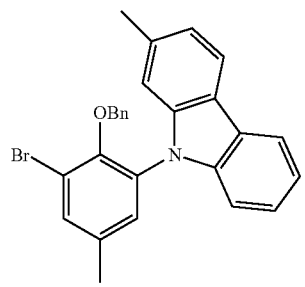

BB3

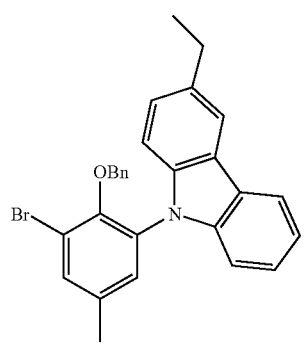

BB4

Scheme A1(b): 2-Bromophenol Building Blocks via Suzuki Cross Coupling

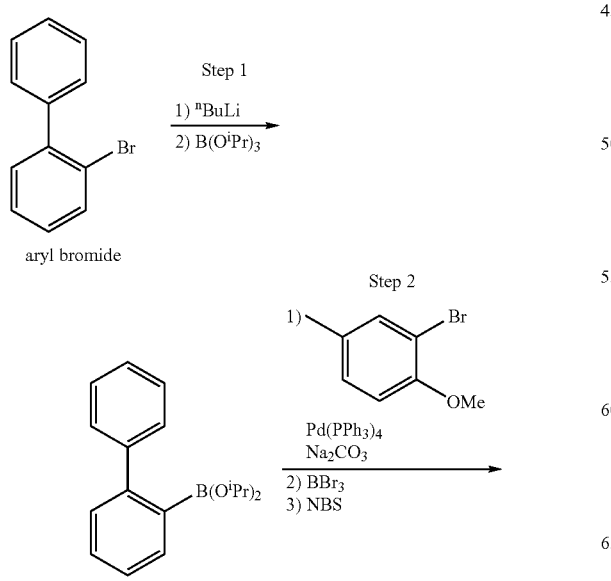

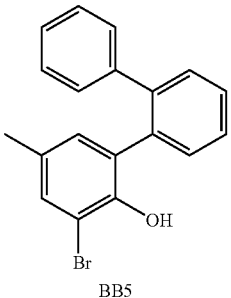

BB5

Synthesis of 2-Bromophenol Building Block BB5

Step 1: n-BuLi (22.5 mmol, from a 1.6 M solution in hexanes, 14 mL) was added slowly to a solution of the aryl bromide (21.44 mmol, 5 g) in THF (50 mL, anhydrous) at −78° C. under an atmosphere of argon. After stirring for 30 min at that temperature, triisopropyl borate (25.7 mmol, 6 mL) was added slowly and the temperature was allowed to come to room temperature (30 min). After stirring for another 30 min, the solvent was removed and the crude boronic acid was used without further purification.

Step 2: A mixture of the protected 2-bromophenol (methyl ether, 3.38 g, 16.8 mmol), the boronic acid (22.5 mmol), Na$_2$CO$_3$ (9 mL of a 2 M solution in water, 18 mmol) and dimethoxy ethane (100 mL) was degassed with argon. Pd(PPh$_3$)$_3$ (485 mg, 0.42 mmol, 2.5%) was added and the resulting mixture was stirred at 85° C. for 16 h under argon. Ethyl acetate (30 mL) was added and the mixture was dried over Na$_2$SO$_4$. After filtration, the solvent was removed and the crude product was purified by flash chromatography (Ethylacetate/hexane=1/10) to give 1.7 g of the cross-coupling product (6 mmol, 28% yield). After cleavage of the methyl ether with BBr$_3$ in CH$_2$Cl$_2$ and bromination with NBS as shown in Scheme A1(a), the crude product was purified to yield 1.4 g of the building block BB5 (4.13 mmol, 68%). (characterized by GC-MS, $^1$H NMR).

Some additional 2-bromophenol building blocks (BB6 to BB12) synthesized in a manner similar to that described above in connection with Scheme A1(b):

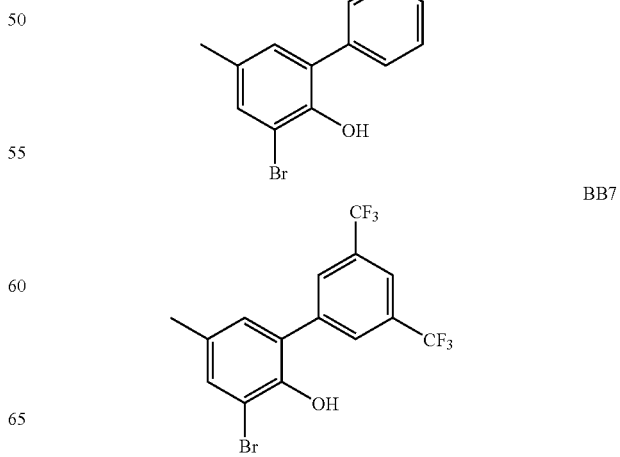

-continued
BB8 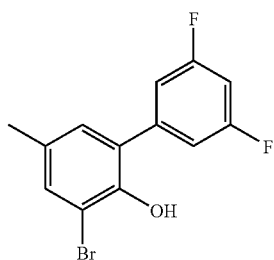
BB9 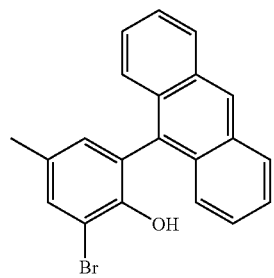
BB10 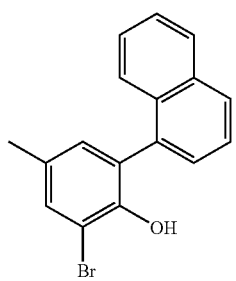
BB11 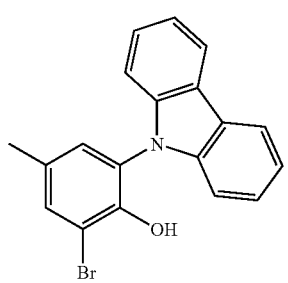
BB12 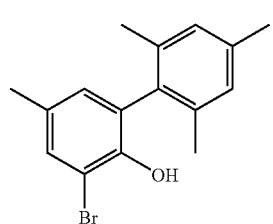
2-bromophenol building blocks synthesized in a manner similar to that described above for Scheme A1(c) (only bromination and deprotection):
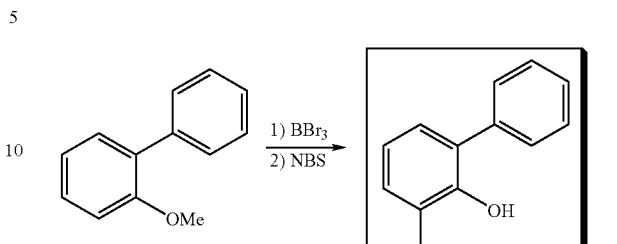
BB13
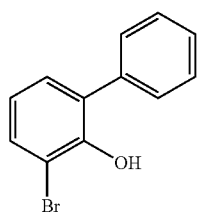
BB14
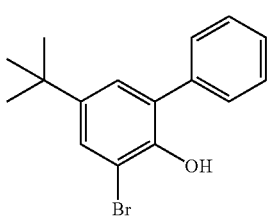
BB15
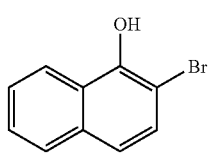
Example 2
Scheme A2: Synthesis of Substituted 2-Bromophenyl-Benzyl Ethers via 2,6-dibromo-4-methyl-phenyl benzyl ether
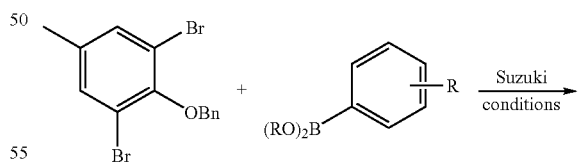
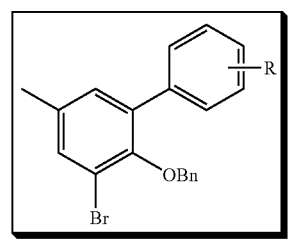

Scheme A2(a):

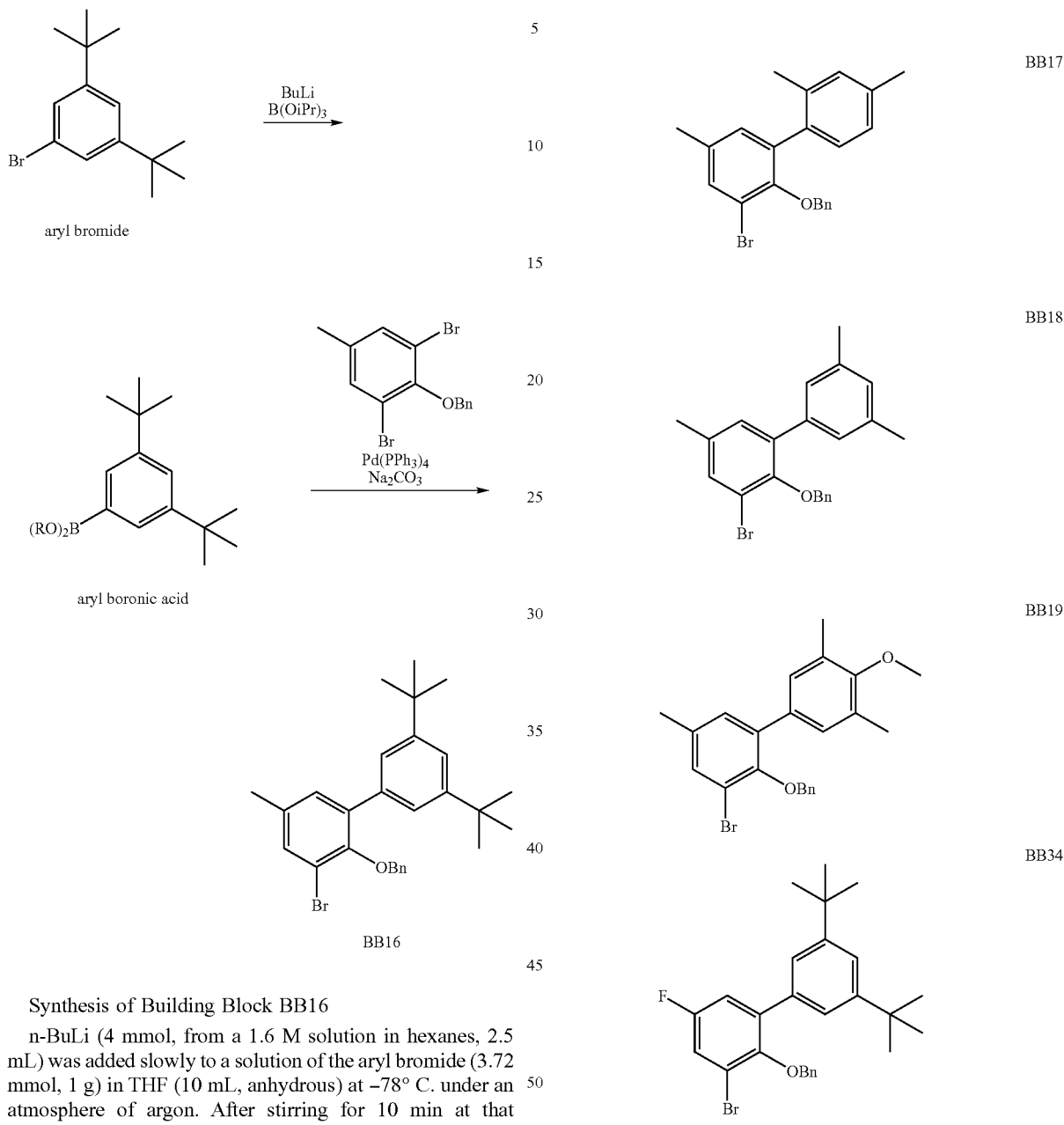

Synthesis of Building Block BB16 n-BuLi (4 mmol, from a 1.6 M solution in hexanes, 2.5 mL) was added slowly to a solution of the aryl bromide (3.72 mmol, 1 g) in THF (10 mL, anhydrous) at −78° C. under an atmosphere of argon. After stirring for 10 min at that temperature, triisopropyl borate (4.3 mmol, 988 µL) was added slowly and the temperature was allowed to come to room temperature (30 min). After stirring for another 30 min, the solvent was removed and the crude aryl boronic acid was used without further purification. A mixture of the protected 2,6-dibromophenol (benzyl ether, 1.07 g, 3 mmol), the boronic acid (3.72 mmol), $Na_2CO_3$ (2.5 mL of a 2 M solution in water, 5 mmol) and dimethoxy ethane (15 mL) was degassed with argon. $Pd(PPh_3)_3$ (170 mg, 0.15 mmol, 5%) was added and the resulting mixture was stirred at 85° C. for 16 h under argon. Ethyl acetate (30 mL) was added and the mixture was dried over $Na_2SO_4$. After filtration, the solvent was removed and the crude product was purified by flash chromatography (Ethylacetate/hexane=1/10) to give 1.143 g of the product BB16 (2.46 mmol, 82% yield).

Some additional building blocks synthesized in a manner similar to that described above in connection with Scheme A2(a):

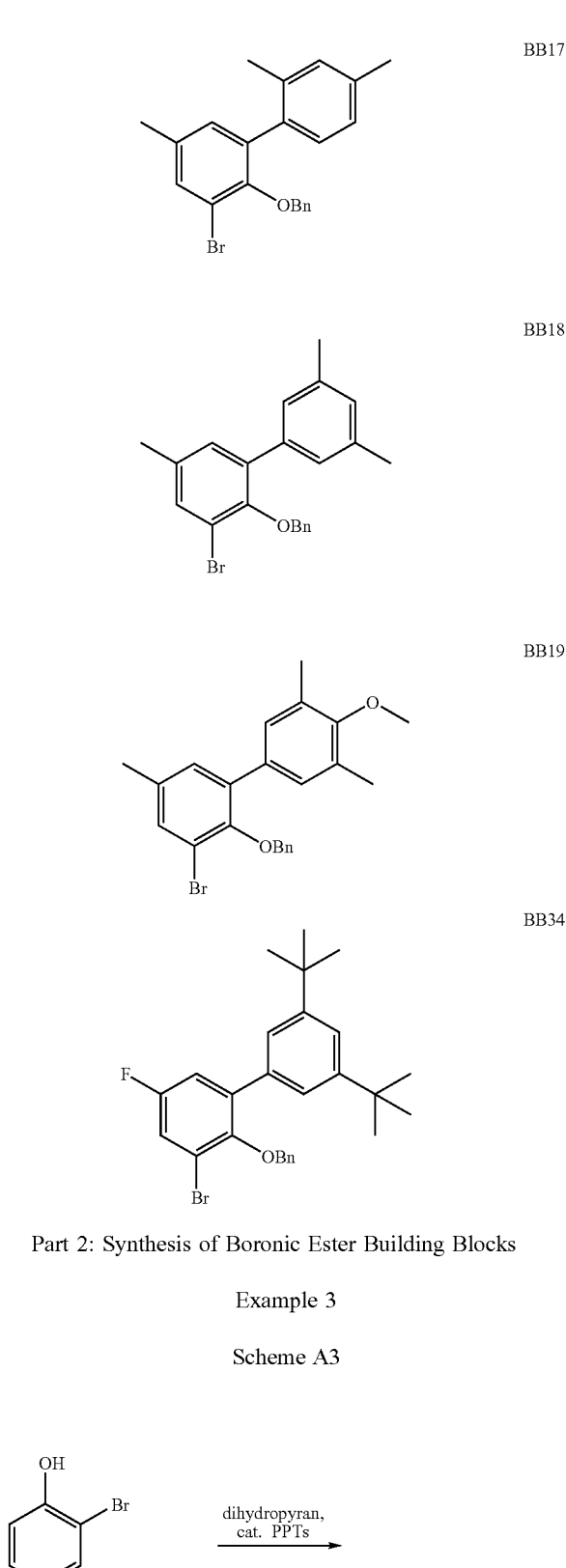

Part 2: Synthesis of Boronic Ester Building Blocks

Example 3

Scheme A3

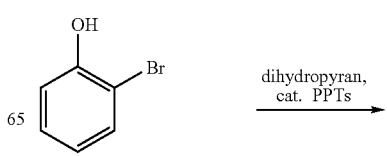

Example 4

Scheme A4

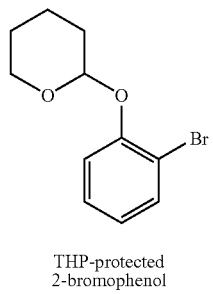

THP-protected
2-bromophenol

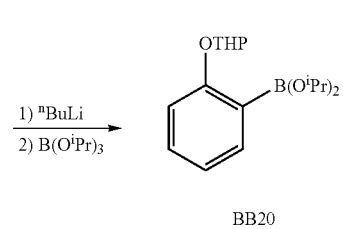

BB20

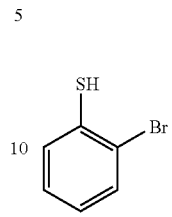

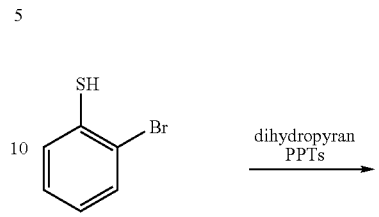

Introduction of the THP (tetrahydropyran) protection group—A solution of 2-bromophenol (25 g, 145 mmol), dihydropyran (22.3 g, 264 mmol) and pyridinium p-toluenesulfonate ("PPTs", 3.3 g, 13 mmol) in methylene chloride (100 mL) was stirred for 16 h at room temperature. The resulting solution was washed with aq. $NH_4C_1$, $H_2O$ and brine, and dried over $Na_2SO_4$. After removal of the solvent, the THP-protected 2-bromophenol was isolated as a yellow oil (35 g, 137 mmol, 95%).

Formation of the boronic ester—n-BuLi (1.1 mmol, from a 1.6 M solution in hexanes) was added slowly to a solution of the THP-protected 2-bromophenol (1 mmol) in THF (5 mL, anhydrous) at −78° C. under an atmosphere of argon. After stirring for 10 min at that temperature, triisopropyl borate was added slowly and the temperature was allowed to come to room temperature (30 min). After stirring for another 30 min, the solvent was removed and the crude THP-protected boronic ester (BB20) was used without further purification.

Some additional building blocks synthesized in a manner similar to that described above in connection with Scheme A3:

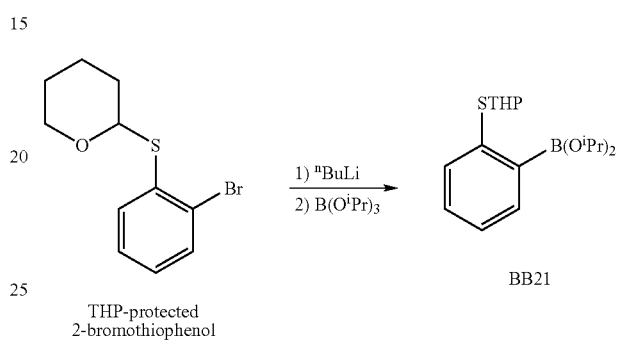

THP-protected
2-bromothiophenol

A solution of bromobenzenethiol (25 g, 132 mmol), dihydropyran (22.3 g, 264 mmol) and pyridinium p-toluenesulfonate ("PPTs", 3.3 g, 13 mmol) in methylene chloride (100 mL) was stirred for 16 h at room temperature. The resulting solution was washed with aq. $NH_4Cl$, $H_2O$ and brine, and dried over $Na_2SO_4$. After removal of the solvent, the THP-protected 2-bromothiophenol was isolated as a yellow oil (34 g, 125 mmol, 95%). The corresponding THP-protected boronic ester (BB21) was prepared according to standard methods described above.

Part 3: Synthesis of (O,O)- and (O,S)-Bridged Building Blocks

Example 5

(O,O)-Bridged Building Block BB22

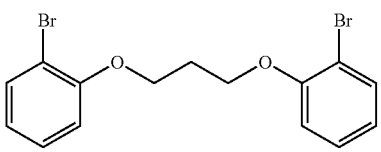

BB22

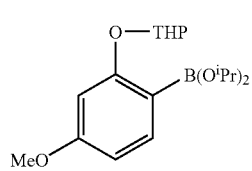

BB35

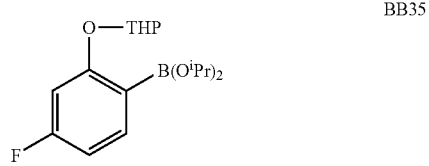

BB36

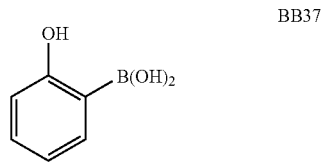

BB37 (hydrolysis of BB20)

A mixture of bromophenol (40 mmol, 4.64 mL), 1,3-dibromopropane (20 mmol, 2.03 mL) and $Cs_2CO_3$ (50 mmol, 16.3 g) in acetone (100 mL) was stirred at 60° C. for 16 hours. After addition of $CH_2Cl_2$ and filtration, the solvent was removed in vacu and the crude product was dried in a vacuum oven to give 5.77 g of BB22 (75%). (characterized by GC-MS, $^1H$ NMR)

Example 6

(O,S)-Bridged Building Block BB23

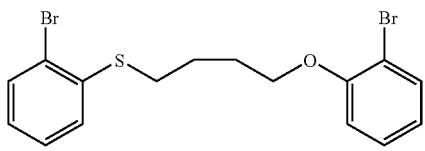

BB23

A mixture of bromophenol (4.62 mmol, 800 mg), 1,4-dibromobutane (20 mmol, 4.32 g) and $K_2CO_3$ (10 mmol, 1.38 g) in acetone (10 mL) was stirred at 60° C. for 1 hour. After addition of $CH_2Cl_2$ and filtration, the solvent was removed and the crude product was purified by flash chromatography (Ethylacetate/hexane=1/10) to give 1.278 g of the product (4.15 mmol, 90% yield). Bromothiophenol (4.15 mmol, 784 mg), $K_2CO_3$ (10 mmol, 1.38 g) and acetone (10 mL) were added and the resulting mixture was stirred at 60° C. for 2 hours. After addition of $CH_2Cl_2$ and filtration, the solvent was removed to give 1.693 g of the product BB23 (4.07 mmol, 88% yield). (characterized by GC-MS, $^1H$ NMR)

Example 7

Synthesis of (O,O)- and (O,S)-Bridged Bis Aryl Boronic Esters

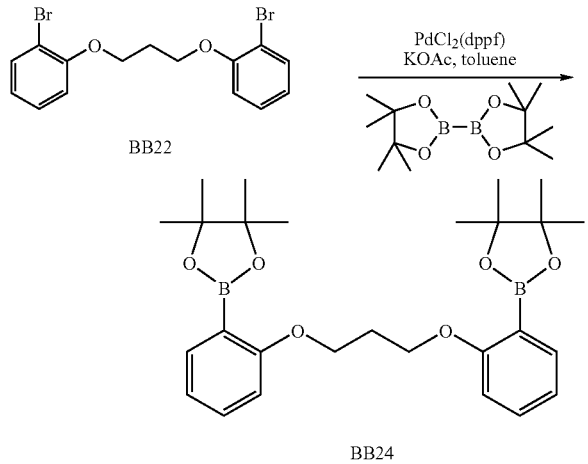

Building Block BB24:

A mixture of the (O,O)-bridged bis(arylbromide) BB22 (397 mg, 1.03 mmol), the boronic ester (574 mg, 2.26 mmol), KOAc (607 mg, 6.16 mmol) and toluene (15 mL) was degassed with argon. $PdCl_2(dppf)$ (50 mg, 0.06 mmol) was added and the resulting mixture was stirred at 85° C. for 16 h under argon. After filtration, the solvent was removed and the crude product was purified by flash chromatography ($CH_2Cl_2$/hexane=10/1, add 1% of $NEt_3$) to give 240 mg of the product (O,O)-bridged bis(aryl boronic ester) BB24 (0.5 mmol, 50% yield).

Building Block BB25:

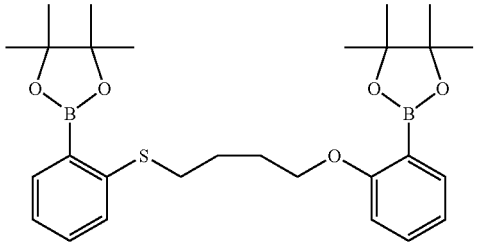

BB25

A mixture of the (O,S)-bridged bis(arylbromide) BB23 (416 mg, 1 mmol), the boronic ester (559 mg, 2.2 mmol), KOAc (588 mg, 6 mmol) and toluene (15 mL) was degassed with argon. $PdCl_2(dppf)$ (50 mg, 0.06 mmol) was added and the resulting mixture was stirred at 85° C. for 16 h under argon. After filtration, the solvent was removed and the crude product was purified by flash chromatography ($CH_2Cl_2$/hexane=10/1, add 1% of $NEt_3$) to give 110 mg of the product (O,S)-bridged bis(aryl boronic ester) BB25 (0.5 mmol, 50% yield).

Part B: Synthesis of (O,O)-Bridged Bis(Biphenylphenol) Ligands:

Scheme B1:

Step 1

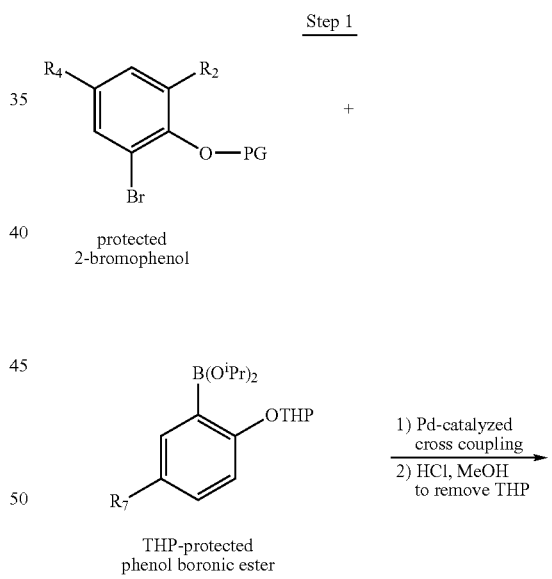

-continued

Step 2

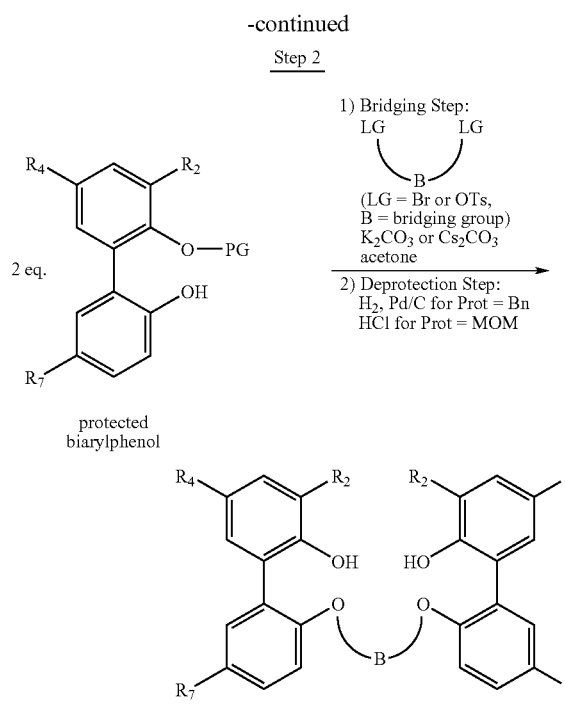

Detailed Example of a Ligand Synthesized According to Scheme B1:

Step 1

-continued

Step 2

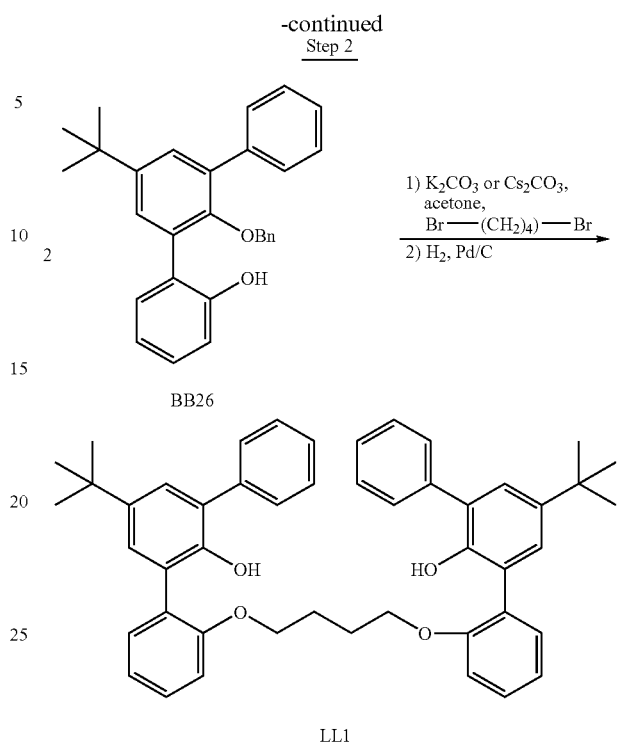

Example 8

Building Block BB26: Procedure B1 Step 1

A mixture of the benzyl ether protected 2-bromophenol (BB14, 670 mg, 1.7 mmol), the in situ formed O-THP protected ary boronic acid (BB20, 750 mg, 2.5 mmol), Na$_2$CO$_3$ (1.5 mL of a 2 M solution in water, 3 mmol) and dimethoxy ethane (10 mL) was degassed with argon. Pd(PPh$_3$)$_3$ (230 mg, 0.2 mmol, 10%) was added and the resulting mixture was stirred at 85° C. for 16 h under argon. Ethyl acetate (30 mL) was added and the mixture was dried over Na$_2$SO$_4$. After filtration, the solvent was removed and the THP ether was cleaved in the presence of HCl (0.2 mL), EA (1 mL), and MeOH (1 mL). The crude product was purified by flash chromatography (Ethylacetate/hexane=1/10) to give 638 mg of the product BB26 (1.56 mmol, 92% yield). $^1$H NMR (300 MHz, CDCl$_3$): 7.64 (d br, J=7 Hz, 2H), 7.35–7.52 (m, 7H), 7.05–7.25 (m, 5H), 7.72 (d br, J=7 Hz, 2H), 4.27 (s, 2H), 1.40 (s, 9H).

Example 9

Ligand LL1: Procedure B1 Step 2

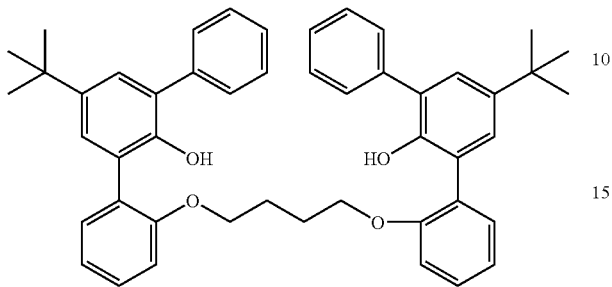

LL1

A mixture of the phenol building block (BB26) (418 mg, 1.01 mmol), 1,4-dibromobutane (109 mg, 0.5 mmol), and $K_2CO_3$ (260 mgs, 2 mmol) in acetone (5 mL) was stirred at 60° C. for 16 hours. After filtration, the solvent was removed and the crude product was dissolved in ethyl acetate (2 mL) and EtOH (2 mL). Pd (100 mg, 10% on activated carbon) was added and the suspension was stirred under an atmosphere of hydrogen for 16 h at room temperature and at 50° C. for 3 hours. After filtration and removal of the solvent, the crude product was purified by flash chromatography (Ethylacetate/hexane=1/10) to yield 205 mg of the final product LL1 as a white solid (0.297 mmol, 59%). $^1$H NMR (300 MHz, CDCl$_3$): 7.52 (d br, J=7 Hz, 4H), 7.36 (t br, J=7 Hz, 4H), 7.26–7.34 (m, 8H), 7.18 (d, J=2.5 Hz, 2H), 7.09 (t, J=7.5 Hz, 2H), 6.89 (d, J=8 Hz, 2H), 6.00 (s, 2H), 3.94 (br, 4H), 1.78 (br, 4H), 1.32 (s, 18H).

Some additional ligands synthesized in a method similar to that just described according to Scheme B1 chosen to exemplify some variations in the synthetic method:

Example 10

Building Block BB27

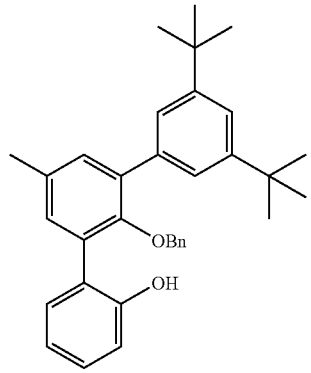

BB27

According to Scheme B 1 and General Procedure B 1 Step 1, the in situ generated O-THP boronic acid BB20 (0.7 mmol), the protected 2-bromophenol building block BB16 (0.5 mmol, 232 mg), $Na_2CO_3$ (0.5 mL of a 2 M solution in water, 1 mmol) and dimethoxy ethane (7 mL) were reacted in the presence of Pd(PPh$_3$)$_3$ (80 mg, 0.07 mmol) at 85° C. for 16 h. After cleavage of the THP ether and purification, 128 mg of the product BB27 was obtained (0.268 mmol, 54% yield). $^1$H NMR (300 MHz, CDCl$_3$): 7.52 (t, J=2 Hz, 1H), 7.35–7.42 (m, 5H), 7.22–7.30 (m, 2H), 7.05–7.20 (5H), 6.65 (dbr, J=7 Hz, 2H), 4.29 (s, 2H), 2.47 (s, 3H), 1.34 (s, 18H).

Example 11

Ligand LL2

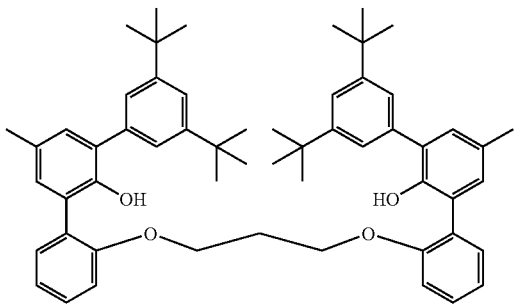

LL2

According to Scheme B1 and General Procedure B1 Step 2, a mixture of the phenol building block BB27 (128 mg, 0.268 mmol), propane-1,3-diol-di-p-tosylate (51 mg, 0.134 mmol), and $Cs_2CO_3$ (163 mgs, 0.5 mmol) in acetone (2 mL) was stirred at 60° C. for 16 hours. After stirring the benzyl ether under an atmosphere of $H_2$ (500 psi) in the presence of Pd/C (50 mg, 5%, Aldrich) in ethyl acetate (1 mL), EtOH (1 mL) and AcOH (1 drop) at 50° C. for 2 h, the product was purified by flash chromatography to give 54 mg of the product LL2 (0.066 mmol, 50% yield). $^1$H NMR (300 MHz, CDCl$_3$): 7.48 (d, J=1 Hz, 2H), 7.32–7.40 (m, 6H), 6.98–7.20 (m, 8H), 6.76 (d, J=8 Hz, 2H), 5.70 (s, 2H), 4.06 (t, J=6 Hz, 4H), 2.33 (s, 6H), 2.05 (tt, J=6 Hz, 2H), 1.31 (s, 36H).

Example 12

Ligand LL3

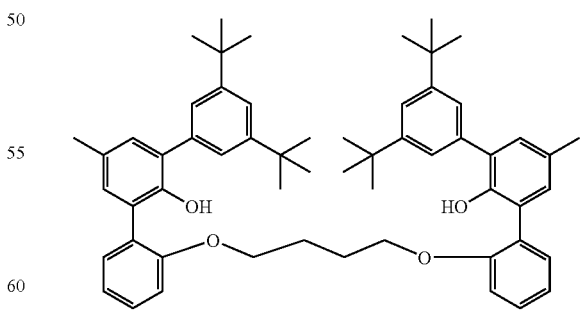

LL3

According to Scheme B1 and General Procedure B1 Step 2, a mixture of the phenol building block BB27 (100 mg, 0.209 mmol), 1,4-dibromobutane (23 mg, 0.105 mmol), and $Cs_2CO_3$ (130 mgs, 0.4 mmol) in acetone (2 mL) was stirred at 60° C. for 4 hours. After stirring the benzyl ether1 under an atmosphere of H₂ (500 psi) in the presence of Pd/C (50 mg, 5%, Aldrich) in ethyl acetate (1 mL), EtOH (1 mL) and AcOH (1 drop) at 50° C. for 2 h, the product was purified by flash chromatography to give 36 mg of the product LL3 (0.043 mmol, 41% yield). ¹H NMR (300 MHz, CDCl₃): 7.25–7.48 (m, 1014, 7.02–7.15 (m, 6H), 6.85 (d, J=7 Hz, 2H), 5.92 (s, 2H), 3.91 (s br, 4H), 2.31 (s, 6H), 1.79 (s br, 4H), 1.31 (s, 36H).

mg, 5%, Aldrich) in ethyl acetate (1 mL), EtOH (1 mL) and AcOH (1 drop) at 50° C. for 2 h, the product was purified by flash chromatography to give 320 mg of the product LL4 (0.41 mmol, 38% yield). ¹H NMR (300 MHz, CDCl₃): 8.10 (d, J=8 Hz, 4H), 7.43 (dd, J=7.5 Hz, 2 Hz, 2H), 7.05–7.33 (m, 20H), 6.81 (dd, J=8 Hz, 0.5 Hz, 2H), 6.02 (d, 2H), 3.8 (s br, 4H), 2.33 (s, 6H), 1.68 (s br, 4H).

Example 13

Building Block BB28

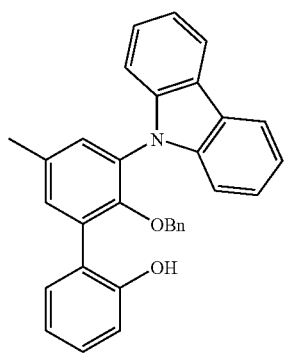

Example 15

Ligand LL5

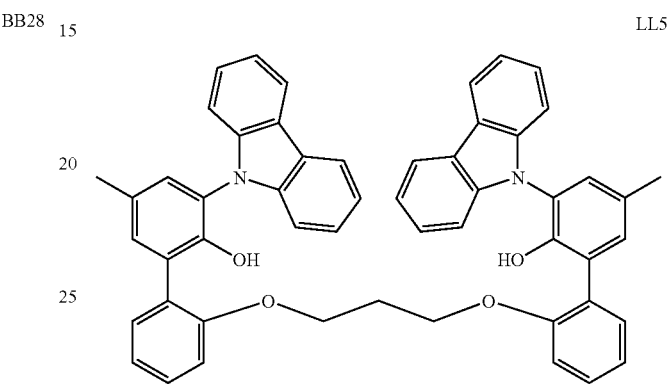

According to Scheme B1 and General Procedure B1 Step 1, the in situ generated O-THP protected boronic acid BB20 (4.5 mmol), the protected 2-bromophenol building block BB2 (3.7 mmol, 1.64 g), Na₂CO₃ (3 mL of a 2 M solution in water, 6 mmol) and dimethoxy ethane (15 mL) were reacted in the presence of Pd(PPh₃)₃ (231 mg, 0.2 mmol) at 85° C. for 16 h. After cleavage of the THP ether and purification, 1.21 g of the product BB28 was obtained (2.66 mmol, 72% yield). ¹H NMR (300 MHz, CDCl₃): 8.15 (d br, J=7.5 Hz, 2H), 7.25–7.42 (m, 10H), 6.92–7.08 (m, 3H), 8.62 (t br, J=8 Hz, 2H), 6.23 (d br, J=7 Hz, 2H), 4.05 (s, 2H), 2.45 (s, 3H).

According to Scheme B1 and General Procedure B1 Step 2, a mixture of the phenol building block BB28 (1.202 g, 2.64 mmol), propane-1,3-diol-di-p-tosylate (506 mg, 1.32 mmol), Cs₂CO₃ (1.63 g, 5 mmol) in acetone (5 mL) was stirred at 60° C. for 16 hours. After stirring the benzyl ethers under an atmosphere of H₂ (500 psi) in the presence of Pd/C (20 mg, 5%, Aldrich) in ethyl acetate (2 mL) and EtOH (2 mL) at 50° C. for 2 h, the product was purified by flash chromatography to give 630 mg of the product LL5 (0.82 mmol, 62%). ¹H NMR (300 MHz, CDCl₃): 8.18 (d, J=8 Hz, 4H), 7.09–7.39 (m, 18H), 6.88–9.95 (m, 4H), 6.30 (d, 2H), 5.55 (s, 2H), 3.95 (t, 4H), 2.35 (s, 6H), 2.14 (tt, 2H). ¹H NMR (300 MHz, CDCl₃): 8.18 (d, J=8 Hz, 4H), 7.09–7.39 (m, 18H), 6.88–9.95 (m, 4H), 6.30 (d, 2H), 5.55 (s, 2H), 3.95 (t, 4H), 2.35 (s, 6H), 2.14 (tt, 2H).

Example 14

Ligand LL4

Example 16

Building Block BB29

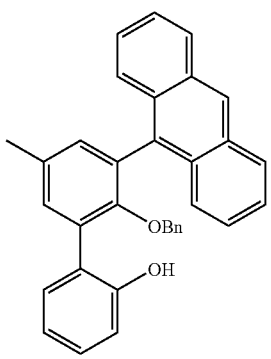

According to Scheme B1 and General Procedure B1 Step 2, a mixture of the phenol building block BB28 (490 mg, 1.077 mmol), 1,4-dibromobutane (116 mg, 0.54 mmol), and Cs₂CO₃ (489 mgs, 1.5 mmol) in acetone (5 mL) was stirred at 60° C. for 4 hours. After stirring the benzyl ethers under an atmosphere of H₂ (500 psi) in the presence of Pd/C (50

According to Scheme B1 and General Procedure B1 Step 1, the in situ generated O-THP protected aryl boronic acid BB20 (0.7 mmol), the protected 2-bromophenol building block BB9 (0.5 mmol, 226 mg), Na₂CO₃ (0.5 mL of a 2 M solution in water, 1 mmol) and dimethoxy ethane (7 mL) were reacted in the presence of Pd(PPh₃)₃ (80 mg, 0.07 mmol) at 85° C. for 16 h. After cleavage of the THP ether and purification, 135 mg of the product BB29 was obtained (0.29 mmol, 58% yield). ¹H NMR (300 MHz, CDCl₃): 8.45 (s, 1H), 8.05 (d, J=8.5 Hz, 2H), 7.75 (d, J=8.5 Hz, 2H), 7.22–7.45 (m, 10H), 7.02–7.10 (m, 2H), 6.95 (t, J=7.5 Hz, 1H), 6.80 (t, J=7 Hz, 2H), 6.05 (d, J=8 Hz, 2H), 4.05 (s, 2H), 2.48 (s, 3H).

Example 17

Ligand LL6

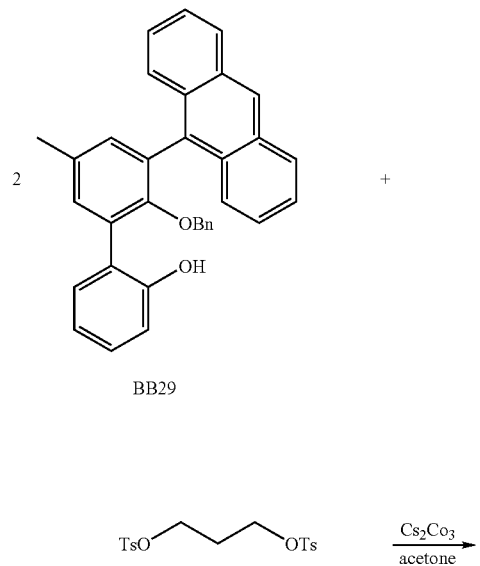

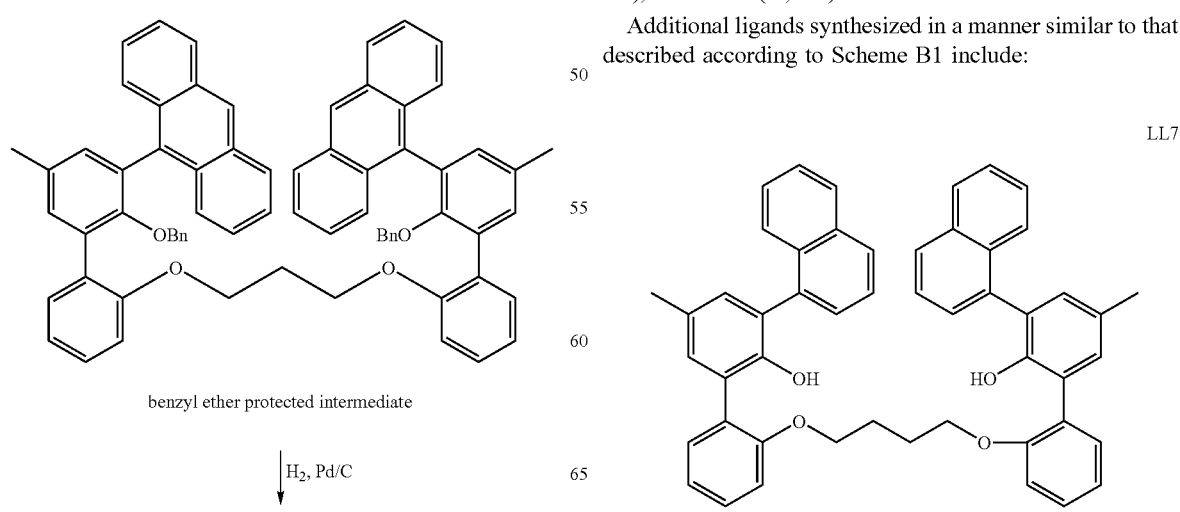

-continued

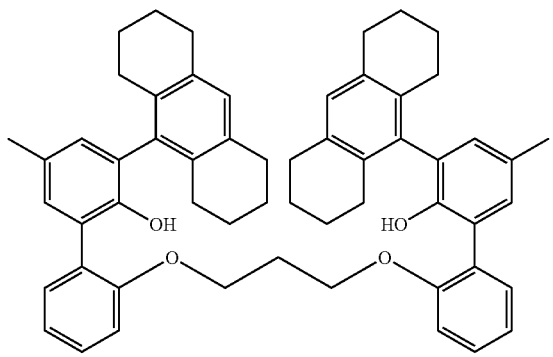

LL6

According to Scheme B1 and General Procedure B1 Step 2, a mixture of the phenol building block BB29 (135 mg, 0.29 mmol), propane-1,3-diol-di-p-tosylate (56 mg, 0.146 mmol), and Cs₂CO₃ (196 mgs, 0.6 mmol) in acetone (2 mL) was stirred at 60° C. for 16 hours. After stirring the benzyl ether protected intermediate under an atmosphere of H₂ (500 psi) in the presence of Pd/C (50 mg, 5%, 57% H₂O, Johnson Mathey) in THF (1 mL) and EtOH (1 mL) at 50° C. for 2 h, the product was purified by flash chromatography (Ethylacetate/hexane=1/10) to give 50 mg of the product LL6 (0.062 mmol, 43%). ¹H NMR (300 MHz, CDCl₃): 7.35 (dd, J=7.5 Hz, 1.5 Hz, 2H), 7.18 (t, J=7.5 Hz, 2H), 7.05 (t, J=7.5 Hz, 2H), 6.99 (d, J=1.5 Hz, 2H), 6.85 (s, 2H), 6.81 (d, J=1.5 Hz, 2H), 6.72 (d, J=8 Hz, 2H), 4.0 (t, J=5.5 Hz, 4H), 2.70–2.80 (m, 8H), 2.35 (s, 6H), 2.18–2.46 (m, 4H), 2.02 (tt, J 5.5 Hz, 2H), 1.50–1.78 (m, 20H).

In another experiment, the benzyl ether protected intermediate was isolated in 80% yield. ¹H NMR (300 MHz, CDCl₃): 8.51 (s, 2H), 8.05 (d, J=7.5 Hz, 4H), 7.85 (d, J=7.5 Hz, 4H), 7.12–7.48 (m, 18H), 6.98 (t, J=7.5 Hz, 2H), 6.82 (t, J=7.5 Hz, 2H), 6.70 (t, J=7.5 Hz, 4H), 6.51 (d, J=8 Hz, 2H), 5.90 (d, J=7.5 Hz, 4H), 3.94 (s, 4H), 3.88 (t, J=4H), 2.45 (s, 3H), 2.01–2.05 (m, 2H).

Additional ligands synthesized in a manner similar to that described according to Scheme B1 include:

LL8
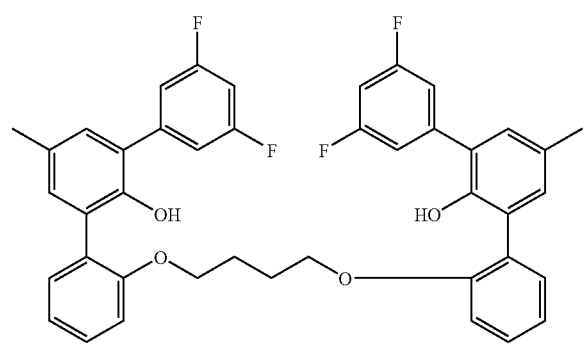
LL9
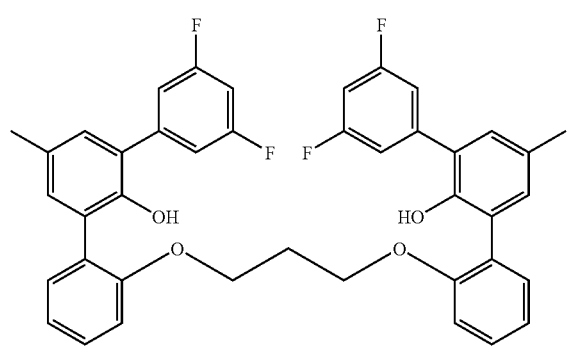
LL10
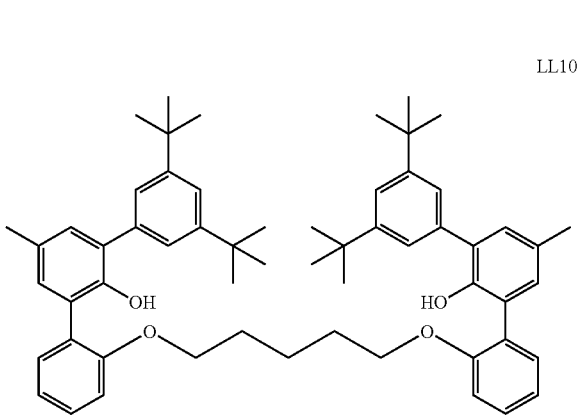
LL11
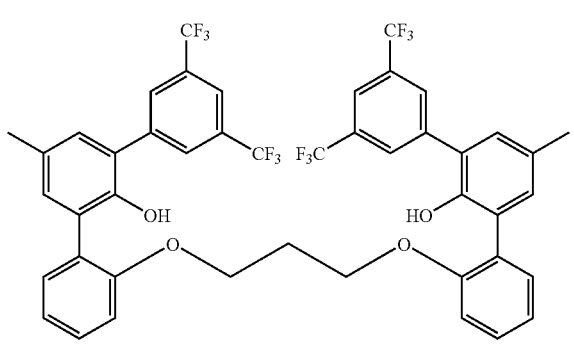
LL12
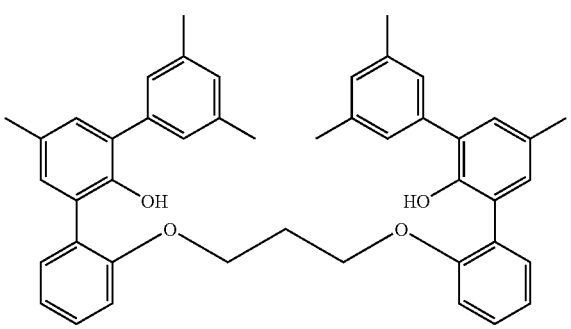
LL13
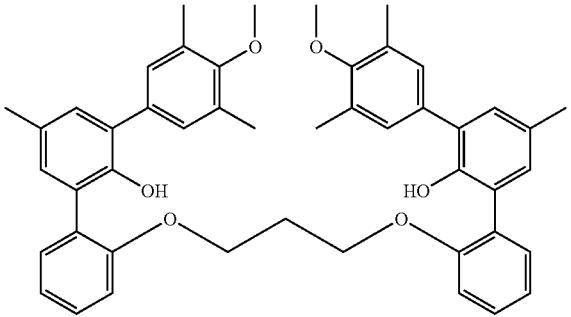
LL14
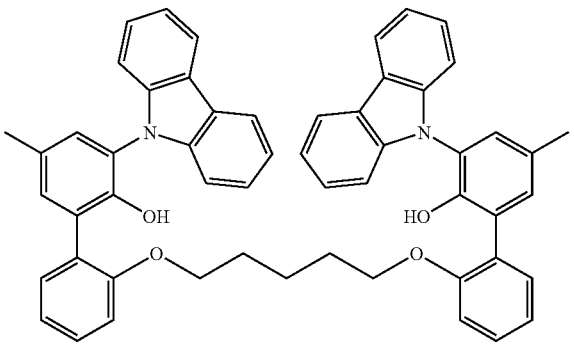
LL52
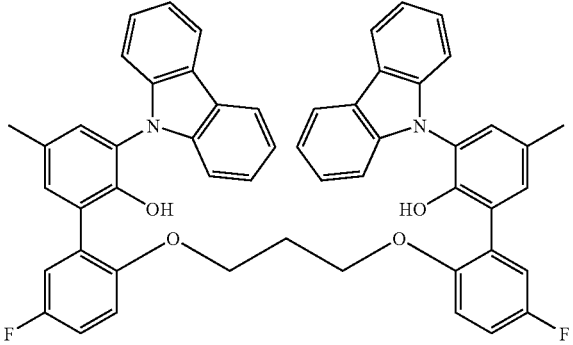

-continued
LL53
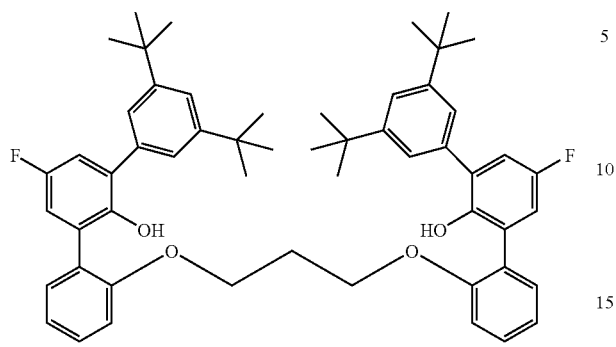
LL57
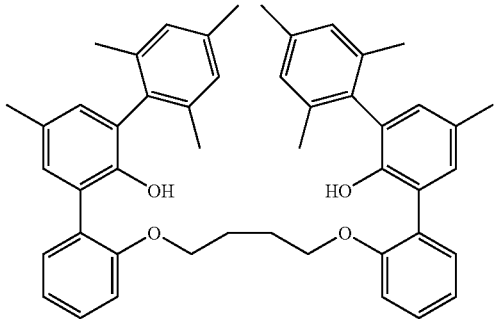
LL54
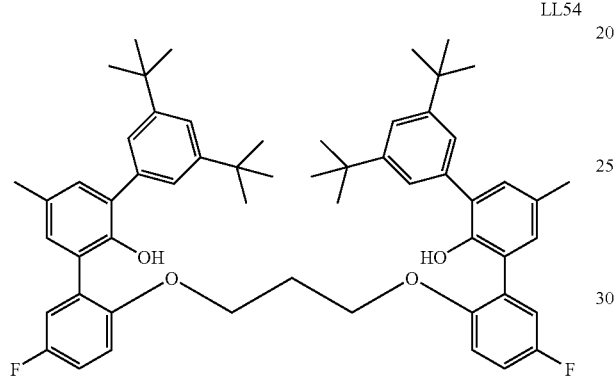
LL15
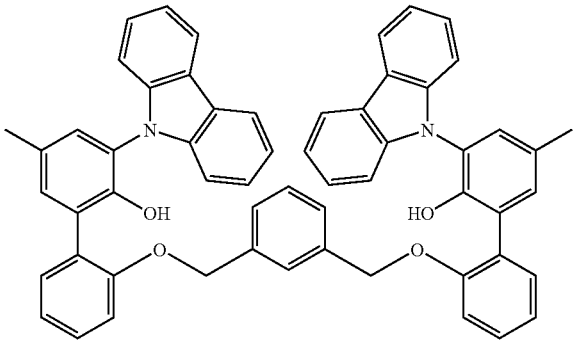
LL55
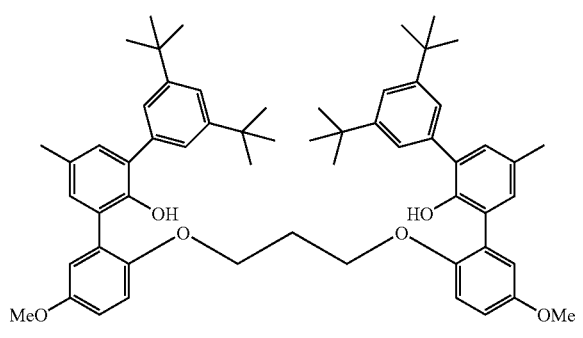
LL16
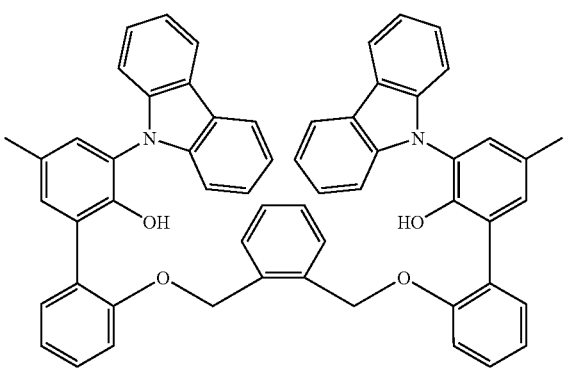
LL56
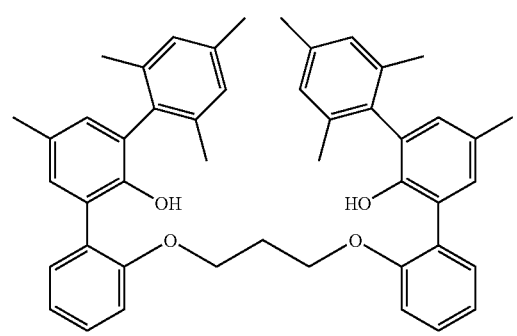
LL17
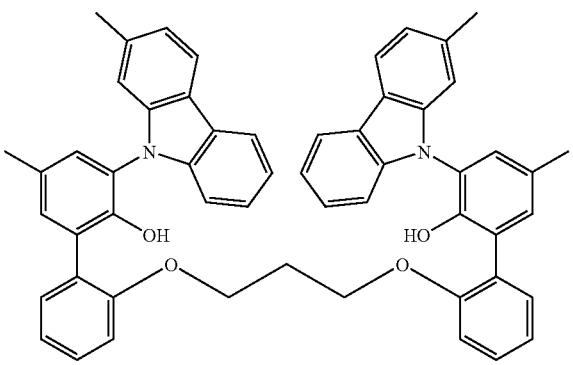

-continued
LL18
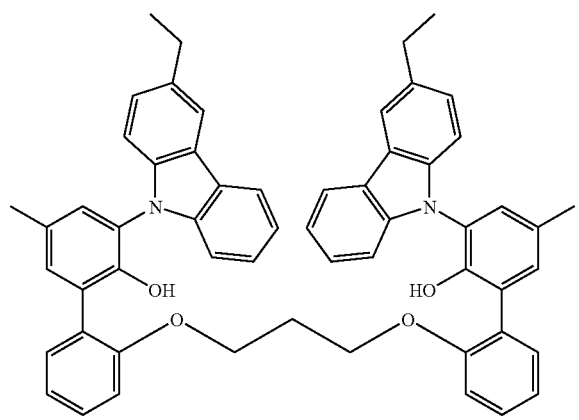
LL19
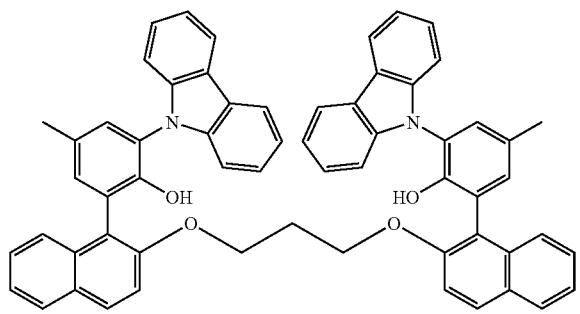
LL20
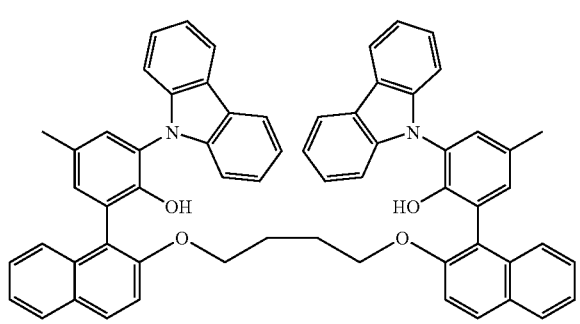
LL21
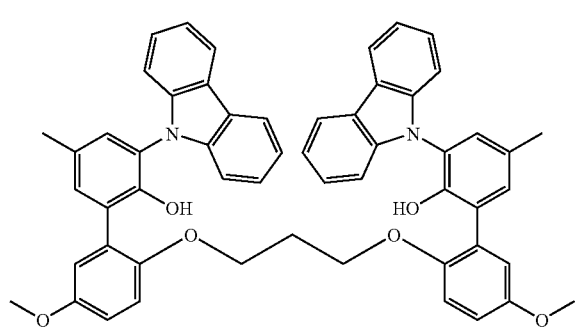
-continued
LL22
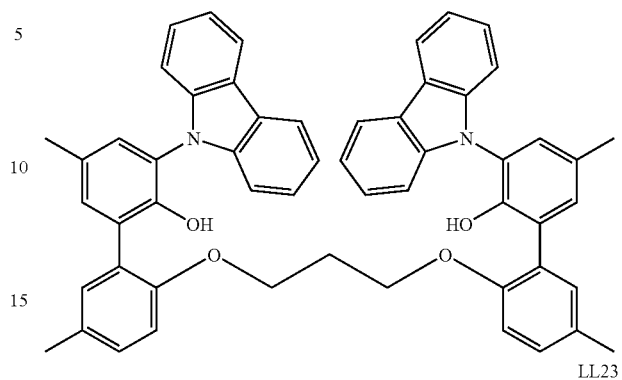
LL23
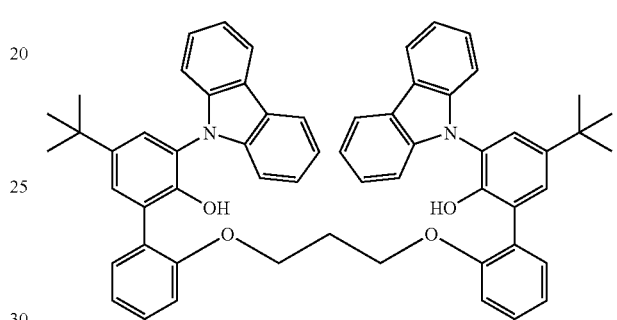
LL24
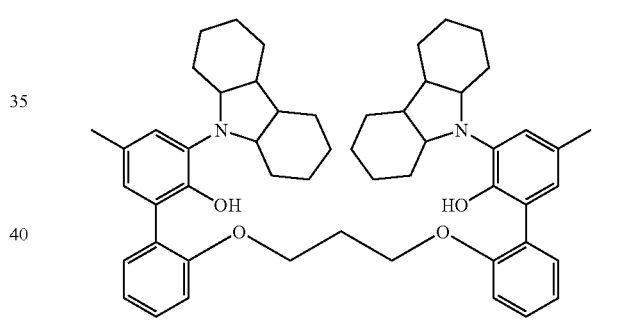
Scheme B2: Synthesis of (O,O)-Bridged Ligand via Upper Phenyl Ring/ Lower Phenyl Ring Double Suzuki or Negishi Cross Coupling Reactions
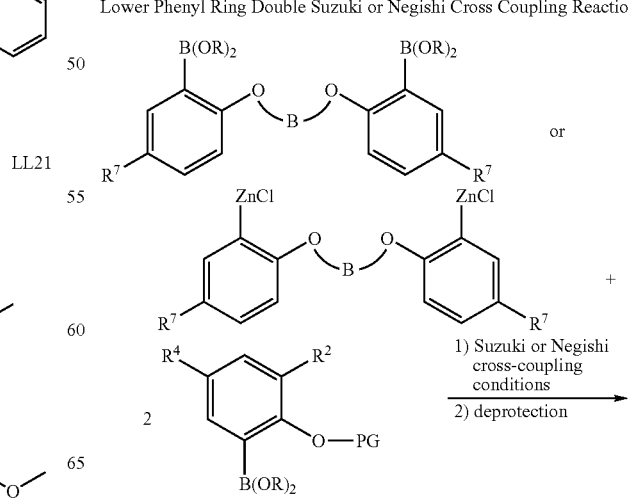

-continued

Example 18

Ligand LL25

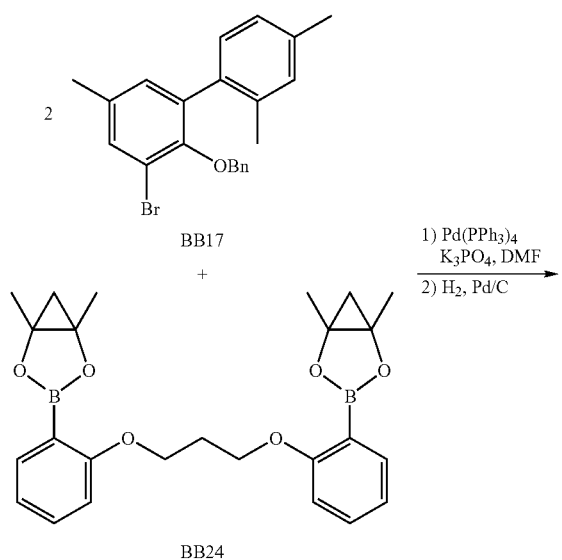

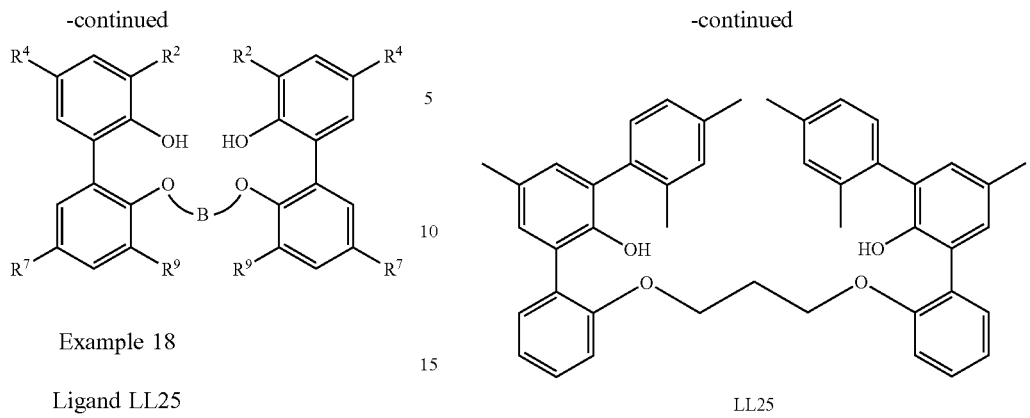

-continued

LL25

A mixture of the 2-bromophenol benzyl ether BB 17 (319 mg, 0.84 mmol), the diboronic ester BB24 (604 mg, 1.26 mmol), K$_3$PO$_4$ (318 mg, 1.5 mmol) and DMF (5 mL) was degassed with argon. Pd(PPh$_3$)$_3$ (230 mg, 0.2 mmol, 10 mol %) was added and the resulting mixture was stirred at 85° C. for 16 h under argon. After removal of the solvent in vacuo, the crude mixture was purified by flash chromatography to give 80 mg of the bridged intermediate. After stirring the benzyl ether intermediate under an atmosphere of H$_2$ (500 psi) in the presence of Pd/C (20 mg, 5%, Aldrich) in THF (1 mL) and EtOH (1 mL) at 50° C. for 2 h, the product was purified by flash chromatography (Ethylacetate/hexane=1/10) to give 34 mg of the product LL25. $^1$H NMR (300 MHz, CDCl$_3$): 7.32 (dd, J=7 Hz, 1 Hz, 2H), 7.21 (td, J=7.5 Hz, 1 Hz, 2H), 6.9–7.13 (m, 12H), 6.76 (d, J=7.5 Hz, 2H), 5.54 (s, 2H), 4.01 (t, J=6 Hz, 4H), 2.37 (s, 6H), 2.31 (s, 6H), 2.13 (s, 6H), 2.03–2.5 (m, 2H).

Scheme B3: Synthesis of (O,O)-Bridged Ligand via (O,O)-Bridged Bis(Aryl Bromide)

Step 1

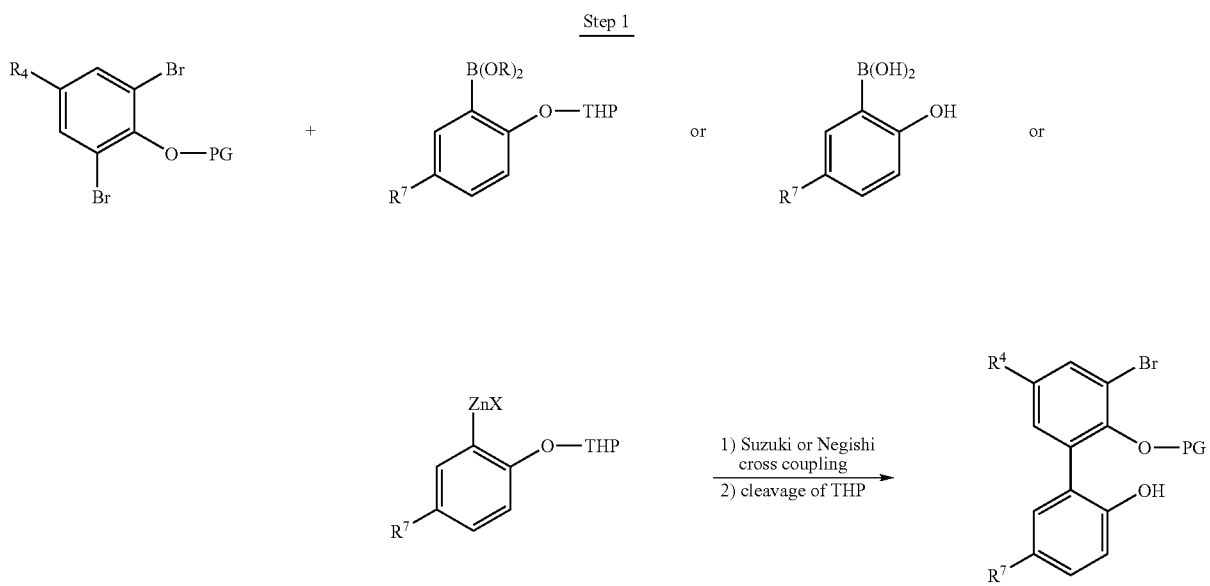

-continued

Step 2

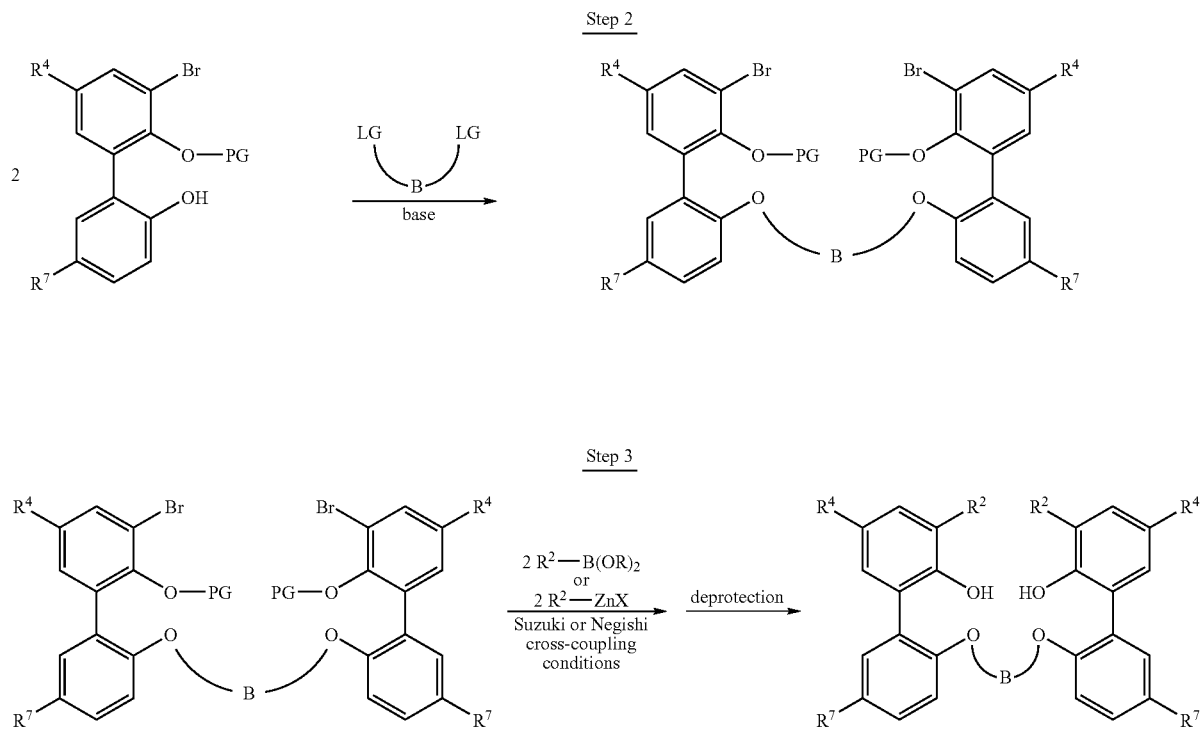

Step 3

Example 19

Detailed Example of 2-Br Substituted, Upper-ring Protected, Lower Ring Deprotected Building Block Synthesized According to Scheme B3, Step 1

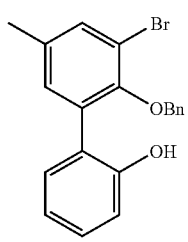

To a solution of 690 mg (5.0 mmol) of 2-bromophenol-6-boronic acid and 1.70 g (4.95 mmol) of 2,6-dibromo-4-methylphenol benzyl ether in 15 mL of degassed dme was added 289 mg (0.25 mmol, 5 mol %) Pd(PPh$_3$)$_4$ and 3.2 mL of degassed 2.0 M aq. Na$_2$CO$_3$. After heating to 80° C. for 4 h, the reaction mixture was cooled to RT and poured into ether. Isolation and concentration of the organic layer, followed by column chromatography (silica gel, 10% ethyl acetate/hexanes eluent), provided 604 mg (33%) of pure product as a white solid. $^1$H NMR (300 MHz, CDCl$_3$): 2.41 (s, 3H); 4.72 (s, 2H); 6.73 (s, 1H); 7.0–7.6 (overlapping multiplets, 11H).

Example 20

Detailed Example of Bridged, Upper-ring 2-Br Substituted Building Block Synthesized According to Scheme B3, Step 2

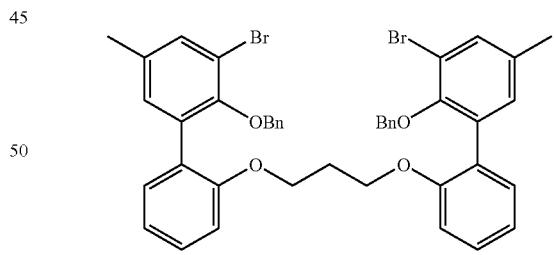

To a solution of 604 mg (1.64 mmol) of 2-bromo-4-methyl-6-(2-hydroxyphenyl)phenol benzyl ether and 315 mg (0.82 mmol) of 1,3-propanediol di-p-tosylate in 10 mL of acetone was added 1.11 g (3.3 mmol) of Cs$_2$CO$_3$. After stirring at RT for 16 h, the soln. was filtered and the volitiles were removed. Column chromatography (silica gel, 10% ethyl acetate/hexanes eluent) provided 221 mg (35%) of the product as a white solid. $^1$H NMR (300 MHz, CDCl$_3$): 1.96 (m, 2H); 2.35 (s, 6H); 3.91 (t, 4H); 4.52 (s, 4H); 6.8–7.6 (overlapping multiplets, 22H).

Example 21

Detailed Example of a Ligand Synthesized According to Scheme B3, Step 3

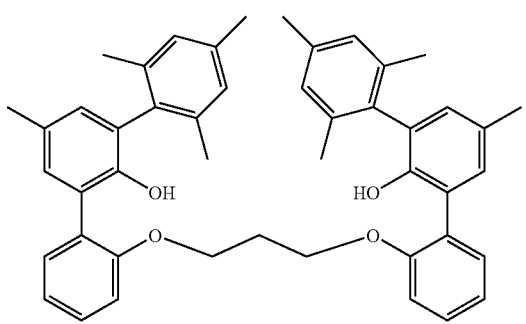

To a solution of 100 mg (0.13 mmol) of the dibromo building block described in Example 20 above dissolved in 5 mL of degassed dme was added 84 mg (0.51 mmol) of 2,4,6-trimethylphenylboronic acid, 15 mg (0.013 mmol, 10 mol %) of Pd(PPh$_3$)$_4$ and 150 µL of degassed 2.0 M aq. Na$_2$CO$_3$. After heating to 85° C. for 16 h, the reaction mixture was cooled to RT and poured into ether. Isolation and concentration of the organic layer, followed by column chromatography (silica gel, 5% ethyl acetate/hexanes eluent), provided 48 mg (42%) of the dibenzyl protected product as a white solid. $^1$H NMR (CDCl$_3$): 1.88 (m, 2H); 2.10 (s, 12H); 2.34 (s, 6H); 2.35 (s, 6H); 3.81 (t, 4H); 4.21 (s, 4H); 6.3–7.6 (overlapping multiplets, 26H).

After hydrogenation (200 psi H$_2$, 50° C.) of the dibenzyl product in 5 mL of 1:1 EtOAc/EtOH with 50 mg 5% Pd/C catalyst for 3 h, purification by column chromatography (silica gel, 10% ethyl acetate/hexanes eluent) gave 27 mg (71%) of the ligand. $^1$H NMR (300 MHz, CDCl$_3$): 2.0–2.1 (overlapped peaks, 14H); 2.30 (s, 6H); 2.34 (s, 6H); 4.02 (t, 4H); 5.40 (s, 2H); 6.7–7.6 (overlapping multiplets, 16H).

Example 22

Additional Example of a Ligand Synthesized According to Scheme B3, Step 3

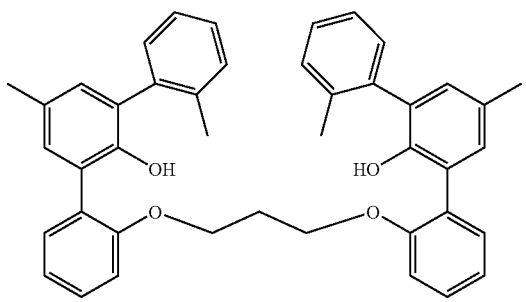

Solutions of 141 µL of 2 M o-tolMgBr in THF and 141 µL of 0.5 M ZnCl$_2$ in THF were combined in 1 mL of anhydrous THF and allowed to react at RT for 1 h. To this solution was added 55 mg (0.13 mmol) of the dibromo building block described in Example 20 above, and 1.0 mg (0.003 mmol, 2 mol %) of Pd(P$^t$Bu$_3$)$_2$. The mixture was diluted with 2 mL of THF and 1 mL of NMP, sealed, and heated to 80° C. for 2 h. After cooling to RT, the THF was removed in vacuo and the product was diluted with ether and washed with saturated brine. Isolation and concentration of the organic layer, followed by column chromatography (silica gel, 5% ethyl acetate/hexanes eluent), provided 39 mg (69%) of the dibenzyl protected product as a white solid. $^1$H NMR (CD$_2$Cl$_2$): 1.97 (m, 2H); 2.18 (s, 6H); 2.35 (s, 6H); 3.91 (m, 4H); 4.19 (s, 4H), 6.45 (d, 4H); 6.7–7.5 (overlapping multiplets, 26H).

After hydrogenation (100 psi H$_2$, 40° C.) of the dibenzyl product in 5 mL of 1:1 EtOAc/EtOH with 50 mg 5% Pd/C catalyst for 3 h, purification by column chromatography (silica gel, 10% ethyl acetate/hexanes eluent) gave 23 mg (77%) of the ligand. $^1$H NMR (300 MHz, CD$_2$Cl$_2$): 1.85 (m, 2H); 2.20 (s, 6H); 2.31 (s, 6H); 4.10 (t, 4H); 5.32 (s, 2H); 6.7–7.6 (overlapping multiplets, 20H).

Part C: Synthesis of (S,S)-Bridged Bis(Biphenylphenol) Ligands:

Scheme C1:

Step 1

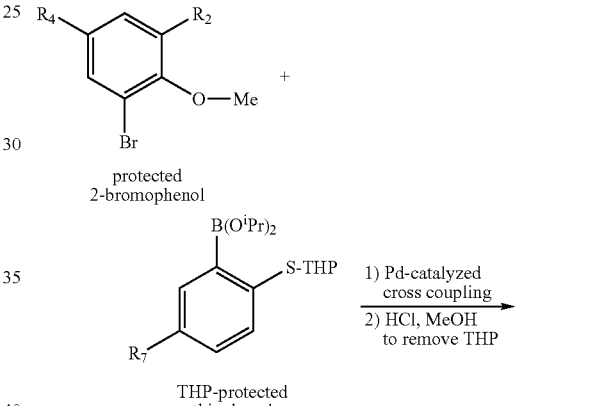

Step 2

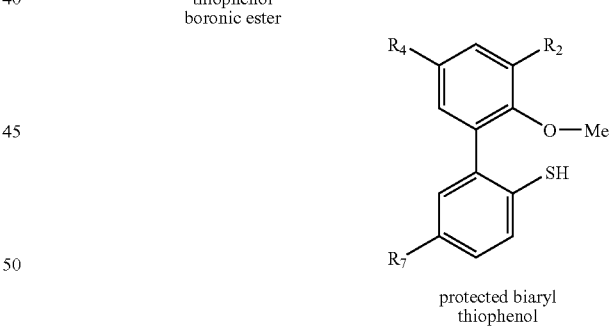

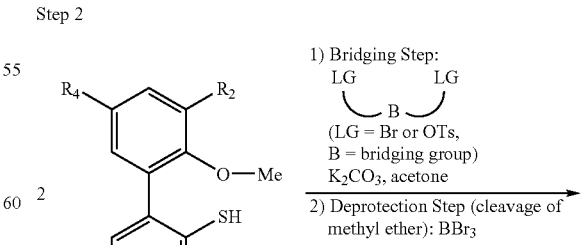

-continued

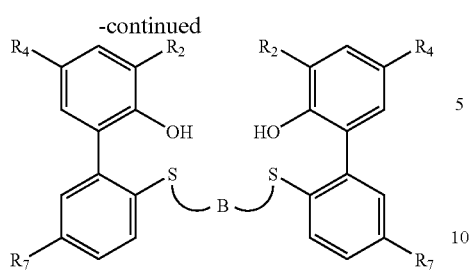

Example 23

A Biaryl Thiophenol Building Block Synthesized According to Scheme C1 Step 1

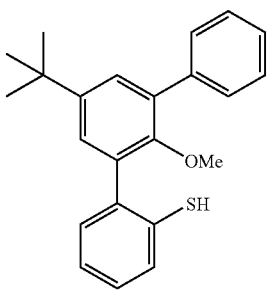

BB30

A mixture of the S-THP protected boronic acid building block BB21 (7 mmol), the protected 2-bromophenol BB14 (5 mmol, 1.6 g), Na$_2$CO$_3$ (4 mL of a 2 M solution in water, 8 mmol) and dimethoxy ethane (15 mL) was degassed with argon (10 min). Pd(PPh$_3$)$_3$ (280 mg, 0.25 mmol, 5%) was added and the resulting mixture was stirred at 85° C. for 16 h under argon. Ethyl acetate (EA, 15 mL) was added and the mixture was dried over Na$_2$SO$_4$. After filtration, the solvent was removed and the residue was dissolved in CH$_2$Cl$_2$ (10 mL). HCl (1 mL, 37%) was added and the resulting mixture was stirred at 40° C. for 2 h. Brine was added and the mixture was extracted with ethyl acetate, dried over Na$_2$SO$_4$, and purified by flash chromatography (Ethylacetate/hexane=1/10) to give 1.4 g of the product BB30 (4 mmol, 80% yield). $^1$H NMR (300 MHz, CDCl$_3$): 7.58–7.63 (d br, J=7 Hz, 2H), 7.30–7.42 (m, 6H), 7.19–7.25 (m, 3H), 3.49 (s, 1H), 3.14 (s, 3H), 1.33 (s, 9H).

Example 24

A bis aryl Building Block Synthesized According to Scheme C1 Step 1

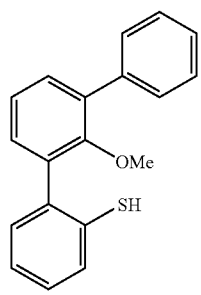

BB31

According to Scheme C1 Step1, the compound BB31 was synthesized in about 50% yield. $^1$H NMR (300 MHz, CDCl$_3$): 7.56–7.63 (d br, J=7 Hz, 2H), 7.38–7.45 (m, 4H), 7.25–7.35 (m, 2H), 7.18–7.25 (m, 4H), 3.47 (s, 1H), 3.17 (s, 3H).

Example 25

A Ligand Synthesized According to Scheme C1 Step 2

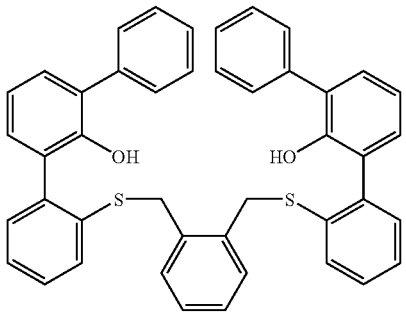

LL26

A mixture of the biaryl thiophenol building block BB31 (55 mg, 0.188 mmol), the corresponding dibromide (α,α'-dibromo-o-xylene, 25 mg, 0.094 mmol), and K$_2$CO$_3$ (55 mgs, 0.4 mmol) in acetone (2 mL) was stirred at 60° C. for 4 hours. After filtration, the solvent was removed and the residue was dissolved in CH$_2$Cl$_2$ (3 mL). BBr$_3$ (1.5 mL of a 1 M solution in CH$_2$CL$_2$, 1.5 mmol) was added and the resulting mixture was stirred at room temperature for 2 h. Brine was added and the mixture was extracted with ethyl acetate, dried over Na$_2$SO$_4$, and purified by flash chromatography (Ethylacetate/hexane=1/10) to give 46 mg of the product LL26 (0.07 mmol, 75% yield). $^1$H NMR (300 MHz, CDCl$_3$): 7.50–7.55 (d br, J=7 Hz, 4H), 7.41–7.48 (t br, J=7 Hz, 4H), 7.30–7.38 (m, 4H), 7.23–7.29 (m, 8H), 6.98–7.08 (m, 8H), 3.95 (m, 4H).

Additional ligands that are synthesized in a manner similar to that described in Scheme C1:

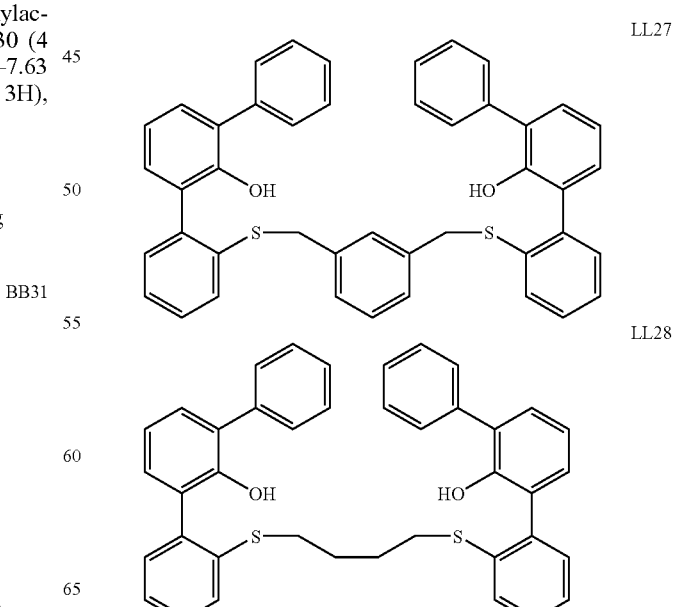

-continued
LL29
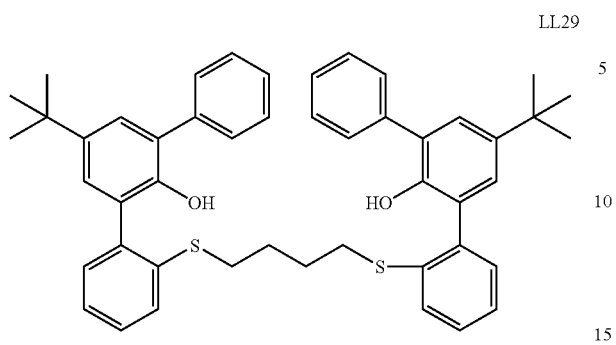
LL30
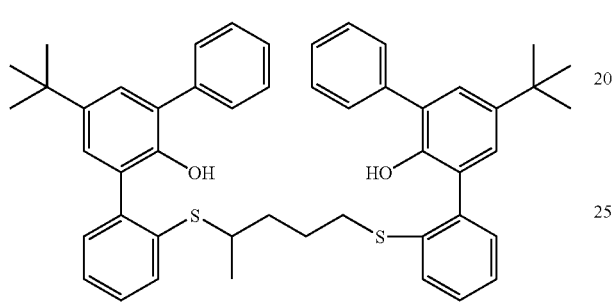
LL31
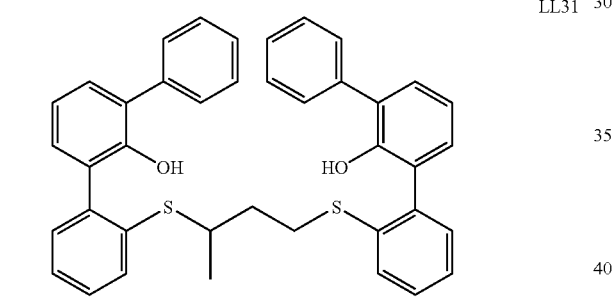
LL32
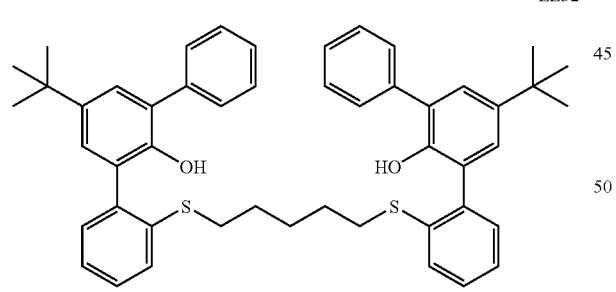
LL33
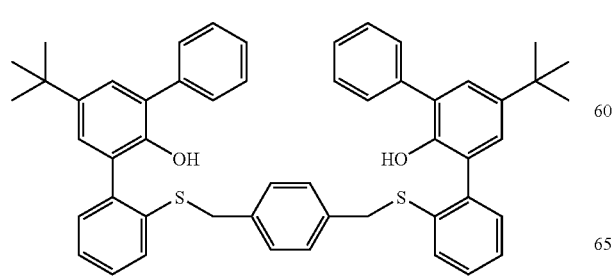
-continued
LL34
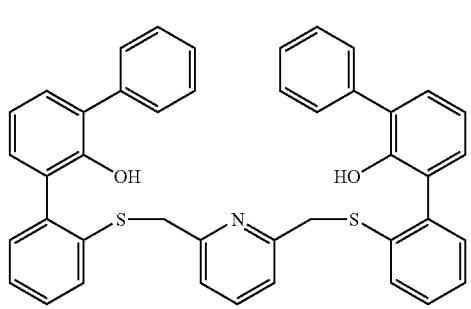
LL35
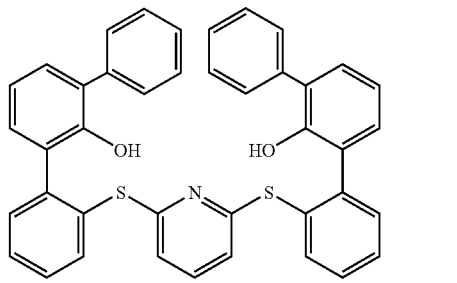
LL36
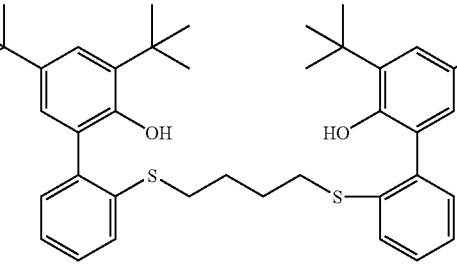
LL37
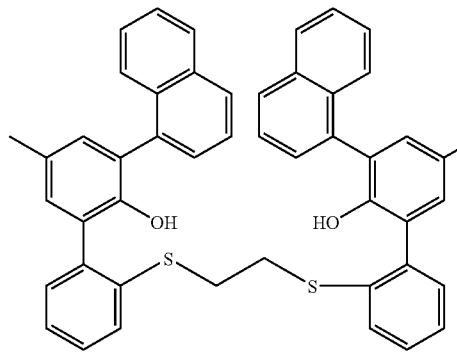
LL38
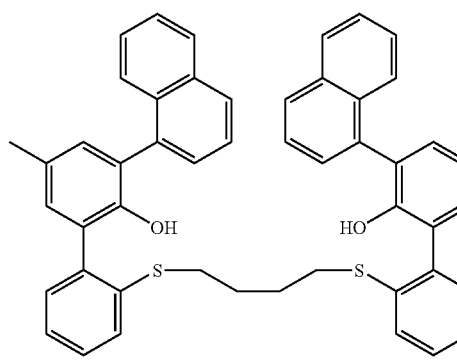

-continued

LL39

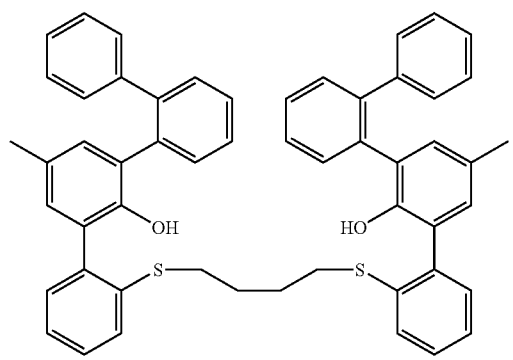

LL40

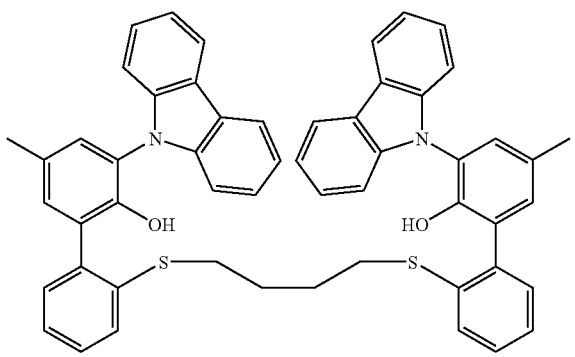

LL41

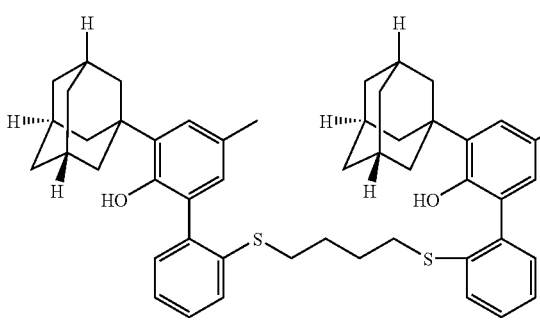

Scheme C2:

Step 1

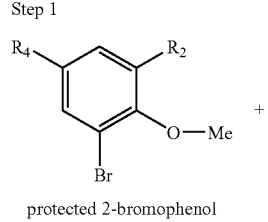

protected 2-bromophenol

-continued

1) Pd-catalyzed cross coupling
2) HCl, MeOH to remove THP

THP-protected thiophenol boronic ester protected biaryl thiophenol

Step 2

1) Bridging Step:
Br⌒B⌒Br
Pd₂(dba)₃, xanphos, NaOtBu
2) Deprotection Step (cleavage of methyl ether): BBr₃ protected biaryl thiophenol

Example 26

A Ligand Synthesized According to Scheme C2 Step 2

LL42

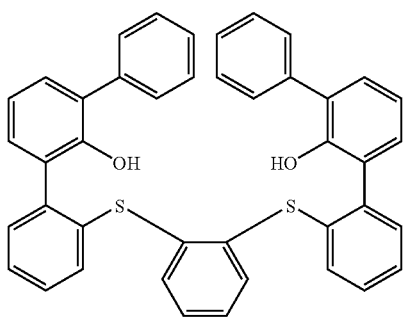

A mixture of the protected bis aryl thiophenol (BB31) (104 mg, 0.356 mmol), the corresponding dibromide (1,2-dibromobenzene, 42 mg, 0.178 mmol), NaOtBu (48 mg, 0.5 mmol) in degassed toluene (2 mL) was added to a solution of Pd(dba)$_2$ (20 mg, 0.036 mmol, 10%) and Xantphos (41 mg, 0.712 mmol, 20%), and the resulting mixture was stirred at 110° C. for 16 h under argon. After filtration, the solvent was removed and the residue was dissolved in CH$_2$Cl$_2$ (5 mL). BBr$_3$ (2 mL of a 1 M solution in CH$_2$CL$_2$, 2 mmol) was added and the resulting mixture was stirred at room temperature for 2 h. Brine was added and the mixture was extracted with ethylacetate, dried over Na$_2$SO$_4$, and purified by flash chromatography (ethylacetate/hexane=1/10) to give 57 mg of the product LL42 (0.091 mmol, 51% yield). $^1$H NMR (300 MHz, CDCl$_3$): 7.15–7.45 (m, 14H), 7.05–7.15 (m, 8H), 6.90 (t, J=7.5 Hz, 2H), 4.04 (s, 2H).

Additional ligands that are synthesized in a manner similar to that described in Scheme C2:

According to Scheme C1 Step 2, the thiophenol building block BB31 (38 mg, 0.13 mmol), the corresponding dibromide (2-bromobenzylbromide, 33 mg, 0.13 mmol), and K$_2$CO$_3$ (110 mgs, 0.8 mmol) in acetone (2 mL) was stirred at 60° C. for 2 hours. After workup and cleavage of the methyl ethers, and purification 54 mg of the intermediate were isolated (0.117 mmol, 90%). According to Scheme C2 Step 2, a mixture of the thiophenol building block BB31 (34 mg, 0.117 mmol), the intermediate (54 mg, 0.117 mmol), NaOtBu (20 mg, 0.2 mmol), Pd(dba)$_2$ (3 mgs, 0.006 mmol), and Xantphos (6 mg, 0.012 mmol) in toluene (2 mL) was stirred at 110° C. for 16 hours. After workup and cleavage of the methyl ethers, and purification 88 mg of the ligand LL45 was isolated (0.101 mmol, 54%). $^1$H NMR (300 MHz, CDCl$_3$) (dimethyl ether!): 7.55–7.62 (m, 4H), 7.30–7.42 (m, 12H), 7.22–7.28 (m, 2H), 7.12–7.25 (m, 8H), 7.01–7.11 (m, 4H), 4.12 (m, 2H), 3.10 (s, 3H), 3.05 (s, 3H).

LL43

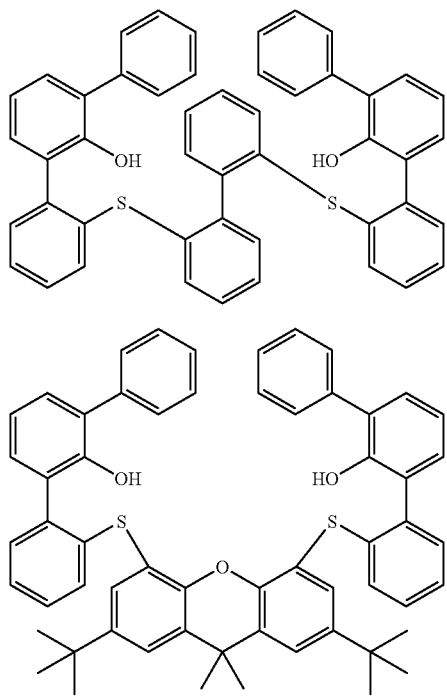

LL44

Example 27

A Ligand Synthesized by Combining Schemes C1 and C2

LL45

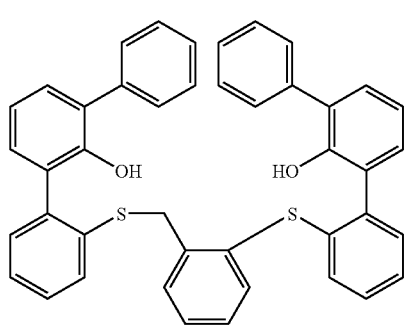

Scheme C3:

Step 1

Step 2

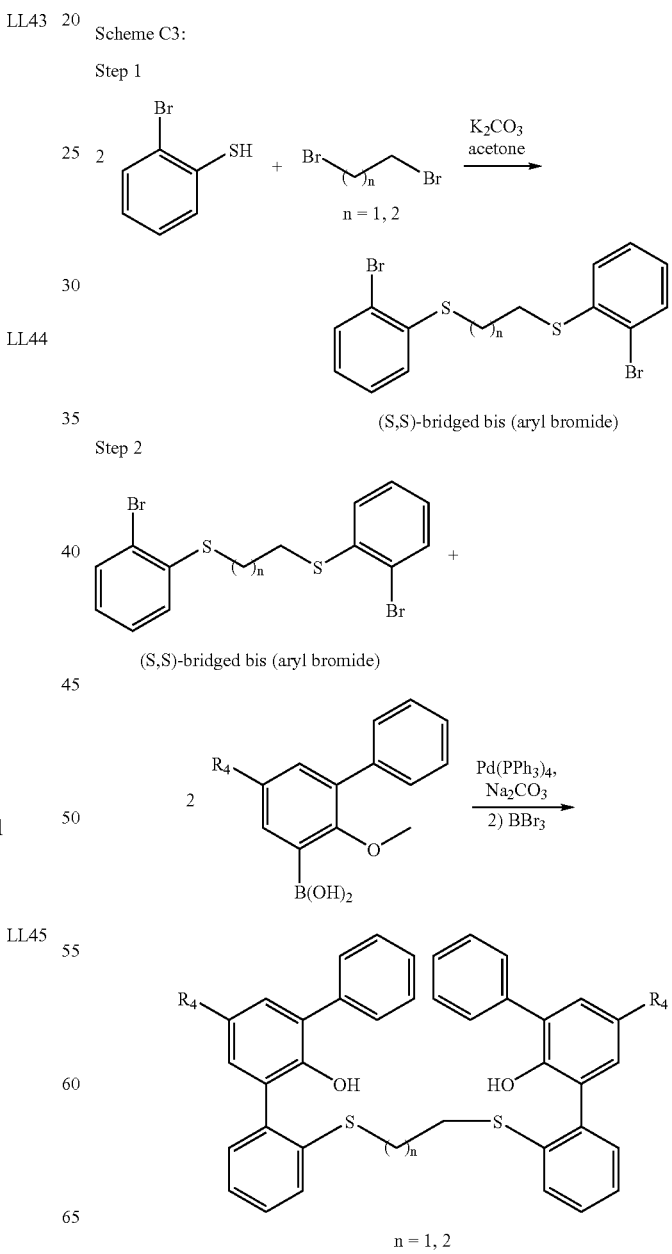

(S,S)-bridged bis (aryl bromide)

(S,S)-bridged bis (aryl bromide)

n = 1, 2

Example 28

A Ligand Synthesized According to Scheme C3

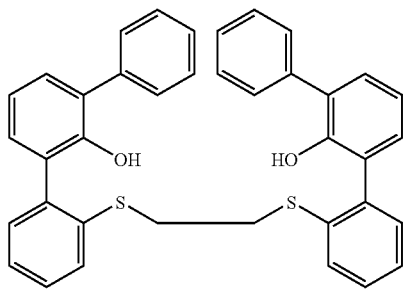

LL46

A mixture of the boronic acid (0.8 mmol), the (S,S)-bridged bis(aryl bromide) (0.4 mmol, 161 mg, prepared as shown above), $Na_2CO_3$ (0.5 mL of a 2 M solution in water, 1.5 mmol) and dimethoxy ethane (5 mL) was degassed with argon (10 min). $Pd(PPh_3)_4$ (92 mg, 0.08 mmol, 20%) was added and the resulting mixture was stirred at 85° C. for 16 h under argon. Ethyl acetate (15 mL) was added and the mixture was dried over $Na_2SO_4$. After filtration, the solvent was removed and the residue was dissolved in $CH_2Cl_2$ (10 mL). $BBr_3$ (2 mL of a 1 M solution in $CH_2CL_2$, 2 mmol) was added and the resulting mixture was stirred at room temperature for 2 h. Brine was added and the mixture was extracted with EA, dried over $Na_2SO_4$, and purified by flash chromatography (Ethylacetate/hexane=1/10) to give 37 mg of the product LL46 (0.06 mmol, 15% yield). $^1$H NMR (300 MHz, $CDCl_3$): 7.52–7.58 (d br, J=7 Hz, 4H), 7.41–7.48 (t br, J=7 Hz, 4H), 7.23–7.39 (m, 12H), 6.98–7.12 (m, 4H), 5.10 (s, 2H), 2.85 (s, 4H).

Additional ligands that are synthesized in a manner similar to that described in Scheme C3:

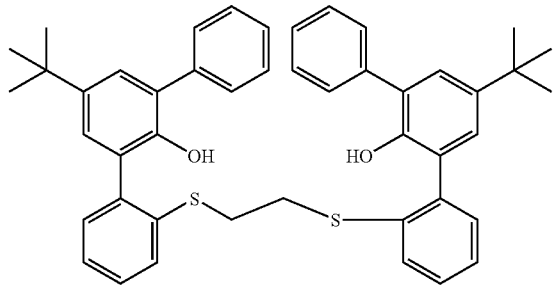

LL47

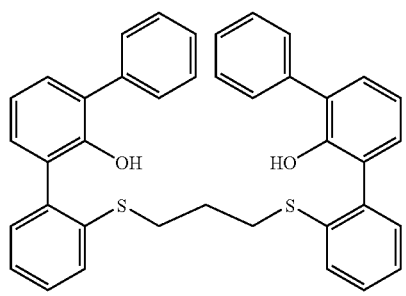

LL48

Part D:

Example 29

Synthesis of (O,S)-Bridged Bis(Biphenylphenol) Ligands

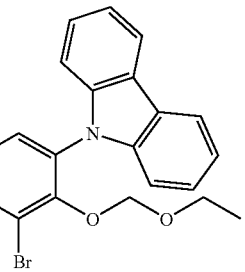

MOM ether protected 2-bromophenol

+

2 eq.

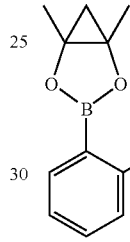   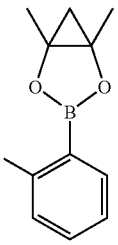

1) $Pd(PPh_3)_4$
$K_3PO_4$,
DMF
2) $H_2$, Pd/C

BB25

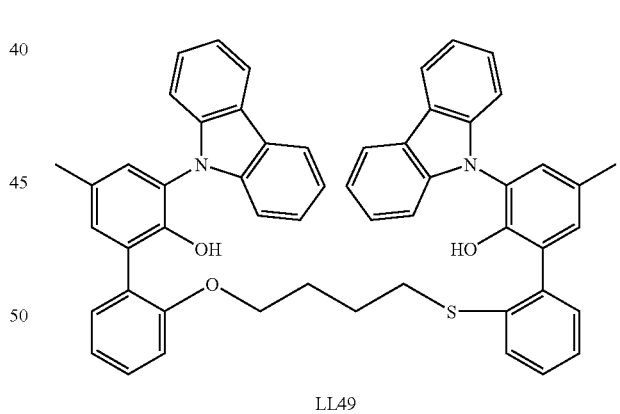

LL49

A mixture of the MOM ether protected 2-bromophenol (176 mg, 0.43 mmol), the diboronic ester BB25 (110 mg, 0.216 mmol), $K_3PO_4$ (150 mg, 0.7 mmol) and DMF (2 mL) was degassed with argon. $Pd(PPh_3)_4$ (46 mg, 0.04 mmol) was added and the resulting mixture was stirred at 85° C. for 16 h under argon. After removal of the solvent in vacuo, the crude mixture was purified by flash chromatography to give 81 mg of the intermediate. After cleavage of the MOM ether (HCl, THF, MeOH) and purification, 40 mg of the product LL49 was obtained (0.05 mmol, 23% yield). $^1$H NMR (300 MHz, $CDCl_3$): 8.10 (d, J=7.5 Hz, 4H), 7.15–7.45 (m, 21H), 7.05–7.12 (m, 2H), 6.88 (d, J=8.5 Hz, 1H), 6.01 (s, 1H), 4.89

(s, 1H), 3.95 (t, J=6 Hz, 2H), 2.75 (t, J=7 Hz, 2H), 2.37 (s, 3H), 2.32 (s, 3H), 1.75–1.85 (m, 2H), 1.60–1.70 (m, 2H).

Part E: Synthesis of (N,N)-Bridged Bis(Biphenylphenol) Ligands:

Example 30

Synthesis of bis aryl building blocks BB32 and BB33

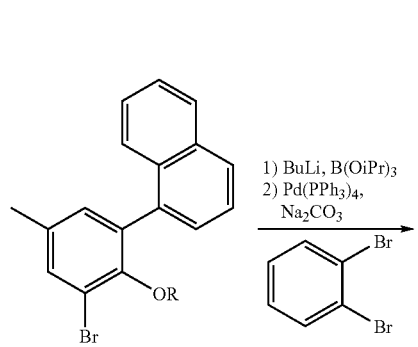

n-BuLi (2.6 mmol, from a 1.6 M solution in hexanes) was added slowly to a solution of the benzyl ether protected 2-bromophenol (2.47 mmol) in THF (5 mL, anhydrous) at −78° C. under an atmosphere of argon. After stirring for 10 min at that temperature, triisopropyl borate (645 µL, 2.8 mmol) was added slowly and the temperature was allowed to come to room temperature (30 min). After stirring for another 30 min, the solvent was removed and the crude boronic acid was used without further purification. A mixture of the boronic acid (750 mg, 2.5 mmol), 1,2 dibromobenzene (2.36 g, 10 mmol), $Na_2CO_3$ (2 mL of a 2 M solution in water, 4 mmol) and dimethoxy ethane (15 mL) was degassed with argon. $Pd(PPh_3)_3$ (144 mg, 0.125 mmol, 10%) was added and the resulting mixture was stirred at 85° C. for 16 h under argon. Ethyl acetate (30 mL) was added and the mixture was dried over $Na_2SO_4$. After filtration, the crude product was purified by flash chromatography (ethylacetate/hexane=1/10) to give 762 mg of the benzyl ether product BB32 (1.6 mmol, 65% yield). The methyl ether product BB33 was prepared similarly.

Example 31

Synthesis of (NH,NH)-Bridged Biaryl Phenyl Methyl Ether Ligand

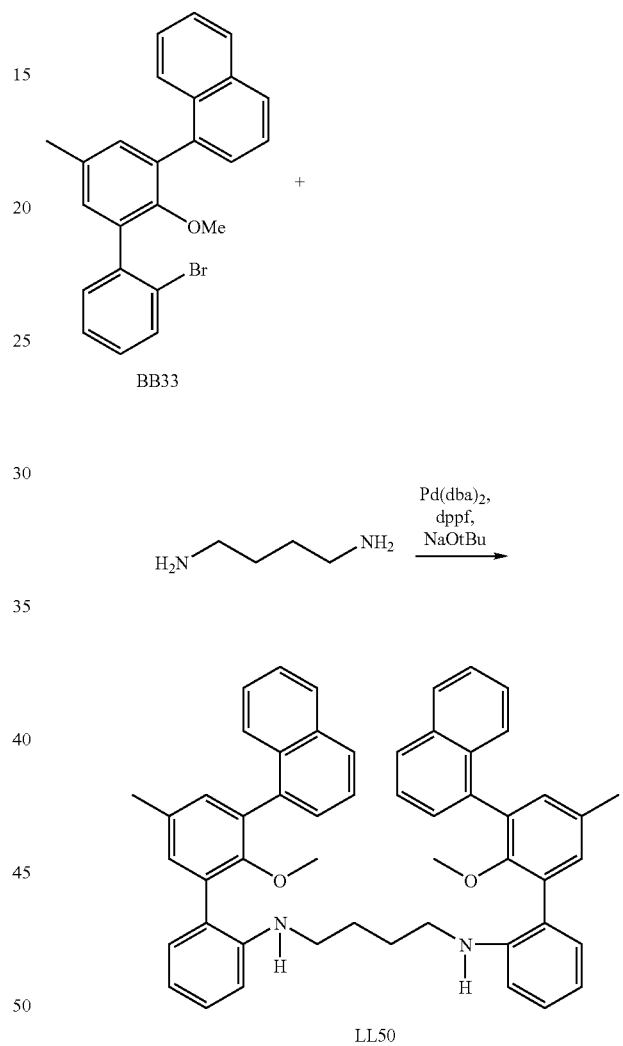

A mixture of the methyl ether building block BB33 (140 mg, 0.348 mmol), 1,4-diaminobutane (15 mg, 0.174 mmol), NaOtBu (48 mg, 0.5 mmol) and toluene (2 mL) was degassed with argon. $Pd(dba)_2$ (9 mg, 0.015 mmol) and dppf (1,1'-bis(diphenylphosphino)ferrocene, 17 mg, 0.03 mmol) were added and the resulting mixture was stirred at 100° C. for 16 h under argon. After removal of the solvent in vacuo, the crude mixture was purified by flash chromatography to give 51 mg of the product LL50 (0.068 mmol, 39% yield). $^1$H NMR (300 MHz, CDCl$_3$): 7.82–7.90 (m, 4H), 7.61–7.79 (m, 2H), 7.32–7.55 (m, 8H), 7.21–7.29 (m, 4H), 7.09–7.19 (m, 4H), 6.65–6.89 (m, 4H), 3.90–4.05 (m, 2H), 3.05–3.15 (m, 4H), 2.95 (t, 6H), 2.33 (s, 6H), 1.62–1.80 (m, 4H).

Example 32

Synthesis of (NMe,NMe)-bridged Biaryl Phenol Ligand LL51

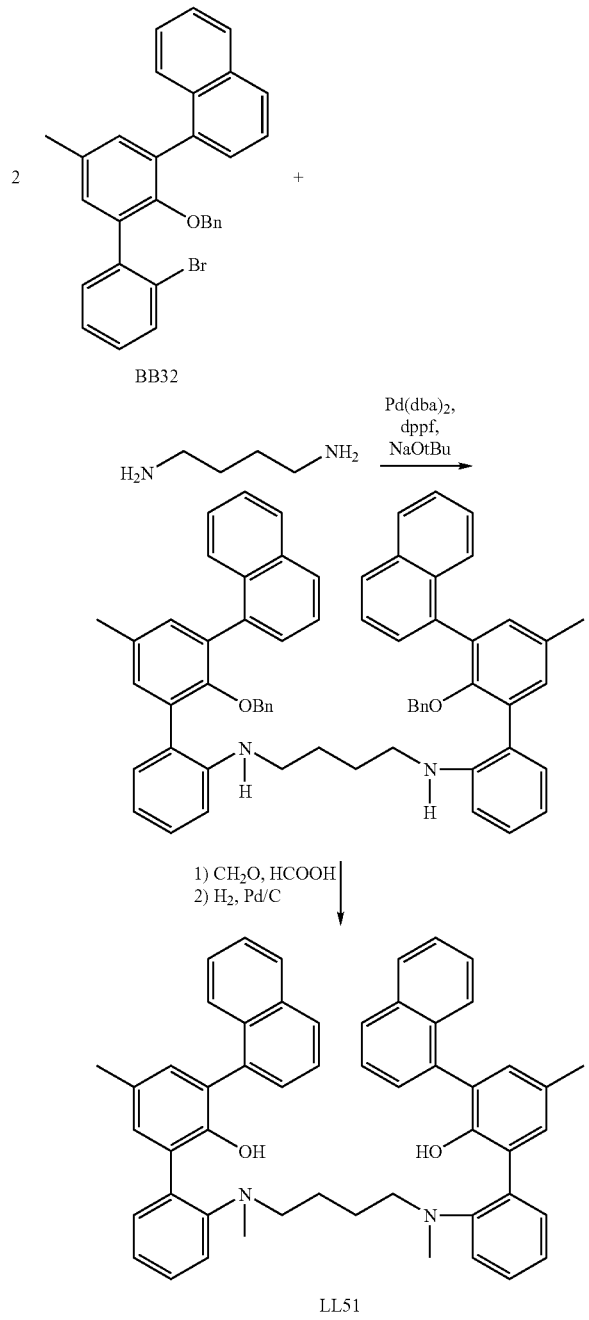

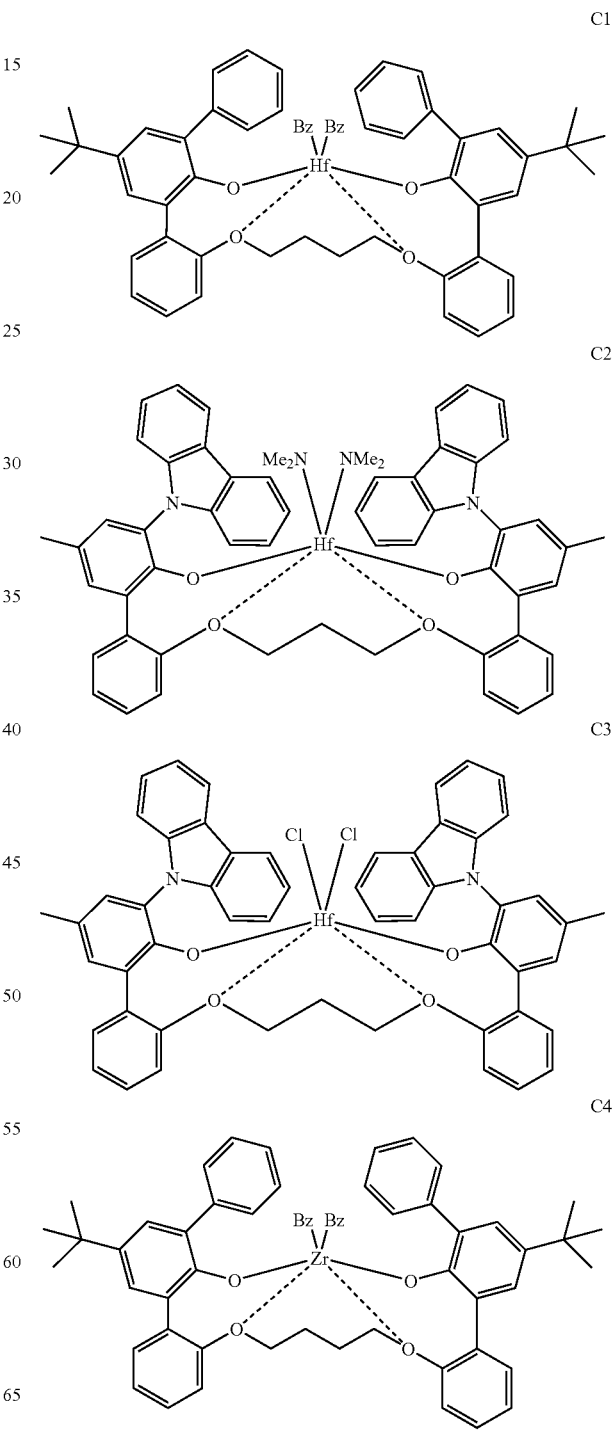

A mixture of the substituted phenylbromide (benzyl ether, BB32, 133 mg, 0.278 mmol), 1,4-diaminobutane (12 mg, 0.139 mmol), NaOtBu (48 mg, 0.5 mmol) and toluene (2 mL) was degassed with argon. Pd(dba)$_2$ (9 mg, 0.015 mmol) and dppf (17 mg, 0.03 mmol) were added and the resulting mixture was stirred at 100° C. for 16 h under argon. After removal of the solvent in vacuo, the crude mixture was purified by flash chromatography to give 31 mg of the intermediate. A mixture of this intermediate with formic acid (0.5 mL) and paraformaldehyde (0.5 mL of a 37% solution in H$_2$O) was stirred for 30 min at 80° C. Na$_2$CO$_3$ (5 mL of a 2M aq. Solution) was added and the mixture was extracted with ethyl acetate. After stirring the benzyl ether intermediate under an atmosphere of H$_2$ (500 psi) in the presence of Pd/C (50 mg, 5%, Aldrich) in EA (1 mL), EtOH (1 mL) at 50° C. for 2 h, the crude product was purified by flash chromatography to give 15 mg of the product LL51. $^1$H NMR (300 MHz, CDCl$_3$): 10.23 (s, 2H), 7.82 (t, 4H), 7.62 (d, 2H), 6.42–7.52 (m, 4H), 7.15–7.41 (m, 14H), 7.08 (t, 2H), 7.02 (d, 2H), 2.42–2.60 (m, 10H), 2.30 (s, 3H), 2.25 (s, 3H), 1.42–1.12 (m, 4H).

Complexes used in some of the examples:

-continued

C5
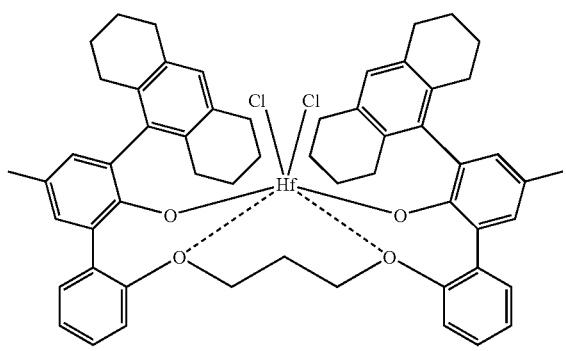

C6
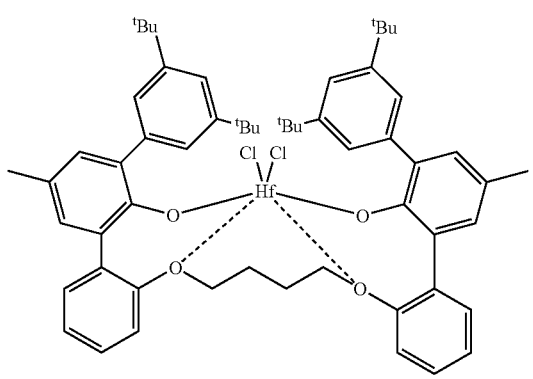

C7
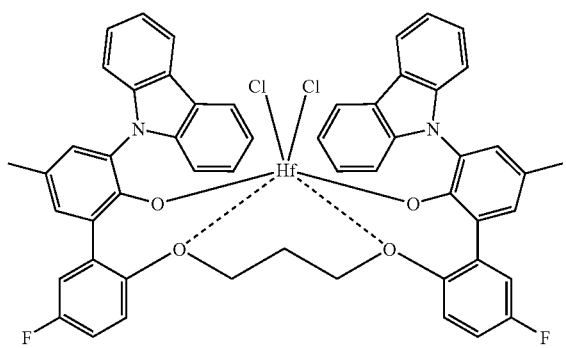

Example 33

Synthesis of Complex C1

46.3 mg (67 mmol) LL1 in 6 mL toluene were combined with 36.3 mg (67 mmol) of HfBz$_4$ in 6 mL toluene. The mixture was stirred for 10 min and slowly concentrated by removing the solvent with a stream of inert gas. A white solid material was isolated. The 1H-NMR is consistent with one symmetrical compound. The $^1$H-NMR spectrum indicates the presence of toluene in the isolated product. 1H-NMR in C$_6$D$_6$ (δ in ppm): aromatic protons: 7.83 (d), 7.6–6.5 (m), 6.05 (d) bridge CH$_2$—O— protons 4.1 (m), 3.6 (m) Hf-CH$_2$Ph protons: 2.21 (d), 1.1 (d) $^t$Bu protons: 1.24 (s), bridge CH$_2$—CH$_2$—O— protons 0.83 (m), 0.45 (m).

Example 34

Synthesis of Complex C2

50 mg (64.85 mmol) LL5 and 23 mg Hf(NMe$_2$)$_4$ were combined in 8 mL toluene. The reaction mixture was placed in sand bath at 60–70° C. After 1 hour, a stream of Ar was used to remove the solvent. A dry white product was obtained. The 1H-NMR is consistent with a C2 symmetric bisamide complex and indicates the presence of toluene in the isolated product. 1H-NMR in C$_6$D$_6$ (δ in ppm): 8.39 (d), 8.09 (d), 7.5–6.6 (m), 5.02 (d), 3.8 (m), 3.25 (m), 2.15 (s), 1.82 (s), 1.05 (m).

Example 35

Synthesis of Complex C3

64 mmol of complex C2 is dissolved in 5 mL toluene and 100 mg of Me$_3$Si—Cl was added. After reaction overnight, volatile products and the solvent were removed. The reaction mixture was taken up in 2 ml toluene and 400 ul Cl$_2$SiMe$_2$ were added. A white precipitate formed within 30 min. 31 mg (45%) of the bischloride complex 3 was isolated. The 1H-NMR is consistent with one C2 symmetric bischloride complex (on NMR timescale) and indicates the presence of toluene in the isolated product. 1H-NMR in CD$_2$Cl$_2$ (δ in ppm): 8.38 (d), 8.12 (d), 7.6–7.05 (m), 6.75 (m), 4.61 (d), 4.21 (m), 3.7 (m), 2.4 (s), 0.1.72 (m).

Example 36

Synthesis of Complex C3

31.4 mmol ligand LL5 is dissolved in 450 ul toluene. 31.6 mmol HfCl$_2$Bz$_2$.Et$_2$O is dissolved in 900 ul toluene and added to the ligand solution. The reaction mixture was placed in a sand bath at 70° C. for 1 hour. The reaction mixture was allowed to cool to room temperature overnight. The supernatant liquid was removed from the white solid product. The solid material was dried. Yield: 25 mmol (80%).

Example 37

Synthesis of Complex C4

37.6 mg (54 mmol) LL1 in 8 mL toluene was combined with 24.8 mg (54 mmol) of ZrBz$_4$ in 6 mL toluene. The mixture was stirred for 1–2 min and slowly concentrated by removing the solvent with a stream of inert gas. A pale yellow solid material was isolated. The $^1$H-NMR is consistent with one symmetrical compound. The $^1$H-NMR spectrum indicates the presence of toluene in the isolated product. $^1$H-NMR in C$_6$D$_6$ (δ in ppm): aromatic protons: 7.91 (d), 7.7–6.6 (m), 6.07 (d) bridge CH$_2$—O— protons 4.02 (m), 3.54 (m) Hf-CH$_2$Ph protons: 2.46 (d), 1.24 (d) tBu protons: 1.17 (s), bridge CH$_2$—CH$_2$—O— protons 0.86 (m), 0.51 (m).

Example 38

Synthesis of Complex C5

12.1 mg HfCl$_2$Bz$_2$.Et$_2$O (24 mmol) in 900 uL toluene was added to 20.4 mg LL6 (25 mmol) in 450 uL toluene. 150 uL toluene were added and the reaction mixture was placed in a sand bath at 80° C. for 1.5 hours. The solution was allowed to cool to room temperature. Colorless crystals formed which were isolated by decanting the supernatent liquid. Yield 14.4 mg (54%). $^1$H-NMR in $CD_2Cl_2$ ($\delta$ in ppm): 7.7–6.9 ppm (aromatic protons), 6.1 ppm (d), 4.25 (m), 4.05 (m), 3.1–2.6 (m), 2.6–2.05 (m), 2.05–1.3 (m). Single crystal X-ray analysis was performed. Crystallographic data: for C57H58Cl2HfO4, M=1056.42. Orthorombic crystal system, space group Pcca, unitcell dimentions: a=22.851(10) Å, b=14.984(5) Å, c=16.454 (7) Å, Z=4, Dc=1.253 mg/m$^3$, 15684 reflections collected. The structure was solved by by direct methods and refined by full-matrix least squares on $F^2$. The final refinement converged at $R_1$=0.0815 and $wR_2$=0.2011 for I>2$\sigma$ (I) and $R_1$=0.1561 and $wR_2$=0.2206 for all data. X-ray structure is shown in FIG. 1$a$ and 1$b$.

Example 39

Synthesis of Complex C6

16 mg $HfCl_2Bz_2$*$Et_2O$ (31.7 mmol) in 800 uL toluene was added to 26 mg (31.7 mmol) LL3 in 400 uL toluene. The reaction mixture was placed in a sand bath at 70° C. for 35 min. The reaction mixture was allowed to cool to room temperature over night and was cooled to –30° C. for 1 hour. The colorless crystalline material was separated from the solution and dried. Yield: 30 mg (87%). 1H-NMR in $CD_2Cl_2$ ($\delta$ in ppm): 7.64–7.02 ppm (aromatic protons), 4.62 (m), 3.94 (m), 2.36 (s), 1.40 (s), 1.20 (m).

Example 40

Synthesis of Complex C7

11.3 mg $HfCl_2Bz_2.Et_2O$ (22.3 mmol) in 500 uL toluene was added to 18 mg (22.3 mmol) LL52 in 300 uL toluene. The reaction mixture was placed in a sand bath at 70° C. for 90 min. The reaction mixture was allowed to cool to room temperature for 100 min and was cooled to –30° C. over night. The powdery crystalline material was separated from the solution and dried. Yield: 14.3 mg (61%). $^1$H-NMR in $CD_2Cl_2$ ($\delta$ in ppm): 8.36 (d), 8.12 (d), 7.5–7.0 ppm (aromatic protons), 4.44 (m), 4.52 (m), 4.15 (m), 3.67 (m), 2.40 (s), 1.7 (m).

Example 41

Propylene Polymerizations Using Metal-ligand Compositions. A Total of One Hundred and Eight (108) Separate Polymerization Reactions were Performed as Described Herein Preparation of the polymerization reactor prior to injection of catalyst composition: A pre-weighed glass vial insert and disposable stirring paddle were fitted to each reaction vessel of the reactor. The reactor was then closed, 0.10 mL of a 0.02 M solution of group 13 reagents in toluene and 3.9 mL of toluene were injected into each pressure reaction vessel through a valve. The identity of the group 13 reagent solution is given in Tables 1–3. The temperature was then set to the appropriate setting (with specific temperatures for each polymerization being listed in Tables 1–3, below), and the stirring speed was set to 800 rpm, and the mixture was exposed to propylene at 100 psi pressure. A propylene pressure of 100 psi in the pressure cell and the temperature setting were maintained, using computer control, until the end of the polymerization experiment.

In situ preparation of metal-ligand compositions: The following methods were employed to prepare the metal-ligand compositions as indicated in the Tables 1–3. Method A: An appropriate amount of ligand solution (10 mM in toluene) was dispensed in a 1 mL glass vial at a scale of 0.4–0.75 mmol. To the 1 mL glass vial containing the ligand solution was added an equimolar amount of metal precursor solution (10 mM in toluene) to form the metal-ligand composition solution. The reaction mixture was heated to 70–80° C. for 1–2 hours. Method B: Similar to Method A except the reaction mixture was heated to 60° C. for 1–2 hours. Method C: Similar to Method A except the reaction mixture was heated to 80° C. for 1–2 hours. The residual solvent and volatile byproducts were removed by blowing a stream of Argon over the 1 mL vial. The composition was redissolved in toluene prior to addition of alkylation and activator solution. Method D: Similar to Method A except the concentration of ligand and metal precursor solutions were 5 mM. The reaction mixture was allowed to sit at room temperature for 35 min and than was heated to 70–80° C. for 10 min. Method E: Similar to Method B except the concentration of ligand and metal precursor solutions were 5 mM. Method F: Similar to Method A except the concentration of ligand solution was 5 mM and metal precursor solution was 10 mM. The reaction mixture was heated for 30 min to 50° C. Method G: Similar to Method A except the concentration of ligand solution was 15 mM and metal precursor solution was 10 mM. The reaction mixture was heated for 1 hour to 70° C. Method H: Similar to Method A except the concentration of ligand solution was 60 mM and metal precursor solution was 5 mM. The reaction mixture was heated for 45 min to 70° C. Method I: Similar to Method G except the concentration of ligand solution was 25 mM and metal precursor solution was 5 mM. Method J: Similar to Method H except the concentration of ligand solution was 12 mM and metal precursor solution was 5 mM.

Preparation of the group 13 reagent and activator stock solutions: The "activator solution" is a solution of N,N'-dimethylanilinium tetrakis(pentafluorophenyl)borate in toluene ("$ABF_{20}$"). The molarity of this solution is indicated in the "activation method" of the individual example described below. The solution is heated to approximately 85° C. to dissolve the reagent. The "group 13 reagent" solution is either a solution of triisobutyl aluminium ("TIBA") or a solution of trimethylaluminium ("TMA") or a solution of Modified Methylaluminoxane 3A (from Azko Chemical Inc., Chicago, Ill.) ("MMAO") or a solution of Polymethylaluminoxane-Improved Process (from Azko Chemical Inc., Chicago, Il) ("PMAO"), all "group 13 reagent" solutions were solutions in toluene. The molarity of the solutions used is indicated in the "activation method" of the individual example described below.

Activation methods and Injection of solutions into the pressure reactor vessel, The following methods were employed to activate and inject the metal-ligand compositions for the examples in the Tables 1–3. Method AA: To the metal-ligand composition, 20 mole equivalents (per metal precursor) of a 500 mM solution of 1-octene in toluene were added to the metal ligand composition in the 1 mL vial. Then, the appropriate amount of the group 13 reagent solution as a 50 mM solution, containing the indicated equivalents group 13 reagent (per metal precursor) in the specific example, was added to the 1 mL vial. After 45 sec, 1.1 mol equivalents (per metal precursor) of the "activator solution" (2.5 mM) was added to the 1 mL vial. About another 30 seconds later, a fraction of the 1 mL vial contents corresponding to the indicated "catalyst amount injected"

was injected into the prepressurized reaction vessel and was followed immediately by injection of toluene to bring the total volume injected to 0.400–0.500 mL. Method BB: similar to Method AA except the concentration of the activator solution was 5 mM. Method CC: To the metal-ligand composition, the appropriate amount of the group 13 reagent solution as a 50 mM solution, containing the indicated equivalents group 13 reagent (per metal precursor) in the specific example, was added to the 1 mL vial. After 40 sec, the indicated amount of the "activator solution" (2.5 mM) was added to the 1 mL vial. About another 40 seconds later, a fraction of the 1 mL vial contents corresponding to the indicated "catalyst amount injected" was injected into the prepressurized reaction vessel, and was followed immediately by injection of toluene to bring the total volume injected to 0.400–0.500 mL. Method DD: To the metal-ligand composition, the appropriate amount of the group 13 reagent solution (50 mM), containing the indicated equivalents group 13 reagent (per metal precursor) in the specific example, was added to the 1 mL vial that was kept at 50–60° C. After about 10 min, the indicated amount of the "activator solution" (2.5 mM) was added to the 1 mL vial. About another 70 seconds later, a fraction of the 1 mL vial contents containing the indicated "catalyst amount injected" was injected into the prepressurized reaction vessel and was followed immediately by injection of toluene to bring the total volume injected to 0.400–0.500 mL.

Polymerization: The polymerization reaction was allowed to continue for 60–900 seconds, during which time the temperature and pressure were maintained at their pre-set levels by computer control. The specific polymerization times for each polymerization are shown in Tables 1–3. After the reaction time elapsed, the reaction was quenched by addition of an overpressure of carbon dioxide sent to the reactor. The polymerization times were the lesser of the maximum desired polymerization time or the time taken for a predetermined amount of monomer gas to be consumed in the polymerization reaction.

Product work up: Propylene Polymerizations: After the polymerization reaction, the glass vial insert, containing the polymer product and solvent, was removed from the pressure cell and removed from the inert atmosphere dry box, and the volatile components were removed using a centrifuge vacuum evaporator. After most of the volatile components had evaporated, the vial contents were dried thoroughly by evaporation at elevated temperature under reduced pressure. The vial was then weighed to determine the yield of polymer product. The polymer product was then analyzed by rapid GPC, as described above to determine the molecular weight of the polymer produced, and by FTIR spectroscopy to determine the crystallinity index. The melting point of selected samples was measured by DSC, as described above.

TABLE 1

| Ligand | Metal precursor | complex-ation method | Group 13 reagent and mole equiv. | Activator and mol equiv. | acti-vation method | catalyst amount injected nmol | Polym. temp. (Celsius) | Polym. time (sec) | Activity (g polymer/ (min * mmol) | FTIR index | Mp DSC data (Celsius) | Mw (/1000) (PDI) |
|---|---|---|---|---|---|---|---|---|---|---|---|---|
| LL5 | HfBz$_4$ | A | 6 MMAO | 1.1 ABF$_{20}$ | BB | 50 | 110 | 76 | 4683 | 0.8 | 128 | 333 (2.0) |
| LL5 | HfBz$_4$ | A | 6 MMAO | 1.1 ABF$_{20}$ | BB | 100 | 130 | 89 | 2379 | 0.82 | | 151 (1.9) |
| LL5 | ZrBz$_4$ | A | 6 MMAO | 1.1 ABF$_{20}$ | BB | 50 | 110 | 182 | 1079 | 0.76 | 108 | 106 (1.6) |
| LL5 | ZrBz$_4$ | A | 6 MMAO | 1.1 ABF$_{20}$ | BB | 100 | 130 | 298 | 499 | 0.68 | | 82 (1.5) |
| LL5 | TiBz$_4$ | F | 5 PMAO | 1.1 ABF$_{20}$ | BB | 200 | 90 | 600 | 13 | 0.5 | | 979 (1.9) |
| LL4 | HfBz$_4$ | A | 6 MMAO | 1.1 ABF$_{20}$ | BB | 50 | 110 | 179 | 1470 | 0.86 | 137 | 1116 (1.7) |
| LL4 | HfBz$_4$ | A | 6 MMAO | 1.1 ABF$_{20}$ | BB | 100 | 130 | 210 | 720 | 0.88 | | 407 (1.7) |
| LL4 | ZrBz$_4$ | A | 6 MMAO | 1.1 ABF$_{20}$ | BB | 50 | 110 | 375 | 449 | 0.82 | | 271 (1.6) |
| LL4 | ZrBz$_4$ | A | 6 MMAO | 1.1 ABF$_{20}$ | BB | 100 | 130 | 601 | 128 | 0.82 | | 135 (1.7) |
| LL14 | HfBz$_4$ | F | 5 PMAO | 1.1 ABF$_{20}$ | BB | 150 | 90 | 600 | 18 | 0.82 | | 404 (1.7) |
| LL14 | ZrBz$_4$ | F | 5 MMAO | 1.1 ABF$_{20}$ | BB | 150 | 90 | 600 | 17 | 0.63 | | nd |
| LL18 | HfBz$_4$ | A | 6 MMAO | 1.1 ABF$_{20}$ | CC | 60 | 110 | 94 | 2866 | 0.84 | | 407 (2.0) |
| LL18 | HfBz$_4$ | A | 6 MMAO | 1.1 ABF$_{20}$ | CC | 60 | 130 | 114 | 2136 | 0.84 | | 266 (2.1) |
| LL18 | ZrBz$_4$ | A | 6 MMAO | 1.1 ABF$_{20}$ | CC | 60 | 110 | 201 | 767 | 0.74 | | 122 (1.8) |
| LL18 | Zr(NMe$_2$)$_4$ | C | 10 TMA | 1.1 ABF$_{20}$ | DD | 100 | 110 | 111 | 992 | 0.74 | | 123 (1.7) |
| LL21 | HfBz$_4$ | A | 6 MMAO | 1.1 ABF$_{20}$ | CC | 40 | 110 | 91 | 5048 | 0.86 | 134 | 526 (2.5) |
| LL21 | HfBz$_4$ | A | 6 MMAO | 1.1 ABF$_{20}$ | CC | 60 | 130 | 92 | 2908 | 0.86 | 133 | 181 (2.2) |
| LL21 | ZrBz$_4$ | A | 6 MMAO | 1.1 ABF$_{20}$ | CC | 60 | 110 | 128 | 1366 | 0.77 | | 232 (1.8) |
| LL21 | ZrBz$_4$ | A | 6 MMAO | 1.1 ABF$_{20}$ | CC | 100 | 130 | 257 | 814 | 0.77 | | 117 (1.8) |
| LL23 | HfBz$_4$ | A | 6 MMAO | 1.1 ABF$_{20}$ | CC | 60 | 110 | 108 | 2664 | 0.84 | | 368 (2.0) |
| LL23 | ZrBz$_4$ | A | 6 MMAO | 1.1 ABF$_{20}$ | CC | 60 | 110 | 250 | 660 | 0.73 | | 118 (1.8) |
| LL20 | HfBz$_4$ | A | 6 MMAO | 1.1 ABF$_{20}$ | CC | 60 | 110 | 600 | 145 | 0.91 | | 2764 (1.5) |
| LL20 | ZrBz$_4$ | A | 6 MMAO | 1.1 ABF$_{20}$ | CC | 60 | 110 | 488 | 376 | 0.76 | | 627 (1.6) |
| LL49 | HfBz$_4$ | A | 6 MMAO | 1.1 ABF$_{20}$ | CC | 75 | 75 | 900 | 46 | 0.87 | | 1678 (2.5) |
| LL49 | ZrBz$_4$ | A | 6 MMAO | 1.1 ABF$_{20}$ | CC | 75 | 75 | 626 | 103 | 0.89 | | 24 (1.5) |

TABLE 2

| Ligand | Metal precursor | complex-ation method | Group 13 reagent and mole equiv. | Activator and mol equiv. | acti-vation method | catalyst amount injected nmol | Polym. temp. (Celsius) | Polym. time (sec) | Activity (g polymer/ (min * mmol) | FTIR index | Mp DSC data (Celsius) | Mw (/1000) (PDI) |
|---|---|---|---|---|---|---|---|---|---|---|---|---|
| LL1 | HfBz$_4$ | A | 5 MMAO | 1.1 ABF$_{20}$ | AA | 50 | 90 | 133 | 1973 | 0.32 | | 416 (1.6) |
| LL1 | ZrBz$_4$ | A | 5 MMAO | 1.1 ABF$_{20}$ | AA | 50 | 90 | 260 | 681 | 0.60 | | 577 1.6) |
| LL1 | HfBz$_4$ | A | 5 MMAO | 1.1 ABF$_{20}$ | BB | 100 | 110 | 293 | 295 | 0.57 | | 184 (1.8) |
| LL1 | ZrBz$_4$ | A | 5 MMAO | 1.1 ABF$_{20}$ | BB | 100 | 110 | 126 | 930 | 0.30 | | 162 (1.9) |

TABLE 2-continued

| Ligand | Metal precursor | complex-ation method | Group 13 reagent and mole equiv. | Activator and mol equiv. | acti-vation method | catalyst amount injected nmol | Polym. temp. (Celsius) | Polym. time (sec) | Activity (g polymer/ (min * mmol) | FTIR index | Mp DSC data (Celsius) | Mw (/1000) (PDI) |
|---|---|---|---|---|---|---|---|---|---|---|---|---|
| LL7 | HfBz$_4$ | A | 5 MMAO | 1.1 ABF$_{20}$ | BB | 100 | 110 | 141 | 758 | 0.78 | | 378 (1.8) |
| LL7 | ZrBz$_4$ | A | 5 MMAO | 1.1 ABF$_{20}$ | BB | 100 | 110 | 165 | 536 | 0.65 | | 203 (1.9) |
| LL2 | HfBz$_4$ | A | 6 MMAO | 1.1 ABF$_{20}$ | CC | 75 | 110 | 900 | 83 | 0.92 | 146 | 123 (1.6) |
| LL2 | HfBz$_4$ | A | 6 MMAO | 1.1 ABF$_{20}$ | CC | 60 | 75 | 489 | 265 | 0.89 | 151 | 781 (1.8) |
| LL2 | ZrBz$_4$ | A | 6 MMAO | 1.1 ABF$_{20}$ | CC | 75 | 110 | 163 | 785 | 0.89 | 137 | 113 (1.5) |
| LL2 | ZrBz$_4$ | A | 6 MMAO | 1.1 ABF$_{20}$ | CC | 60 | 75 | 149 | 1643 | 0.87 | 142 | 393 (1.6) |
| LL3 | HfBz$_4$ | A | 6 MMAO | 1.1 ABF$_{20}$ | CC | 150 | 110 | 494 | 123 | 0.95 | 149 | 197 (2.1) |
| LL3 | HfBz$_4$ | A | 6 MMAO | 1.1 ABF$_{20}$ | CC | 60 | 75 | 602 | 153 | 0.93 | 153 | 977 (1.8) |
| LL3 | ZrBz$_4$ | A | 6 MMAO | 1.1 ABF$_{20}$ | CC | 60 | 110 | 900 | 91 | 0.90 | 142 | 298 (1.8) |
| LL10 | HfBz$_4$ | A | 6 MMAO | 1.1 ABF$_{20}$ | CC | 150 | 110 | 900 | 30 | 0.93 | 149 | 202 (2.4) |
| LL10 | ZrBz$_4$ | A | 6 MMAO | 1.1 ABF$_{20}$ | CC | 60 | 110 | 900 | 38 | 0.89 | 139 | 322 (2.2) |
| LL53 | HfBz$_4$ | B | 6 MMAO | 1.1 ABF$_{20}$ | CC | 150 | 110 | 485 | 111 | 0.93 | | 122 (1.5) |
| LL53 | ZrBz$_4$ | B | 6 MMAO | 1.1 ABF$_{20}$ | CC | 150 | 110 | 124 | 629 | 0.92 | | 85 (1.6) |
| LL54 | HfBz$_4$ | B | 6 MMAO | 1.1 ABF$_{20}$ | CC | 150 | 110 | 153 | 449 | 0.94 | | 99 (1.5) |
| LL54 | ZrBz$_4$ | B | 6 MMAO | 1.1 ABF$_{20}$ | CC | 150 | 110 | 104 | 744 | 0.91 | | 106 (1.6) |
| LL6 | HfBz$_4$ | A | 6 MMAO | 1.1 ABF$_{20}$ | CC | 75 | 110 | 900 | 105 | 0.89 | 146 | 526 (1.9) |
| LL6 | HfBz$_4$ | A | 6 MMAO | 1.1 ABF$_{20}$ | CC | 60 | 75 | 900 | 107 | 0.90 | 150 | 1969 (1.7) |
| LL6 | ZrBz$_4$ | A | 6 MMAO | 1.1 ABF$_{20}$ | CC | 75 | 110 | 709 | 152 | 0.86 | 135 | 164 (1.5) |
| LL6 | ZrBz$_4$ | A | 6 MMAO | 1.1 ABF$_{20}$ | CC | 60 | 75 | 209 | 598 | 0.90 | 139 | 317 (1.5) |
| LL6 | Hf(NMe$_2$)$_4$ | C | 10 TMA | 1.1 ABF$_{20}$ | DD | 150 | 110 | 126 | 687 | 0.91 | | 197 (1.8) |
| LL6 | Hf(NMe$_2$)$_4$ | C | 10 TMA | 1.1 ABF$_{20}$ | DD | 150 | 110 | 96 | 966 | 0.87 | | 109 (1.5) |
| LL12 | HfBz$_4$ | B | 6 MMAO | 1.1 ABF$_{20}$ | CC | 150 | 110 | 675 | 102 | 0.76 | | 87 (1.5) |
| LL12 | ZrBz$_4$ | B | 6 MMAO | 1.1 ABF$_{20}$ | CC | 150 | 110 | 112 | 635 | 0.56 | | 98 (1.6) |
| LL13 | HfBz$_4$ | B | 6 MMAO | 1.1 ABF$_{20}$ | CC | 150 | 110 | 901 | 29 | 0.78 | | 83 (1.6) |
| LL13 | ZrBz$_4$ | B | 6 MMAO | 1.1 ABF$_{20}$ | CC | 150 | 110 | 117 | 649 | 0.60 | | 109 (1.5) |
| LL9 | HfBz$_4$ | D | 5 PMAO | 1.1 ABF$_{20}$ | BB | 100 | 110 | 600 | 81 | 0.65 | | 56 (1.8) |
| LL9 | ZrBz$_4$ | E | 5 PMAO | 1.1 ABF$_{20}$ | BB | 100 | 110 | 129 | 803 | 0.47 | | 91 (1.5) |
| LL8 | HfBz$_4$ | D | 5 PMAO | 1.1 ABF$_{20}$ | BB | 100 | 110 | 600 | 74 | 0.66 | | 156 (1.6) |
| LL8 | ZrBz$_4$ | E | 5 PMAO | 1.1 ABF$_{20}$ | BB | 100 | 110 | 194 | 460 | 0.48 | | 144 (1.5) |
| LL25 | HfBz$_4$ | A | 6 MMAO | 1.1 ABF$_{20}$ | CC | 60 | 75 | 617 | 150 | 0.77 | | 674 (1.8) |
| LL25 | ZrBz$_4$ | A | 6 MMAO | 1.1 ABF$_{20}$ | CC | 60 | 75 | 159 | 1172 | 0.65 | | 144 (2.2) |

TABLE 3

| Ligand | Metal precursor | complex-ation method | Group 13 reagent and mole equiv. | Activator and mol equiv. | activation method | catalyst amount injected nmol | Polym. temp. (Celsius) | Polym. time (sec) | Activity (g polymer/ (min * mmol) | FTIR index | Mp DSC data (Celsius) | Mw (/1000) (PDI) |
|---|---|---|---|---|---|---|---|---|---|---|---|---|
| LL46 | TiBz4 | G | 5 MMAO | 1.1 ABF$_{20}$ | AA | 300 | 90 | 900 | 8 | 0.51 | | 103 (2.5) |
| LL46 | ZrBz4 | G | 5 MMAO | 1.1 ABF$_{20}$ | AA | 200 | 110 | 650 | 22 | 0.63 | | 35 (2.7) |
| LL46 | HfBz4 | H | 5 MMAO | 1.1 ABF$_{20}$ | AA | 150 | 90 | 314 | 98 | 0.75 | | 25 (2.0) |
| LL37 | ZrBz4 | I | 5 MMAO | 1.1 ABF$_{20}$ | AA | 75 | 90 | 900 | 46 | 0.78 | | 5 (1.4) |
| LL37 | ZrBz4 | J | 5 TIBA | 1.1 ABF$_{20}$ | AA | 75 | 90 | 900 | 36 | 0.72 | | 4 (3.3) |
| LL48 | ZrBz4 | H | 5 MMAO | 1.1 ABF$_{20}$ | AA | 150 | 90 | 113 | 417 | 0.57 | | 12 (2.2) |
| LL48 | HfBz4 | H | 5 MMAO | 1.1 ABF$_{20}$ | AA | 300 | 90 | 138 | 192 | 0.69 | | 102 (2.9) |
| LL48 | ZrBz4 | G | 5 MMAO | 1.1 ABF$_{20}$ | AA | 200 | 110 | 189 | 170 | 0.52 | | 41 (2.5) |
| LL48 | HfBz4 | G | 5 MMAO | 1.1 ABF$_{20}$ | AA | 200 | 110 | 312 | 86 | 0.50 | | 49 (4.1) |
| LL31 | ZrBz4 | I | 5 MMAO | 1.1 ABF$_{20}$ | AA | 75 | 90 | 323 | 261 | 0.49 | | 2 (1.2) |
| LL31 | HfBz4 | I | 5 MMAO | 1.1 ABF$_{20}$ | AA | 150 | 90 | 304 | 148 | 0.69 | | 11 (1.7) |
| LL31 | ZrBz4 | J | 5 TIBA | 1.1 ABF$_{20}$ | AA | 75 | 90 | 358 | 218 | 0.43 | | 3 (2.6) |
| LL31 | HfBz4 | J | 5 TIBA | 1.1 ABF$_{20}$ | AA | 75 | 90 | 651 | 127 | 0.57 | | 18 (4.2) |
| LL28 | ZrBz4 | H | 5 MMAO | 1.1 ABF$_{20}$ | AA | 150 | 90 | 80 | 885 | 0.52 | | 28 (2.0) |
| LL28 | HfBz4 | H | 5 MMAO | 1.1 ABF$_{20}$ | AA | 300 | 90 | 62 | 779 | 0.59 | | 93 (1.9) |
| LL28 | ZrBz4 | G | 5 MMAO | 1.1 ABF$_{20}$ | AA | 200 | 110 | 105 | 320 | 0.46 | | 35 (2.7) |
| LL28 | HfBz4 | G | 5 MMAO | 1.1 ABF$_{20}$ | AA | 200 | 110 | 92 | 455 | 0.51 | | 80 (2.9) |
| LL29 | ZrBz4 | A | 5 MMAO | 1.1 ABF$_{20}$ | AA | 50 | 90 | 160 | 855 | 0.51 | | 19 (1.9) |
| LL29 | HfBz4 | A | 5 MMAO | 1.1 ABF$_{20}$ | AA | 50 | 90 | 358 | 437 | 0.42 | | 115 (1.6) |
| LL30 | ZrBz4 | I | 5 MMAO | 1.1 ABF$_{20}$ | AA | 75 | 90 | 154 | 663 | 0.38 | | 42 (2.0) |
| LL30 | HfBz4 | I | 5 MMAO | 1.1 ABF$_{20}$ | AA | 150 | 90 | 193 | 184 | 0.45 | | 104 (2.0) |
| LL30 | ZrBz4 | J | 5 TIBA | 1.1 ABF$_{20}$ | AA | 75 | 90 | 166 | 592 | 0.38 | | 51 (4.2) |
| LL30 | HfBz4 | J | 5 TIBA | 1.1 ABF$_{20}$ | AA | 75 | 90 | 636 | 215 | 0.36 | | 132 (6.3) |
| LL30 | HfBz4 | J | 5 PMAO | 1.1 ABF$_{20}$ | AA | 150 | 110 | 208 | 136 | 0.39 | | 49 (4.9) |
| LL38 | ZrBz4 | I | 5 MMAO | 1.1 ABF$_{20}$ | AA | 75 | 90 | 163 | 624 | 0.74 | | 6 (1.5) |
| LL38 | ZrBz4 | I | 5 PMAO | 1.1 ABF$_{20}$ | AA | 75 | 90 | 116 | 809 | 0.73 | | 6 (1.5) |
| LL38 | TiBz4 | I | 5 MMAO | 1.1 ABF$_{20}$ | AA | 300 | 90 | 900 | 11 | 0.63 | | 533 (1.5) |
| LL38 | TiBz4 | I | 5 PMAO | 1.1 ABF$_{20}$ | AA | 300 | 90 | 900 | 12 | 0.63 | | 605 (1.9) |
| LL38 | HfBz4 | I | 5 MMAO | 1.1 ABF$_{20}$ | AA | 150 | 90 | 75 | 1579 | 0.75 | | 56 (2.0) |
| LL38 | HfBz4 | I | 5 PMAO | 1.1 ABF$_{20}$ | AA | 100 | 90 | 99 | 1421 | 0.74 | | 59 (1.9) |
| LL39 | ZrBz4 | A | 5 MMAO | 1.1 ABF$_{20}$ | AA | 50 | 90 | 901 | 112 | 0.39 | | 5 (1.4) |
| LL39 | HfBz4 | A | 5 MMAO | 1.1 ABF$_{20}$ | AA | 50 | 90 | 901 | 62 | 0.23 | | 34 (1.5) |

TABLE 3-continued

| Ligand | Metal precursor | complexation method | Group 13 reagent and mole equiv. | Activator and mol equiv. | activation method | catalyst amount injected nmol | Polym. temp. (Celsius) | Polym. time (sec) | Activity (g polymer/ (min * mmol) | FTIR index | Mp DSC data (Celsius) | Mw (/1000) (PDI) |
|---|---|---|---|---|---|---|---|---|---|---|---|---|
| LL40 | ZrBz4 | A | 5 MMAO | 1.1 ABF$_{20}$ | AA | 100 | 90 | 372 | 152 | 0.94 | | 9 (1.5) |
| LL40 | TiBz4 | A | 5 MMAO | 1.1 ABF$_{20}$ | AA | 300 | 90 | 900 | 13 | 0.86 | | 38 (1.8) |
| LL40 | HfBz4 | A | 5 MMAO | 1.1 ABF$_{20}$ | AA | 50 | 90 | 154 | 1120 | 0.95 | | 103 (1.4) |
| LL32 | ZrBz4 | I | 5 PMAO | 1.1 ABF$_{20}$ | AA | 75 | 90 | 124 | 981 | 0.52 | | 47 (2.3) |
| LL32 | HfBz4 | I | 5 PMAO | 1.1 ABF$_{20}$ | AA | 100 | 90 | 128 | 776 | 0.67 | | 131 (1.7) |
| LL45 | ZrBz4 | H | 5 MMAO | 1.1 ABF$_{20}$ | AA | 150 | 90 | 227 | 123 | 0.21 | | 3 (1.2) |
| LL45 | HfBz4 | H | 5 MMAO | 1.1 ABF$_{20}$ | AA | 300 | 90 | 150 | 156 | 0.24 | | 8 (1.6) |
| LL45 | TiBz4 | G | 5 MMAO | 1.1 ABF$_{20}$ | AA | 300 | 90 | 900 | 19 | 0.61 | | 2601 (2.9) |
| LL26 | ZrBz4 | H | 5 MMAO | 1.1 ABF$_{20}$ | AA | 150 | 90 | 672 | 46 | 0.35 | | 9 (1.7) |
| LL26 | HfBz4 | H | 5 MMAO | 1.1 ABF$_{20}$ | AA | 300 | 90 | 900 | 18 | 0.27 | | 25 (1.9) |
| LL27 | ZrBz4 | H | 5 MMAO | 1.1 ABF$_{20}$ | AA | 150 | 90 | 312 | 114 | 0.70 | | 36 (2.6) |
| LL27 | HfBz4 | H | 5 MMAO | 1.1 ABF$_{20}$ | AA | 300 | 90 | 107 | 259 | 0.74 | | 179 (1.8) |
| LL33 | ZrBz4 | I | 5 MMAO | 1.1 ABF$_{20}$ | AA | 75 | 90 | 349 | 231 | 0.57 | | 31 (1.9) |
| LL33 | HfBz4 | I | 5 MMAO | 1.1 ABF$_{20}$ | AA | 150 | 90 | 255 | 169 | 0.57 | | 165 (1.9) |
| LL43 | ZrBz4 | H | 5 MMAO | 1.1 ABF$_{20}$ | AA | 150 | 90 | 900 | 16 | 0.49 | | 56 (8.0) |
| LL43 | HfBz4 | H | 5 MMAO | 1.1 ABF$_{20}$ | AA | 300 | 90 | 900 | 7 | 0.50 | | nd |

Example 42

Propylene Polymerizations Using Isolated Complexes. A Total of Thirty-three (33) Separate Polymerization Reactions were Performed as Described Herein Preparation of the polymerization reactor prior to injection of catalyst composition: The polymerization reactor was prepared in the manner described in Example 41.

Preparation of the group 13 reagent and activator stock solutions: The "activator solution" is either a solution of N,N'-dimethylanilinium tetrakis(pentafluorophenyl)borate in toluene ("ABF$_{20}$") or a solution of tris(pentafluorophenyl)borane in toluene ("BF$_{15}$"). The "ABF$_{20}$" solution is heated to approximately 85° C. to dissolve the reagent. The molarity is indicated in the "activation method" of the individual example described below. The "group 13 reagent" solution is either a solution of triisobutyl aluminium ("TIBA") or a solution of trimethylaluminium ("TMA") or a solution of triethylaluminium ("TEAL") or a solution of diisobutylaluminium hydride ("DIBAL") or a solution of Modified Methylaluminoxane 3A (Azko Chemical Inc., Chicago, Ill.) ("MMAO") or a solution of Polymethylaluminoxane-Improved Process (Azko Chemical Inc., Chicago, Ill.) ("PMAO"), all "group 13 reagent" solutions were solutions in toluene. The molarity of the solutions used is indicated in the "activation method" of the individual example described below.

Activation method and Injection of solutions into the pressure reactor vessel: The following methods were employed to activate and inject the isolated complexes as indicated in the Table 4. Method II: An appropriate amount of a 0.050M solution of the group 13 reagent, containing the indicated equivalents group 13 reagent (per isolated complex) in the specific examples in Table 4, is dispensed into a 1 mL vial. An appropriate amount complex solution (3–4 mM in dichloroethylene) containing 0.4 mmol metal complex is added. After 10 min, 0.44 mmol of the activator solution in toluene (2.5 mM) was added to the 1 mL vial. About another 60 seconds later a fraction of the total 1 mL vial contents containing the indicated "catalyst amount injected" being identified in Table 4 was injected into the pre-pressurized reaction vessel and was followed immediately by injection of toluene to increase the total volume injected of 0.400 mL. Method JJ: similar to Method II except that the concentration of the group 13 reagent solution was 0.200 M. Method KK: similar to Method JJ except that the 1 mL vial was heated to 50–60° C. Method LL: 40 uL of the 10 mM complex solution in toluene is dispensed into a 1 mL vial. An appropriate amount based on the equivalents presented in table 4 of a 0.050M solution of the group 13 reagent is added. After 10 min, 0.44 mmol of the activator solution in toluene (5 mM) was added to the 1 mL vial. About another 60 seconds later, a fraction of the total 1 mL vial contents containing the indicated "catalyst amount injected" being identified in table 4 was injected into the prepressurized reaction vessel and was followed immediately by injection of toluene to increase the total volume injected of 0.400 mL. Method MM: An appropriate amount based on the equivalents presented in table 4 of a 0.020M solution of the group 13 reagent is dispensed into a 1 mL vial. 80 uL of a complex solution containing 0.4 mmol metal complex (5 mM in toluene) is added. After 50 sec, an appropriate amount of the activator solution in toluene ("ABF20" is 2.5 mM and "BF15" is 5 mM), containing the indicated equivalents of "activator" (per mole isolated complex) in the specific examples in table 4, was added to the 1 mL vial. About another 60 seconds later a fraction of the total 1 mL vial contents containing the indicated "catalyst amount injected" being identified in table 4 was injected into the prepressurized reaction vessel and was followed immediately by injection of toluene to increase the total volume injected of 0.500 mL.

Polymerization and Product work up: The polymerization reaction and product work up were preformed in the manner described in Example 41.

TABLE 4

| Complex | complex-ation method | Group 13 reagent and mole equiv. | Activator and mol equiv. | Activation method | catalyst amount injected nmol | Polym. temp. (Celsius) | Polym. time (sec) | Activity (g polymer/ (min * mmol) | Crystallinity index | Molecular weight Mw (k) | Melting point by DSC |
|---|---|---|---|---|---|---|---|---|---|---|---|
| C1 | 5 TEAL | 1.1 $ABF_{20}$ | MM | 25 | 90 | 80 | 292 | 333 | 0.6 | 417 | |
| C1 | 5 TIBA | 1.1 $ABF_{20}$ | MM | 25 | 90 | 80 | 345 | 338 | 0.59 | 574 | |
| C1 | 5 MMAO | 1.1 $ABF_{20}$ | MM | 25 | 90 | 80 | 324 | 281 | 0.61 | 654 | |
| C1 | 5 MMAO | 2.2 $BF_{15}$ | MM | 25 | 90 | 120 | 440 | 134 | 0.61 | 780 | |
| C1 | 5 TEAL | 1.1 $ABF_{20}$ | MM | 25 | 110 | 80 | 600 | 144 | 0.58 | 228 | |
| C1 | 5 TIBA | 1.1 $ABF_{20}$ | MM | 25 | 110 | 80 | 471 | 215 | 0.56 | 129 | |
| C2 | 10 DIBAL | 1.1 $ABF_{20}$ | LL | 25 | 110 | 100 | 179 | 571 | 0.78 | 191 | |
| C2 | 10 DIBAL | 1.1 $ABF_{20}$ | LL | 55 | 110 | 100 | 110 | 1169 | 0.77 | 121 | |
| C2 | 10 TMA | 1.1 $ABF_{20}$ | LL | 25 | 110 | 100 | 600 | 29 | nd | nd | |
| C2 | 10 TMA | 1.1 $ABF_{20}$ | LL | 55 | 110 | 100 | 77 | 2129 | 0.79 | 84 | |
| C2 | 10 TIBA | 1.1 $ABF_{20}$ | LL | 55 | 110 | 100 | 600 | 48 | 0.79 | 260 | |
| C3 | 30 DIBAL | 1.1 $ABF_{20}$ | JJ | 20 | 110 | 50 | 99 | 3717 | 0.83 | 165 | 129 |
| C3 | 30 DIBAL | 1.1 $ABF_{20}$ | JJ | 20 | 130 | 50 | 90 | 3308 | 0.84 | 118 | 129 |
| C3 | 30 TIBA | 1.1 $ABF_{20}$ | JJ | 20 | 110 | 50 | 97 | 4013 | 0.82 | 222 | |
| C3 | 30 TIBA | 1.1 $ABF_{20}$ | JJ | 20 | 130 | 50 | 94 | 3177 | 0.83 | 102 | |
| C4 | 5 MMAO | 1.1 $ABF_{20}$ | MM | 25 | 90 | 80 | 157 | 1077 | 0.35 | 527 | |
| C4 | 5 PMAO | 1.1 $ABF_{20}$ | MM | 25 | 90 | 80 | 141 | 1194 | 0.35 | 716 | |
| C4 | 5 TIBA | 1.1 $ABF_{20}$ | MM | 20 | 90 | 80 | 140 | 1288 | 0.32 | 520 | |
| C4 | 5 MMAO | 2.2 $BF_{15}$ | MM | 25 | 90 | 80 | 157 | 985 | 0.3 | 734 | |
| C4 | 5 MMAO | 1.1 $ABF_{20}$ | MM | 25 | 110 | 80 | 162 | 717 | 0.36 | 220 | |
| C4 | 5 PMAO | 1.1 $ABF_{20}$ | MM | 25 | 110 | 80 | 166 | 685 | 0.35 | 292 | |
| C5 | 30 DIBAL | 1.1 $ABF_{20}$ | JJ | 20 | 110 | 50 | 179 | 1187 | 0.87 | 275 | 147 |
| C5 | 30 DIBAL | 1.1 $ABF_{20}$ | KK | 20 | 130 | 50 | 318 | 634 | 0.9 | 113 | 143 |
| C5 | 30 TIBA | 1.1 $ABF_{20}$ | JJ | 20 | 110 | 50 | 155 | 1707 | 0.91 | 246 | |
| C5 | 30 TIBA | 1.1 $ABF_{20}$ | KK | 20 | 130 | 50 | 391 | 485 | 0.9 | 247 | |
| C6 | 10 DIBAL | 1.1 $ABF_{20}$ | II | 20 | 110 | 100 | 263 | 219 | 0.92 | 58 | |
| C6 | 30 DIBAL | 1.1 $ABF_{20}$ | JJ | 20 | 130 | 200 | 900 | 34 | 0.93 | 14 | |
| C6 | 30 TIBA | 1.1 $ABF_{20}$ | JJ | 20 | 110 | 100 | 487 | 187 | 0.95 | 67 | |
| C6 | 30 TIBA | 1.1 $ABF_{20}$ | JJ | 20 | 130 | 200 | 900 | 40 | 0.93 | 18 | |
| C7 | 30 DIBAL | 1.1 $ABF_{20}$ | JJ | 20 | 110 | 100 | 80 | 3636 | 0.79 | 315 | |
| C7 | 30 DIBAL | 1.1 $ABF_{20}$ | JJ | 20 | 130 | 200 | 900 | 131 | 0.8 | 219 | |
| C7 | 10 TIBA | 1.1 $ABF_{20}$ | II | 20 | 110 | 100 | 73 | 3532 | 0.76 | 175 | |
| C7 | 30 TIBA | 1.1 $ABF_{20}$ | JJ | 20 | 130 | 200 | 900 | 175 | 0.8 | 274 | |

Example 42

Ethylene-Styrene or Ethylene-1-Octene Copolymerizations Using Metal-ligand Compositions. A Total of Twelve (12) Separate ethylene-1-octene Copolymerization Reactions were Performed and Thirty-nine (39) Separate ethylene-styrene Copolymerization Reactions were Performed as Described herein Preparation of the polymerization reactor prior to injection of catalyst composition: A pre-weighed glass vial insert and disposable stirring paddle were fitted to each reaction vessel of the reactor. The reactor was then closed, 0.10 mL of a 0.02 M group 13 reagent solution in toluene and 3.8 mL of toluene were injected into each pressure reaction vessel through a valve. The identity of the group 13 reagent solution is MMAO. The temperature was then set to 110° C., and the stirring speed was set to 800 rpm, and the mixture was exposed to ethylene at 100 psi pressure. An ethylene pressure of 100 psi in the pressure cell and the temperature setting were maintained, using computer control, until the end of the polymerization experiment.

Preparation of the group 13 reagent and activator stock solutions: The "activator solution" is a 5 mM solution of N,N'-dimethylanilinium tetrakis(pentafluorophenyl)borate in toluene ("$ABF_{20}$"). The solution is heated to approximately 85° C. to dissolve the reagent. The group 13 reagent solution is a solution of Modified Methylaluminoxane-3A (Azko) ("MMAO") in toluene.

In situ preparation of metal-ligand compositions: The following method was employed to prepare the metal-ligand compositions as indicated in the table 5–6. Method K: An appropriate amount ligand solution (10 mM in toluene) was dispensed in a 1 mL glass vial at a scale of 0.4–0.75 mmol. To the 1 mL glass vial containing the ligand solution was added an equimolar amount of metal precursor solution (10 mM in toluene) to form the metal-ligand composition solution. The reaction mixture was heated to 70–80° C. for 45 min.

Activation methods and Injection of solutions into the pressure reactor vessel: The following methods were employed to activate and inject the metal-ligand compositions as indicated in the tables 5–6. Method EE: To the ligand metal composition (preparation described above), 20 equivalents (per metal precursor equivalent) of a 500 mM solution of 1-octene in toluene was added to the metal ligand composition in the 1 mL vial. Then, the indicated amount of the group 13 reagent solution (50 mM) was added to the 1 mL vial. This mixture was held at room temperature for 60–70 sec, during which time, 0.420 mL of comonomer (styrene or 1-octene) followed immediately by 0.380 mL of toluene, were injected into the prepressurized reaction vessel. Then, the appropriate amount of the "activator solution" (5 mM) was added to the 1 mL vial. After about 30–40 sec, a fraction of the 1 mL vial contents containing the indicated "catalyst amount injected" were injected into the reaction vessel and was followed immediately by injection of toluene to increase the total volume injected of 0.400–0.500 mL.

Polymerization: The polymerization reaction was allowed to continue for 60–600 seconds, during which time the temperature and pressure were maintained at their pre-set levels by computer control. The specific times for each polymerization are shown in tables 5–6. The polymerization times were the lesser of the maximum desired polymerization time or the time taken for a predetermined amount of monomer gas to be consumed in the polymerization reaction. After the reaction time elapsed, the reaction was quenched by addition of an overpressure of carbon dioxide sent to the reactor.

Product work up: ethylene/styrene or ethylene/1-octene copolymerizations After the polymerization reaction, the glass vial insert, containing the polymer product and solvent, was removed from the pressure cell and removed from the inert atmosphere dry box, and the volatile components were removed using a centrifuge vacuum evaporator. After substantial evaporation of the volatile components, the vial contents were dried thoroughly by evaporation at elevated temperature under reduced pressure. The vial was then weighed to determine the yield of polymer product. The polymer product was then analyzed by rapid GPC, as described above to determine the molecular weight of the polymer produced, and by FTIR or Raman spectroscopy to determine the comonomer incorporation. Results are presented in the Table 5 for ethylene-styrene copolymerizations and Table 6 for ethylene-1-octene copolymerizations.

TABLE 5

| Ligand | Metal precursor | Comonomer | complexation method | Group 13 reagent and mole equiv. | Activator and mol equiv. | activation method |
|---|---|---|---|---|---|---|
| LL46 | $ZrBz_4$ | Styrene | K | 6 MMAO | 1.1 $ABF_{20}$ | EE |
| LL46 | $HfBz_4$ | Styrene | K | 6 MMAO | 1.1 $ABF_{20}$ | EE |
| LL37 | $ZrBz_4$ | Styrene | K | 5 MMAO | 1.1 $ABF_{20}$ | EE |
| LL37 | $HfBz_4$ | Styrene | K | 5 MMAO | 1.1 $ABF_{20}$ | EE |
| LL48 | $ZrBz_4$ | Styrene | K | 5 MMAO | 1.1 $ABF_{20}$ | EE |
| LL48 | $HfBz_4$ | Styrene | K | 5 MMAO | 1.1 $ABF_{20}$ | EE |
| LL31 | $ZrBz_4$ | Styrene | K | 5 MMAO | 1.1 $ABF_{20}$ | EE |
| LL31 | $HfBz_4$ | Styrene | K | 5 MMAO | 1.1 $ABF_{20}$ | EE |
| LL28 | $ZrBz_4$ | Styrene | K | 5 MMAO | 1.1 $ABF_{20}$ | EE |
| LL28 | $HfBz_4$ | Styrene | K | 5 MMAO | 1.1 $ABF_{20}$ | EE |
| LL29 | $ZrBz_4$ | Styrene | K | 5 MMAO | 1.1 $ABF_{20}$ | EE |
| LL29 | $HfBz_4$ | Styrene | K | 5 MMAO | 1.1 $ABF_{20}$ | EE |
| LL29 | $TiBz_4$ | Styrene | K | 5 MMAO | 1.1 $ABF_{20}$ | EE |
| LL30 | $ZrBz_4$ | Styrene | K | 5 MMAO | 1.1 $ABF_{20}$ | EE |
| LL30 | $HfBz_4$ | Styrene | K | 5 MMAO | 1.1 $ABF_{20}$ | EE |
| LL38 | $ZrBz_4$ | Styrene | K | 5 MMAO | 1.1 $ABF_{20}$ | EE |
| LL38 | $HfBz_4$ | Styrene | K | 5 MMAO | 1.1 $ABF_{20}$ | EE |
| LL39 | $ZrBz_4$ | Styrene | K | 5 MMAO | 1.1 $ABF_{20}$ | EE |
| LL39 | $HfBz_4$ | Styrene | K | 5 MMAO | 1.1 $ABF_{20}$ | EE |
| LL40 | $ZrBz_4$ | Styrene | K | 5 MMAO | 1.1 $ABF_{20}$ | EE |
| LL40 | $HfBz_4$ | Styrene | K | 5 MMAO | 1.1 $ABF_{20}$ | EE |
| LL32 | $ZrBz_4$ | Styrene | K | 5 MMAO | 1.1 $ABF_{20}$ | EE |
| LL32 | $HfBz_4$ | Styrene | K | 5 MMAO | 1.1 $ABF_{20}$ | EE |
| LL45 | $ZrBz_4$ | Styrene | K | 5 MMAO | 1.1 $ABF_{20}$ | EE |
| LL45 | $HfBz_4$ | Styrene | K | 5 MMAO | 1.1 $ABF_{20}$ | EE |
| LL26 | $ZrBz_4$ | Styrene | K | 5 MMAO | 1.1 $ABF_{20}$ | EE |
| LL26 | $HfBz_4$ | Styrene | K | 5 MMAO | 1.1 $ABF_{20}$ | EE |
| LL27 | $ZrBz_4$ | Styrene | K | 5 MMAO | 1.1 $ABF_{20}$ | EE |
| LL27 | $HfBz_4$ | Styrene | K | 5 MMAO | 1.1 $ABF_{20}$ | EE |
| LL33 | $ZrBz_4$ | Styrene | K | 5 MMAO | 1.1 $ABF_{20}$ | EE |
| LL33 | $HfBz_4$ | Styrene | K | 5 MMAO | 1.1 $ABF_{20}$ | EE |
| LL43 | $ZrBz_4$ | Styrene | K | 5 MMAO | 1.1 $ABF_{20}$ | EE |
| LL43 | $HfBz_4$ | Styrene | K | 5 MMAO | 1.1 $ABF_{20}$ | EE |
| LL1 | $ZrBz_4$ | Styrene | K | 5 MMAO | 1.1 $ABF_{20}$ | EE |
| LL1 | $HfBz_4$ | Styrene | K | 5 MMAO | 1.1 $ABF_{20}$ | EE |
| LL4 | $ZrBz_4$ | Styrene | K | 5 MMAO | 1.1 $ABF_{20}$ | EE |
| LL4 | $HfBz_4$ | Styrene | K | 5 MMAO | 1.1 $ABF_{20}$ | EE |
| LL7 | $ZrBz_4$ | Styrene | K | 5 MMAO | 1.1 $ABF_{20}$ | EE |
| LL7 | $HfBz_4$ | Styrene | K | 5 MMAO | 1.1 $ABF_{20}$ | EE |

TABLE 5-continued

| Ligand | catalyst amount injected nmol | Polym. temp. (Celsius) | Polym. time (sec) | Activity (g polymer/ (min * mmol) | Mol % Styrene by linear regres. | mol % styrene by PLS | Mw (/1000) (PDI) |
|---|---|---|---|---|---|---|---|
| LL46 | 133 | 110 | 174 | 497 | 12.2 | | 5 (2.5) |
| LL46 | 133 | 110 | 1366 | 35 | | 14.6 | 3 (1.3) |
| LL37 | 75 | 110 | 901 | 162 | 9 | | bimodal |
| LL37 | 75 | 110 | 901 | 26 | 14.1 | | bimodal |
| LL48 | 150 | 110 | 323 | 227 | | 1.7 | 36 (nd) |
| LL48 | 300 | 110 | 755 | 47 | | 2.7 | 342 (nd) |
| LL31 | 75 | 110 | 254 | 601 | | 1 | 13 (1.6) |
| LL31 | 75 | 110 | 900 | 58 | | 2.4 | 544 (2.0) |
| LL28 | 150 | 110 | 127 | 809 | | 3.4 | 86 (nd) |
| LL28 | 300 | 110 | 289 | 180 | | 5.8 | 209 (nd) |
| LL29 | 75 | 110 | 141 | 1273 | | 1.9 | 26 (1.9) |
| LL29 | 75 | 110 | 375 | 461 | | 3.8 | 194 m (1.8) |
| LL29 | 200 | 110 | 600 | 15 | | 1.1 | 105 (5 |
| LL30 | 75 | 110 | 158 | 1172 | | 1.9 | 105 (4.8) |
| LL30 | 75 | 110 | 604 | 58 | | 3.1 | 281 (2.0) |
| LL38 | 75 | 110 | 102 | 1906 | | 1.3 | 26 (2.1) |
| LL38 | 75 | 110 | 269 | 717 | | 4.2 | 180 (2.2) |
| LL39 | 75 | 110 | 295 | 482 | | 1.3 | broad |
| LL39 | 75 | 110 | 900 | 140 | | 2.3 | broad |
| LL40 | 75 | 110 | 112 | 1817 | | 3.4 | 24 (2.0) |
| LL40 | 75 | 110 | 259 | 900 | | 11.4 | 207 (1.9) |
| LL32 | 75 | 110 | 263 | 558 | | 1.1 | 76 (3.9) |
| LL32 | 75 | 110 | 536 | 269 | | 2.3 | 251 (2.4) |
| LL45 | 150 | 110 | 178 | 478 | | 3.7 | 21 |
| LL45 | 300 | 110 | 716 | 59 | | 4 | 209 |
| LL26 | 150 | 110 | 397 | 196 | | 2.3 | 38 |
| LL26 | 300 | 110 | 900 | 31 | | 0.9 | 181 |
| LL27 | 150 | 110 | 900 | 58 | | 0.9 | 195 |
| LL27 | 300 | 110 | 900 | 35 | | 1.5 | 685 |
| LL33 | 75 | 110 | 900 | 106 | | 1 | 48 (2.4) |
| LL33 | 75 | 110 | 900 | 95 | | 1.4 | 307 (2.2) |
| LL43 | 150 | 110 | 900 | 65 | | 1.8 | |
| LL43 | 300 | 110 | 900 | 14 | | 2 | |
| LL1 | 75 | 110 | 896 | 150 | | 2.4 | 1346 (1.6) |
| LL1 | 75 | 110 | 901 | 112 | | 3.6 | 885 (1.9) |
| LL4 | 75 | 110 | 600 | 184 | 4.1 | | 1165 (1.9 |
| LL4 | 50 | 110 | 600 | 307 | 8 | | not dissolved |
| LL7 | 75 | 110 | 600 | 166 | 3 | | 872 (1.4) |
| LL7 | 50 | 110 | 600 | 147 | 2.9 | | 1732 (1.5) |

TABLE 6

| Ligand | Metal precursor | Comonomer | complexation method | Group 13 reagent and mole equiv. | Activator and mol equiv. | activation method | catalyst amount injected nmol | Polym. temp. (Celsius) | Polym. time (sec) | Activity (g polymer/ (min * mmol) | Mol % Octene by Raman | Mw (/1000) (PDI) |
|---|---|---|---|---|---|---|---|---|---|---|---|---|
| LL7 | TiBz$_4$ | C8 | K | 5 MMAO | 1.1 ABF$_{20}$ | EE | 200 | 110 | 600 | 32 | 8 | 2380 (1.4) |
| LL7 | ZrBz$_4$ | C8 | K | 5 MMAO | 1.1 ABF$_{20}$ | EE | 75 | 110 | 369 | 678 | 17 | 679 (2.3) |
| LL7 | HfBz$_4$ | C8 | K | 5 MMAO | 1.1 ABF$_{20}$ | EE | 50 | 110 | 600 | 553 | 28 | 641 (4.1) |
| LL4 | TiBz$_4$ | C8 | K | 5 MMAO | 1.1 ABF$_{20}$ | EE | 200 | 110 | 600 | 36 | 8 | 1341 (1.6) |
| LL4 | ZrBz$_4$ | C8 | K | 5 MMAO | 1.1 ABF$_{20}$ | EE | 75 | 110 | 198 | 1251 | 19 | 488 (2.3) |
| LL4 | HfBz$_4$ | C8 | K | 5 MMAO | 1.1 ABF$_{20}$ | EE | 50 | 110 | 431 | 822 | 27 | 1706 (3.4) |
| LL38 | TiBz$_4$ | C8 | K | 5 MMAO | 1.1 ABF$_{20}$ | EE | 200 | 110 | 600 | 84 | 6 | 170 (3.7) |
| LL38 | ZrBz$_4$ | C8 | K | 5 MMAO | 1.1 ABF$_{20}$ | EE | 75 | 110 | 61 | 4378 | 12 | 37 (2.0) |
| LL38 | HfBz$_4$ | C8 | K | 5 MMAO | 1.1 ABF$_{20}$ | EE | 50 | 110 | 113 | 2852 | 15 | 93 (1.9) |
| LL40 | TiBz$_4$ | C8 | K | 5 MMAO | 1.1 ABF$_{20}$ | EE | 200 | 110 | 403 | 148 | 10 | 151 (4.8) |
| LL40 | ZrBz$_4$ | C8 | K | 5 MMAO | 1.1 ABF$_{20}$ | EE | 75 | 110 | 60 | 4425 | 15 | 12 (1.9) |
| LL40 | HfBz$_4$ | C8 | K | 5 MMAO | 1.1 ABF$_{20}$ | EE | 50 | 110 | 107 | 3686 | 17 | 99 (2.2) |

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated herein by reference for all purposes.

What is claimed is:

1. A composition, comprising:
a ligand characterized by the general formula:

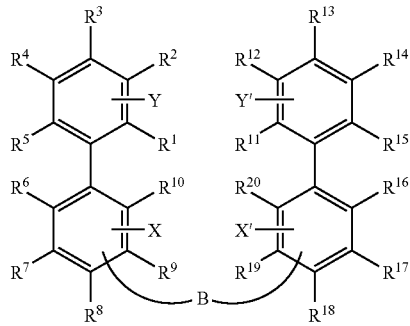

wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, and $R^{20}$ when present is independently selected from the group consisting of hydride, halide, and optionally substituted hydrocarbyl, heteroatom-containing hydrocarbyl, alkoxy, aryloxy, silyl, boryl, phosphino, amino, alkylthio, arylthio, thioxy, seleno, nitro, and combinations thereof; optionally two or more R groups can combine together into ring structures, with such ring structures having from 3 to 100 atoms in the ring not counting hydrogen atoms; B is a bridging group having from one to 50 atoms not counting hydrogen atoms; X and X' are the same or different and are independently selected from the group consisting of oxygen, sulfur, and —$PR^{30}$—, where $R^{30}$ is selected from the group consisting of hydride, halide, and optionally substituted hydrocarbyl, heteroatom-containing hydrocarbyl, silyl, boryl, alkoxy, aryloxy and combinations thereof; Y and Y' are the same or different and are independently selected from the group consisting of optionally substituted amino, phosphino, hydroxy, alkoxy, aryloxy, alkylthio, arylthio and thioxy;
a metal precursor compound characterized by the general formula $M(L)_n$ where M is a metal selected from groups 3–6 and Lanthanide elements of the Periodic Table of Elements, each L is a moiety that forms a covalent, dative or ionic bond with M; n is 1, 2, 3, 4, 5, or 6; and
optionally, at least one activator.

2. The composition of claim 1, wherein the ligand is characterized by the formula:

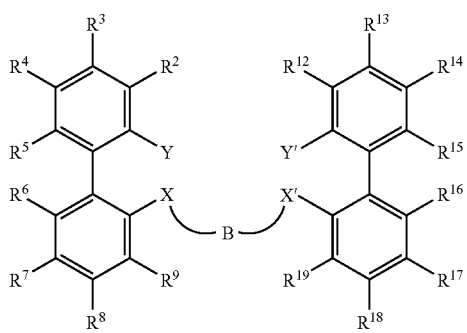

wherein $R^2$, $R^3$, $R^4$, $R^5$, $R^6$, $R^7$, $R^8$, $R^9$, $R^{12}$, $R^{13}$, $R^{14}$, $R^{15}$, $R^{16}$, $R^{17}$, $R^{18}$, and $R^{19}$ are as defined above, B is as defined above, X and X' are as defined above, and Y and Y' are as defined above with the proviso that each of Y and Y' include hydrogen.

3. The composition of claim 2, wherein the ligand is characterized by the formula:

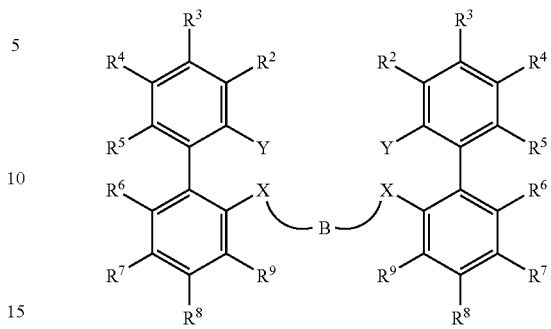

wherein each of $R^2$, $R^3$, $R^4$, $R^5$, $R^6$, $R^7$, $R^8$ and $R^9$ is independently selected from the group consisting of hydride, halide, and optionally substituted alkyl, alkenyl, alkynyl, heteroalkyl, heteroalkenyl, heteroalkynyl, aryl, heteroaryl, alkoxyl, aryloxyl, silyl, boryl, phosphino, amino, alkylthio, arylthio, thioxy, seleno, nitro, and combinations thereof.

4. The composition of claim 1, wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, and $R^{20}$ is independently selected from the group consisting of hydride, halide, and optionally substituted alkyl, heteroalkyl, aryl, heteroaryl, alkoxyl, aryloxyl, silyl, boryl, phosphino, amino, alkylthio, arylthio, thioxy, seleno, and nitro.

5. The composition of claim 4, wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, and $R^{20}$ is independently selected from the group consisting of hydride, halide, and optionally substituted alkyl, heteroalkyl, aryl, heteroaryl, alkoxyl, aryloxyl, silyl, amino, alkylthio, arylthio and thioxy.

6. The composition of claim 3, wherein each $R^2$ is not hydrogen.

7. The composition of claim 6, wherein each $R^2$ is independently selected from the group consisting of optionally substituted aryl and heteroaryl.

8. The composition of claim 3, wherein the bridging group B is selected from the group consisting of optionally substituted divalent hydrocarbyl and divalent heteroatom containing hydrocarbyl.

9. The composition of claim 8, wherein B is selected from the group consisting of optionally substituted divalent alkyl, alkenyl, alkynyl, heteroalkyl, heteroalkenyl, heteroalkynyl, aryl, heteroaryl and silyl.

10. The composition of claim 8, wherein B is represented by the general formula -$(Q''R^{40}_{2-z''})_{z'}$— wherein each Q'' is either carbon or silicon and each $R^{40}$ may be the same or different from the others such that each $R^{40}$ is selected from the group consisting of hydride and optionally substituted hydrocarbyl and heteroatom containing hydrocarbyl, and optionally two or more $R^{40}$ groups may be joined into a ring structure having from 3 to 50 atoms in the ring structure not counting hydrogen atoms; z' is an integer from 1 to 10; and z'' is 0, 1 or 2.

11. The composition of any of claim 1, 2, 3, 4, 5, 6, 7, 8, 9 or 10 wherein M is selected from the group consisting of Hf, Zr and Ti.

12. The composition of claim 3, wherein $R^7$ and $R^8$ are independently selected from the group consisting of halo, alkoxy, aryloxy, and amino.

13. The composition of claim 3, wherein at least one L is an anion.

* * * * *